US012663416B2

(12) United States Patent
Qin et al.

(10) Patent No.: US 12,663,416 B2
(45) Date of Patent: Jun. 23, 2026

(54) PARTICLE-BASED SENSORS AND METHODS USING PARTICLE-BASED SENSORS FOR DETECTION OF ANALYTES

(71) Applicant: Board of Regents, The University of Texas System, Austin, TX (US)

(72) Inventors: Zhenpeng Qin, Allen, TX (US);
Yaning Liu, Richardson, TX (US);
Jeffrey S. Kahn, Plano, TX (US);
Leonidas Bleris, Allen, TX (US);
Haihang Ye, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1091 days.

(21) Appl. No.: 17/358,688

(22) Filed: Jun. 25, 2021

(65) Prior Publication Data

US 2021/0405041 A1 Dec. 30, 2021

Related U.S. Application Data

(60) Provisional application No. 63/044,267, filed on Jun. 25, 2020.

(51) Int. Cl.
*G01N 33/543* (2006.01)
*C12Q 1/6825* (2018.01)
*G01N 33/569* (2006.01)

(52) U.S. Cl.
CPC ..... *G01N 33/54346* (2013.01); *C12Q 1/6825* (2013.01); *G01N 33/56983* (2013.01); *G01N 2333/08* (2013.01)

(58) Field of Classification Search
CPC ....... G01N 33/54346; G01N 33/56983; G01N 2333/08; C12Q 1/6825
See application file for complete search history.

(56) References Cited

U.S. PATENT DOCUMENTS 7,999,161 B2 8/2011 Oraevsky et al.

OTHER PUBLICATIONS

Al Qaraghuli, Mohammed M et al. "Antibody-protein binding and conformational changes: identifying allosteric signalling pathways to engineer a better effector response." Scientific reports vol. 10,1 13696. Aug. 13, 2020, doi: 10.1038/s41598-020-70680-0 (Year: 2020).*
Rabia, Lilia A et al. "Understanding and overcoming trade-offs between antibody affinity, specificity, stability and solubility." Biochemical engineering journal vol. 137 (2018): 365-374. doi:10.1016/j.bej.2018.06.003 (Year: 2018).*
Poosarla, Venkata Giridhar et al. "Computational de novo design of antibodies binding to a peptide with high affinity." Biotechnology and bioengineering vol. 114,6 (2017): 1331-1342. doi:10.1002/bit. 26244 (Year: 2017).*

Lloyd, C et al. "Modelling the human immune response: performance of a 1011 human antibody repertoire against a broad panel of therapeutically relevant antigens." Protein engineering, design & selection : PEDS vol. 22,3 (2009): 159-68. doi: 10.1093/protein/gzn058 (Year: 2009).*
Khan, Tarique, and Dinakar M Salunke. "Adjustable locks and flexible keys: plasticity of epitope-paratope interactions in germline antibodies." Journal of immunology (Baltimore, Md. : 1950) vol. 192,11 (2014): 5398-405. doi:10.4049/jimmunol.1302143 (Year: 2014).*
Goel, Manisha et al. "Plasticity within the antigen-combining site may manifest as molecular mimicry in the humoral immune response." Journal of immunology (Baltimore, Md. : 1950) vol. 173, 12 (2004): 7358-67. doi:10.4049/jimmunol.173.12.7358 (Year: 2004).*
Edwards, Bryan M et al. "The remarkable flexibility of the human antibody repertoire; isolation of over one thousand different antibodies to a single protein, BLyS." Journal of molecular biology vol. 334, 1 (2003): 103-18. doi:10.1016/j.jmb.2003.09.054 (Year: 2003).*
Lu Zhang. Design of plasmonic nanoparticles and their use for biotoxin immunosensing. Organic chemistry. Sorbonne Université; Nanyang Technological University (Singapour), 2018. English. ffNNT : 2018SORUS439ff. fftel-02890626f (Year: 2018).*
Li, Y., Lee, JS. Recent developments in affinity-based selection of aptamers for binding disease-related protein targets. Chem. Pap. 73, 2637-2653 (2019). https://doi.org/10.1007/s11696-019-00842-6 (Year: 2019).*
Ogunyankin, Maria O et al. "Optimizing the NIR Fluence Threshold for Nanobubble Generation by Controlled Synthesis of 10-40 nm Hollow Gold Nanoshells." Advanced functional materials vol. 28, 10 (2018): 1705272. doi:10.1002/adfm.201705272 (Year: 2018).*
Akama et al., "Multiplexed homogeneous digital immunoassay based on single-particle motion analysis", Lab *Chip*, 20: 2113-2121, 2020.
Akama et al., Wash-and amplification-free digital immunoassay based on single-particle motion analysis, *ACS Nano.*, 13: 13116-13126, 2019.
Armbruster and Pry., "Limit of Blank, Limit of Detection and Limit of Quantitation", *Clin. Biochem. Rev.*, 29(Suppl 1), S49, 2008.
Arunrut et al., "Rapid and sensitive colorimetric detection of microsporidian *Enterocytozoon hepatopenaei* (EHP) based on spore wall protein (SWP) gene using loop-mediated isothermal amplification combined with DNA functionalized gold nanoparticles as probes",*Aquaculture*, 533: 736206, 2021.
Au et al., "A Comparative Study of Galvanic Replacement Reactions Involving Ag Nanocubes and AuCl2_ or AuCl4", *Adv. Mater.*, 20: 2517-2522, 2008.
Benjamin et al., Site Selective Nucleation and Size Control of Gold Nanoparticle Photothermal Antennae on the Pore Structures of a Virus. *Journal of the American Chemical Society*, 140 (49):17226-17233, 2018.
Bhalla et al., "Opportunities and Challenges for Biosensors and Nanoscale Analytical Tools for Pandemics: COVID-19", *ACS Nano*, 14: 7783, 2020.

(Continued)

*Primary Examiner* — Gregory S Emch
*Assistant Examiner* — McKenzie A Dunn

(57) ABSTRACT

The disclosure relates to particle-based assays for the detection of analytes. Using various combinations of particular technologies, including gold nanorods, silver nanoparticles, gold/silver nanoshells, gold/silver nanocages and nanobubble detection, enhanced detection limits can be achieved across a large range of analytes.

19 Claims, 32 Drawing Sheets
(32 of 32 Drawing Sheet(s) Filed in Color)

(56)  References Cited

OTHER PUBLICATIONS

Bokemann et al., "Point-of-care bulk testing for SARS-CoV-2 by combining hybridization capture with improved colorimetric LAMP", *Nat. Commun.*, 12: 1-8, 2021.

Bonar et al., "High sensitivity detection and sorting of infectious human immunodeficiency virus (HIV-1) particles by flow virometry", Virology, 505: 80-90, 2017.

Broughton et al., "CRISPR-Cas12-based detection of SARS-CoV-2", *Nat. Biotechnol.*, 38:870-874, 2020.

Cai et al., "Phosphorothioated Primers Lead to Loop-Mediated Isothermal Amplification at Low Temperatures", *Anal. Chem.* 90: 8290-8294, 2018.

Chang et al., "Single molecule enzyme-linked immunosorbent assays: theoretical considerations", *J. Immunol. Methods*, 378: 102-115, 2012.

Chen et al., "CRISPR-Cas12a target binding unleashes indiscriminate single-stranded DNase activity", *Science*, 360, 436-439, 2018.

Chen et al., "Quantitation of femtomolar-level protein biomarkers using a simple microbubbling digital assay and bright-field smartphone imaging", *Angew. Chem. Int. Ed.*, 58:13922-13928, 2019.

Cossarizza et al., "Guidelines for the use of flow cytometry and cell sorting in immunological studies", *Eur. J. Immunol.*, 47: 1584-1797, 2017.

Crannell et al., "Multiplexed Recombinase Polymerase Amplification Assay to Detect Intestinal Protozoa", *Anal. Chem.*, 88: 1610-1616., 2016.

Dai et al., "Polyethylene Glycol Backfilling Mitigates the Negative Impact of the Protein Corona on Nanoparticle Cell Targeting", *Angew Chem Int Ed Engl.*, 53:5093-5096, 2014.

De Albuquerque et al., "Digital protocol for chemical analysis at ultralow concentrations by surface-enhanced Raman scattering", *Anal. Chem.*, 90: 1248-1254, 2018.

Donato et al., "Evaluation of the Cue Health point-of-care COVID-19 (SARS-CoV-2 nucleic acid amplification) test at a community drive through collection center", *Diagn. Microbiol. Infect. Dis.*, 100, 115307, 2021.

Draz et al., "Applications of gold nanoparticles in virus detection", *Theranostics*, 8(7), 2018.

Driskell et al., "One-step assay for detecting influenza virus using dynamic light scattering and gold nanoparticles", *Analyst*, 136:3083-3090, 2011.

Du et al., "A Sweet Spot for Molecular Diagnostics: Coupling Isothermal Amplification and Strand Exchange Circuits to Glucometers", *Sci. Rep.*, 5: 11039, 2015.

Farka et al., "Advances in optical single-molecule detection: en route to supersensitive bioaffinity assays", *Angew. Chem. Int. Ed.*, 59:10746-10773, 2020.

Farka et al., "Single molecule upconversion-linked immunosorbent assay with extended dynamic range for the sensitive detection of diagnostic biomarkers", *Anal. Chem.*, 89:11825-11830, 2017.

Filbrunet et al., Chemical modification of antibodies enables the formation of stable antibody-gold nanoparticle conjugates for biosensing. Analyst, 142:4456, 2017.

Galanzha and Zharov., "Photoacoustic flow cytometry", *Methods*, 57: 280-296, 2012.

Gansen et al., "Digital LAMP in a sample self-digitization (SD) chip", *Lab on a chip*, 12(12):2247-2254, 2012.

Gao et al., "Template Regeneration in Galvanic Replacement: A Route to Highly Diverse Hollow Nanostructures", *ACS Nano*, 14: 791-801, 2020.

Genç et al., "Tuning the Plasmonic Response up: Hollow Cuboid Metal Nanostructures", ACS *Photonics*, 3: 770-779, 2016.

Godakhindi et al., "Tuning the Gold Nanoparticle Colorimetric Assay by Nanoparticle Size, Concentration, and Size Combinations for Oligonucleotide Detection", *ACS Sens.*, 2, 1627-1636, 2017.

Gootenberg et al., "Nucleic acid detection with CRISPR-Cas13a/C2c2", Science, 356: 438-442, 2017.

Hardinge et al., "Reduced False Positives and Improved Reporting of Loop-Mediated Isothermal Amplification using Quenched Fluorescent Primers", *Sci. Rep.*, 9: 1-13, 2019.

Hogan et al., "Comparison of the Accula SARS-CoV-2 Test with a Laboratory-Developed Assay for Detection of SARS-CoV-2 RNA in Clinical Nasopharyngeal Specimens", *J. Clin. Microbiol.*, 58, e01072-20, 2020.

Hohenester et al., MNPBEM—A Matlab toolbox for the simulation of plasmonic nanoparticles, *Comput. Phys. Commun.*, 183:370-381, 2012.

Hu et al., "Absolute quantification of H5-subtype avian influenza viruses using droplet digital loop-mediated isothermal amplification", *Anal. Chem.*, 89: 745-750, 2017.

Jolany Vangah et al., "CRISPR-Based Diagnosis of Infectious and Noninfectious Diseases", *Biol. Proced. Online*, 22:1-14, 2020.

Kaminski et al., "CRISPR-based diagnostics", *Nat. Biomed. Eng.*, 5:643-656, 2021.

Khambhati et al., "Current progress in CRISPR-based diagnostic platforms", J Cell *Biochem.*, 120(3): 2721-2725, 2019.

Khodakov et al., "Diagnostics based on nucleic acid sequence variant profiling: PCR, hybridization, and NGS approaches", *Adv. Drug Deliv. Rev.*, 105: 3-19, 2016.

Kim et al., "Large-scale femtoliter droplet array for digital counting of single biomolecules", *Lab Chip*, 12:4986-4991, 2012.

Kimling et al., "Turkevich method for gold nanoparticle synthesis revisited", *J. Phys. Chem B.*, 110: 15700-15707, 2006.

Koryakina et al., "Optically responsive delivery platforms: from the design considerations to biomedical applications", *Nanophotonics*, 2020.

Kumar et al., "3—Methods for characterization of nanoparticles", *Adv. Nanomed. Delivery Ther. Nucleic Acids*, 43-58, 2017.

Kumvongpin et al., "High sensitivity, loop-mediated isothermal amplification combined with colorimetric gold-nanoparticle probes for visual detection of high risk human papillomavirus genotypes 16 and 18", *J. Virol. Methods*, 234: 90-95, 2016.

Lapotko et al., "Optical excitation and detection of vapor bubbles around plasmonic nanoparticles", *Optics Express*, 17(4), 2009.

Levitz et al., "Distinct patterns of innate immune activation by clinical isolates of respiratory syncytial virus", *PLoS One*, 12: e0184318, 2017.

Li et al., "Rock the nucleus: significantly enhanced nuclear membrane permeability and gene transfection by plasmonic nanobubble induced nanomechanical transduction" *Chem. Commun.*, 54: 2479-2482 2018.

Lin et al., "Digital loop-mediated isothermal amplification on a commercial membrane", *ACS Sens.*, 4: 242-249, 2019.

Liu et al., "Point-of-care diagnosis of respiratory syncytial virus by digital nanobubble detection", *In 23rd International Conference on Miniaturized Systems for Chemistry and Life Sciences, MicroTAS*, 929-930, 2019.

Liu et al., "Colorimetric detection of influenza A virus using antibody-functionalized gold nanoparticles", *Analyst*, 140: 3989-3995, 2015.

Liu et al., "Digital duplex homogeneous immunoassay by counting immunocomplex labeled with quantum dots", *Anal. Chem.*, 93: 3089-3095 2021.

Liu et al., "Digital plasmonic nanobubble detection for rapid and ultrasensitive virus diagnostics", Zenodo, DOI: 10.5281/zenodo. 5708857, 2021.

Loiseau et al., Silver-Based Plasmonic Nanoparticles for and Their Use in Biosensing, *Biosensors*,9:78, 2019.

Lukianova-Hleb et al., "All-in-one processing of heterogeneous human cell grafts for gene and cell therapy", *Molecular therapy—Methods & clinical development*, 3:16012-16012, 2016.

Lukianova-Hleb et al., "Intraoperative diagnostics and elimination of residual microtumours with plasmonic nanobubbles", *Nat. Nanotechnol.*, 11: 525-532, 2016.

Lukianova-Hleb et al., "Laser Pulse Duration Is Critical for the Generation of Plasmonic Nanobubbles", *Langmuir*, 30 (25):7425-7434, 2014.

Lukianova-Hleb et al., "On-demand intracellular amplification of chemoradiation with cancer-specific plasmonic nanobubbles", *Nat. Med.*, 20:778-784, 2014.

(56) References Cited

OTHER PUBLICATIONS

Lukianova-Hleb et al., "Plasmonic Nanobubbles as Transient Vapor Nanobubbles Generated Around Plasmonic Nanoparticles", *ACS Nano.*, 4(4): 2109-2123, 2010.

Mahony et al., "Development of a sensitive loop-mediated isothermal amplification assay that provides specimen-to-result diagnosis of respiratory syncytial virus infection in 30 minutes", *J. Clin. Microbiol.*, 51: 2696-2701, 2013.

Mawatari et al., "Thermal lens detection device", *Lab Chip*, 11: 2990-2993, 2011.

Moitra et al., "Selective Naked-Eye Detection of SARS-CoV-2 Mediated by N Gene Targeted Antisense Oligonucleotide Capped Plasmonic Nanoparticles", *ACS Nano*,14(6): 7617-7627, 2020.

Nakatsuka et al., "Aptamer-field-effect transistors overcome Debye length limitations for small-molecule sensing", *Science*, 362: 319-324, 2018.

Notomi et al., "Loop-mediated isothermal amplification of DNA", *Nucleic Acids Res.*,28: e63, 2000.

Opota et al., Microbial diagnosis of bloodstream infection: towards molecular diagnosis directly from blood, *Clin. Microbiol Infect.*, 21: 323-331, 2015.

Qin et al., "Quantitative comparison of photothermal heat generation between gold nanospheres and nanorods", *Sci. Rep.*, 6: 29836, 2016.

Qin et al., "Thermophysical and biological responses of gold nanoparticle laser heating", *Chem. Soc. Rev.*, 41: 1191-1217, 2012.

Rioux et al., "An Analytic Model for the Dielectric Function of Au, Ag, and their Alloys", *Adv. Opt. Mater.*, 2: 176-182, 2014.

Rissin et al., "Simultaneous detection of single molecules and singulated ensembles of molecules enables immunoassays with broad dynamic range", Anal. Chem., 83: 2279-2285, 2011.

Rissin et al., "Single-molecule enzyme-linked immunosorbent assay detects serum proteins at subfemtomolar concentrations", *Nat. Biotechnol.*, 28: 595-599, 2010.

Roberts et al., "How restriction enzymes became the workhorses of molecular biology", *Proc. Natl. Acad. Sci. U.S.A.*, 102: 5905-5908, 2005.

Rodriguez-Manzano et al., "Reading Out Single-Molecule Digital RNA and DNA Isothermal Amplification in Nanoliter Volumes with Unmodified Camera Phones", *ACS Nano*, 10:3102-3113, 2016.

Rolando et al., "Real-time, digital LAMP with commercial microfluidic chips reveals the interplay of efficiency, speed, and background amplification as a function of reaction temperature and time", *Anal. Chem.*, 91:1034-1042, 2018.

Ruang-Areerate et al., "Development of loop-mediated isothermal amplification (LAMP) assay using SYBR safe and gold-nanoparticle probe for detection of *Leishmania* in HIV patients" *Sci. Rep.* 2021, 11, 1-11.

Safavieh et al., "Emerging Loop-Mediated Isothermal Amplification-Based Microchip and Microdevice Technologies for Nucleic Acid Detection", *ACS Biomater. Sci. Eng.*, 2: 278-294, 2016.

Sambrook et al., "Culinary Biology", *Cell*, 61:17-18, 1990.

Scotti et al., "End-point dilution and plaque assay methods for titration of cricket paralysis virus in cultured *Drosophila* cells", *J. Gen. Virol.*, 35: 393-396, 1977.

Seo et al., "Rapid Detection of COVID-19 Causative Virus (SARS-CoV-2) in Human Nasopharyngeal Swab Specimens Using Field-Effect Transistor-Based Biosensor", *ACS Nano*, 14: 5135-5142, 2020.

Sevenler et al., "Digital microarrays: single-molecule readout with interferometric detection of plasmonic nanorod labels", *ACS Nano*, 12: 5880-5887, 2018.

Shi et al., "Global, regional, and national disease burden estimates of acute lower respiratory infections due to respiratory syncytial virus in young children in 2015: a systematic review and modelling study", *Lancet*, 390: 946-958, 2017.

Shiju et al., "An insight into the photophysical and nonlinear optical properties of novel 1,3,4-oxadizole based donor-acceptor systems", *J. Mol. Liq.*, 348:118456, 2022.

Sidstedt et al., "Inhibition mechanisms of hemoglobin, immuno-globulin G, and whole blood in digital and real-time PCR", *Anal. Bioanal. Chem.*, 410: 2569-2583, 2018.

Sivakumar et al., "Ultraviolet-induced in situ gold nanoparticles for point-of-care testing of infectious diseases in loop-mediated isothermal amplification", *Lab Chip*, 21, 700-709, 2021.

Sriram et al., "A rapid readout for many single plasmonic nanoparticles using dark-field microscopy and digital color analysis," *Biosens. Bioelectron.*, 117: 530-536, 2018.

Suebsing et al., "Reverse transcription loop-mediated isothermal amplification (RT-LAMP) combined with colorimetric gold nanoparticle (AuNP) probe assay for visual detection of Penaeus vannamei nodavirus (PvNV)", *Lett. Appl. Microbiol.*, 56: 428-435, 2013.

Suwannin et al., "Heat-enhancing aggregation of gold nanoparticles combined with loop-mediated isothermal amplification (HAG-LAMP) for Plasmodium falciparum detection", *J. Pharm. Biomed. Anal.*, 203: 114178, 2021.

Tanner et al., "Visual detection of isothermal nucleic acid amplification using pH-sensitive dyes", *Biotechniques*,58: 59-68., 2015.

Thi et al., "A colorimetric RT-LAMP assay and LAMP-sequencing for detecting SARS-CoV-2 RNA in clinical samples", *Sci. Transl. Med.*, 12: eabc7075, 2020.

Tomita et al., "Loop-mediated isothermal amplification (LAMP) of gene sequences and simple visual detection of products", *Nat. Protoc.*, 3: 877-882, 2008.

Varona et al., "Visual Detection of Single-Nucleotide Polymorphisms Using Molecular Beacon Loop-Mediated Isothermal Amplification with Centrifuge-Free DNA Extraction", *Anal. Chem.*, 91: 6991-6995, 2019.

Verschoor et al., "An introduction to automated flow cytometry gating tools and their implementation", *Front. Immunol.*, 6:380, 2015.

Visser et al., "Continuous biomarker monitoring by particle mobility sensing with single molecule resolution", *Nat. Commun.*, 9: 2541, 2018.

Wan et al., "Quasi-spherical silver nanoparticles: Aqueous synthesis and size control by the seed-mediated Lee-Meisel method", *J. Colloid Interface Sci.*, 394: 263-268, 2013.

Wang et al., "A novel coronavirus outbreak of global health concern", *Lancet*, 395:470-473, 2020.

Wang et al., "Characterization of denaturation and renaturation of DNA for DNA hybridization", Toxicol. *Environ. Health. Sci.*, 29: e2014007, 2014.

Wang et al., "Peroxidase-AgAu hybrid nanocages as signal transducers for sensitive plasmonic colorimetric sensing", Xia, *J. Mater. Chem. C.*, 7:15179-15187, 2019.

Wang et al., "Two Methods for Increased Specificity and Sensitivity in Loop-Mediated Isothermal Amplification", *Molecules*, 20: 6048-6059, 2015.

Weiss et al., "Toward Nanotechnology-Enabled Approaches against the COVID-19 Pandemic", *ACS Nano*, 14: 6383-6406, 2020.

Wilson et al., "The Simoa HD-1 analyzer: a novel fully automated digital immunoassay analyzer with single-molecule sensitivity and multiplexing", *J. Lab. Autom.*, 21:533-547, 2016.

Wong et al., "Ultrasensitive and Closed-Tube Colorimetric Loop-Mediated sothermal Amplification Assay Using Carboxyl-Modified Gold Nanoparticles", *Small*, 10:1495-1499, 2014.

Wu et al., "Development and preliminary clinical validation of a high sensitivity assay for cardiac troponin using a capillary flow (single molecule) fluorescence detector", *Clin. Chem.* 52: 2157-2159, 2006.

Wu et al., "How nanoparticles transform single molecule measurements into quantitative sensors", *Adv. Mater*, 32: e1904339, 2020.

Wu et al., "Ultrasensitive detection of attomolar protein concentrations by dropcast single molecule assays", *J. Am. Chem. Soc.*, 142: 12314-12323 2020.

Xia et al., "25th Anniversary Article: Galvanic Replacement: A Simple and Versatile Route to Hollow Nanostructures with Tunable and Well-Controlled Properties", *Adv. Mater.*, 25: 6313-6333, 2013.

Xiao et al., "Enzyme-linked immunosorbent assay (ELISA) and blocking with bovine serum albumin (BSA)—not all BSAs are alike", *J. Immunol. Methods*, 384:148-151, 2012.

(56) References Cited

OTHER PUBLICATIONS

Xiong et al., "Near-infrared light triggered-release in deep brain regions using ultra-photosensitive nanovesicles", *Angew. Chem. Int. Ed.*, 59: 8608-8615, 2020.

Ye et al., "Ru Nanoframes with an fcc Structure and Enhanced Catalytic Properties", *Nano Lett.*, 16: 2812-2817, 2016.

Yelleswarapu et al., "Mobile platform for rapid sub-picogram-per-milliliter, multiplexed, digital droplet detection of proteins", *Proc. Natl. Acad. Sci. U.S.A.*, 116: 4489-4495, 2019.

Zhang et al., "Plasmonic scattering imaging of single proteins and binding kinetics", *Nat. Methods*, 17:1010-1017, 2020.

Zhou et al., "A CRISPR-Cas9-triggered strand displacement amplification method for ultrasensitive DNA detection", Nat. *Commun.*, 9: 1-11, 2018.

Zhou et al., "A sequence-specific plasmonic loop-mediated isothermal amplification assay with orthogonal color readouts enabled by CRISPR Cas12a", *Chem. Commun.*, 56: 3536-3538, 2020.

Zhu et al., "Local dielectric environment-dependent plasmonic optical sensitivity of gold nanocage: from nanobox to nanoframe", *Appl. Phys. A.*, 125: 1-11, 2019.

* cited by examiner

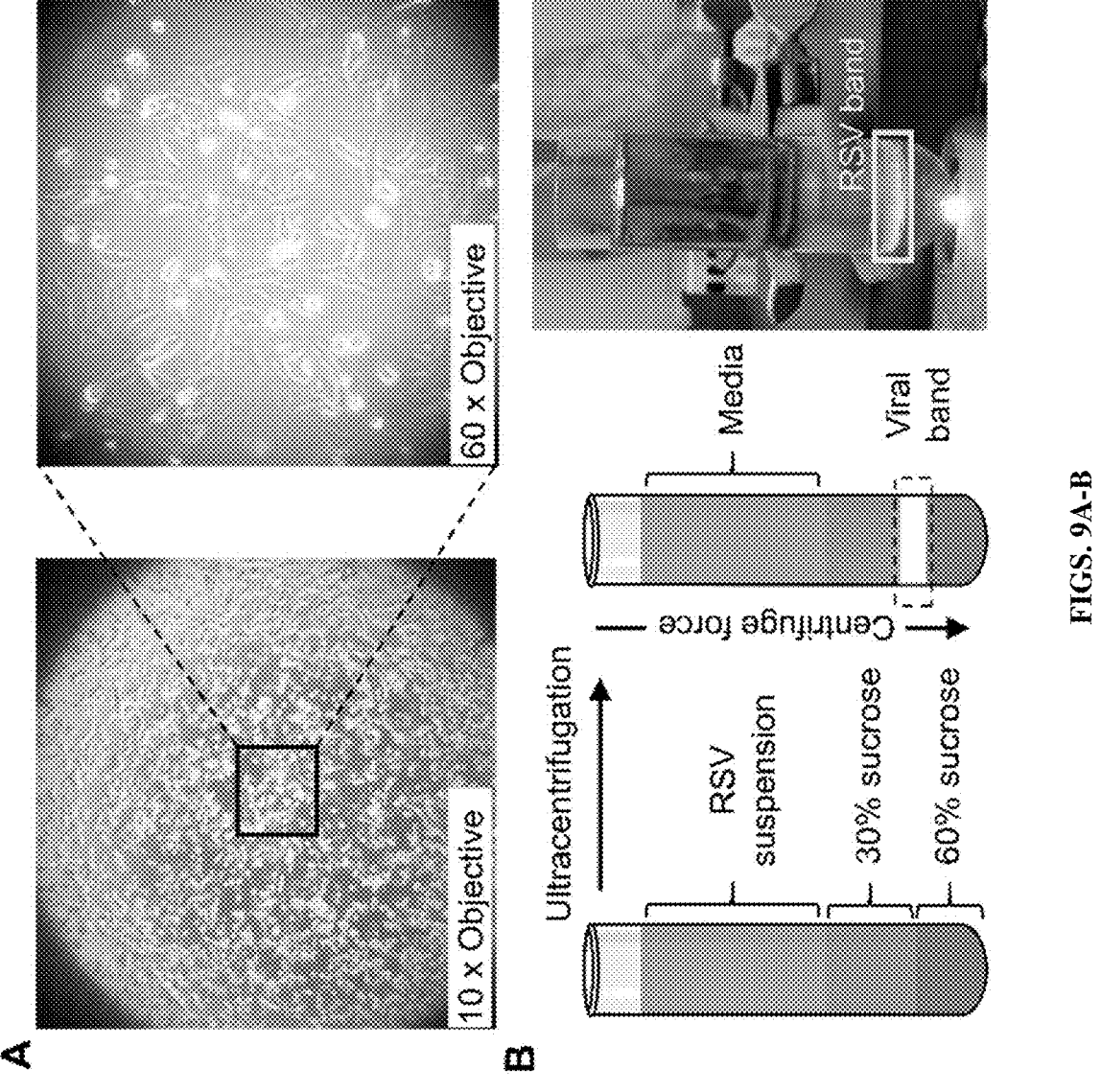
FIGS. 9A-B

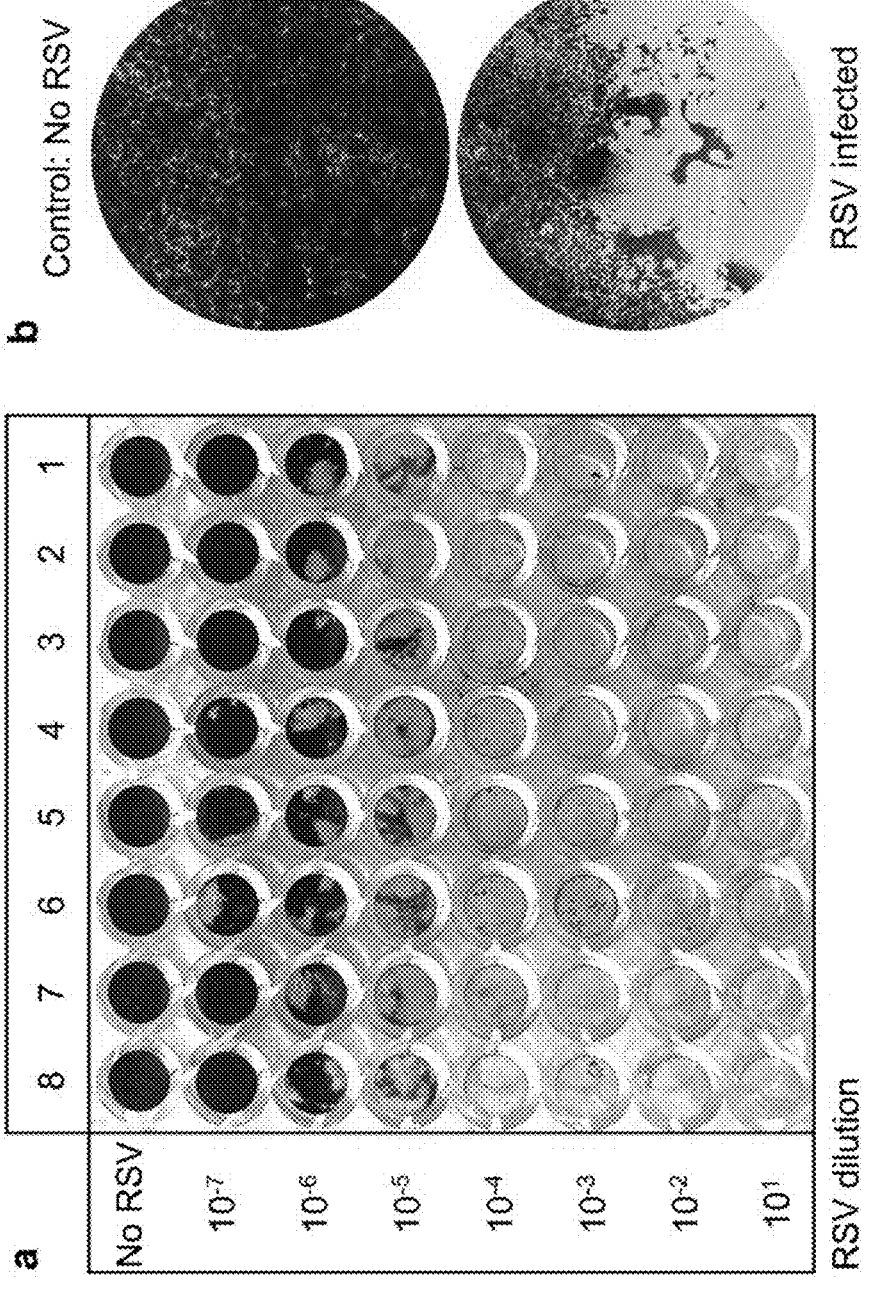
FIGS. 10A-B

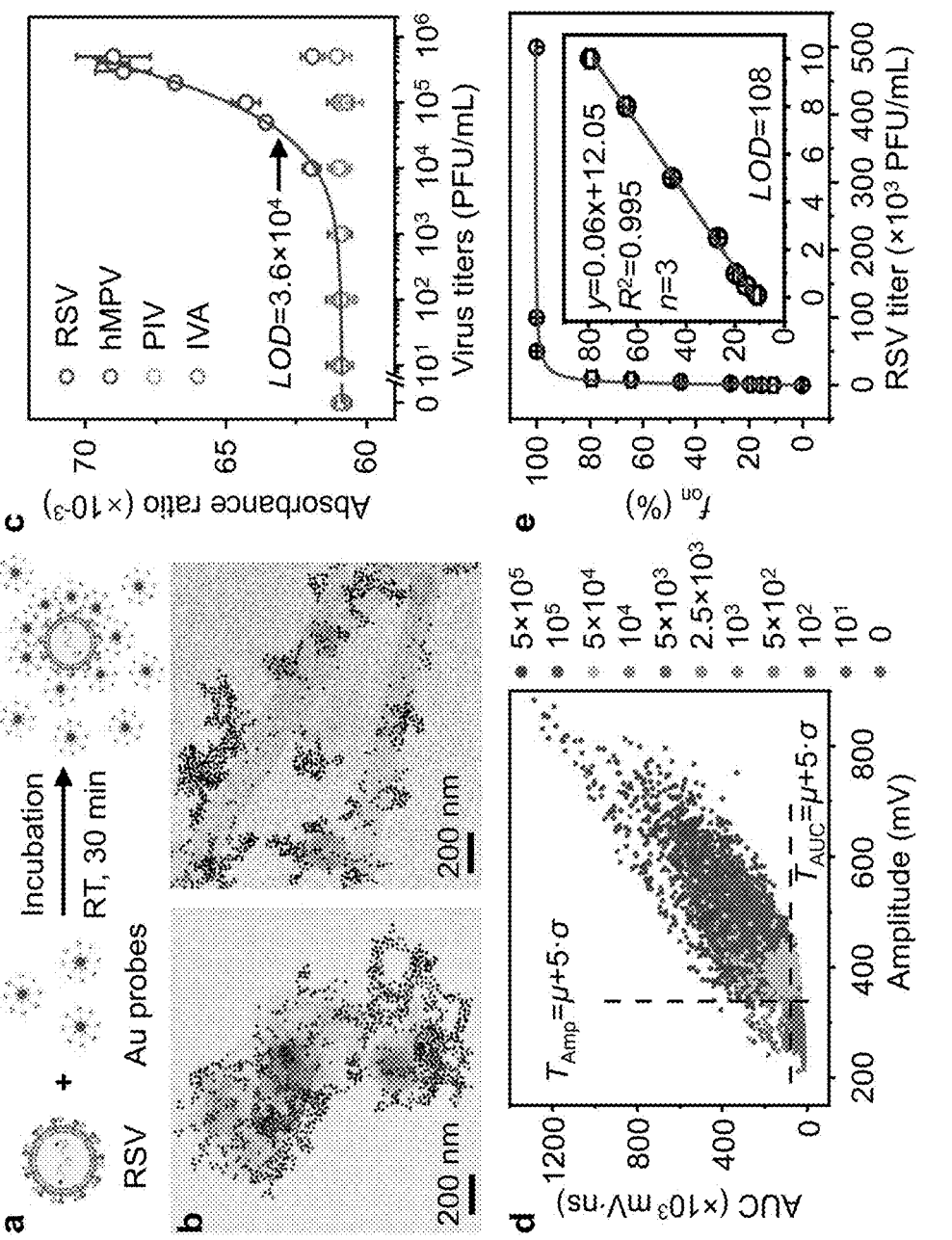
FIGS. 11A-E

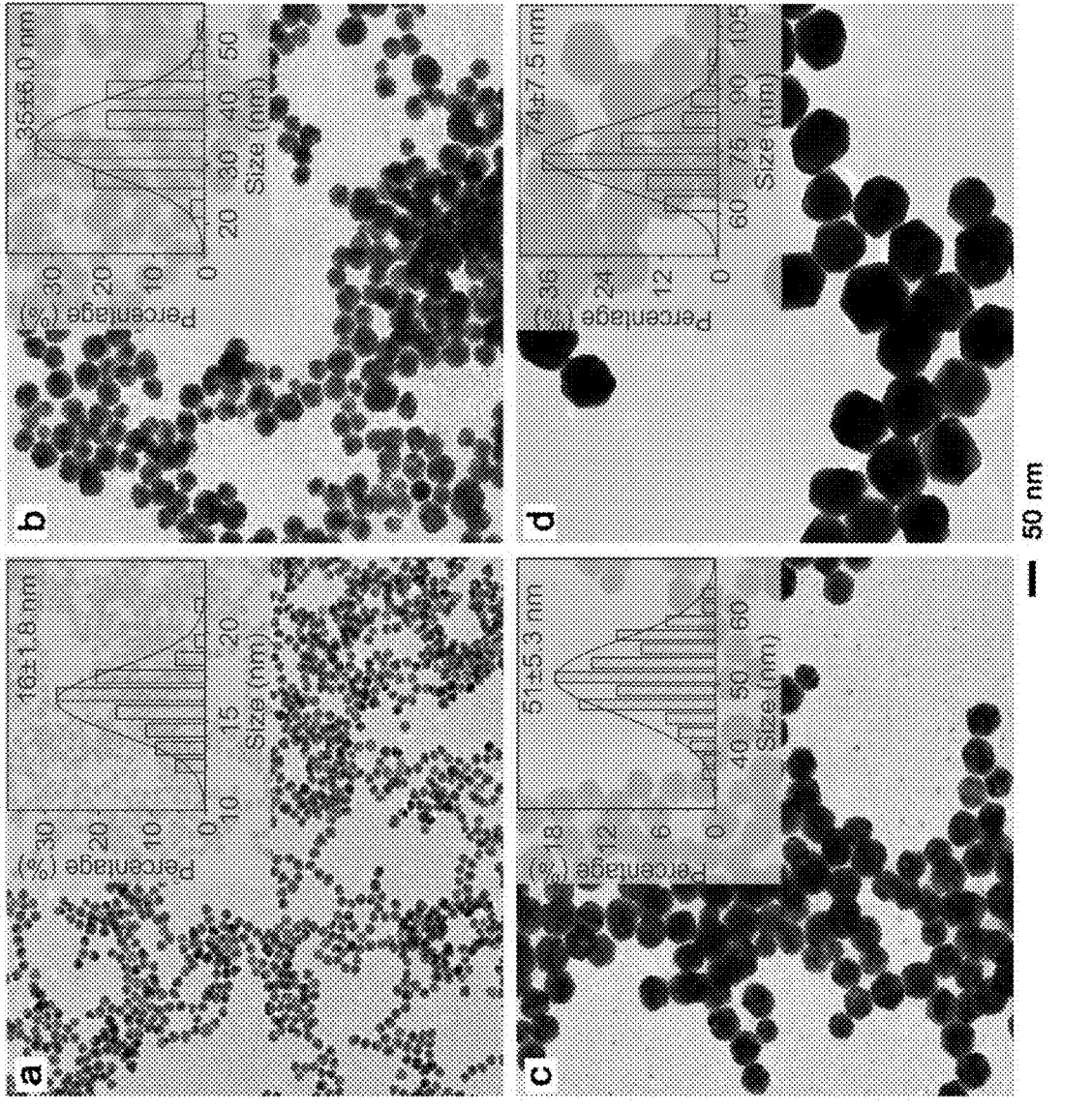
FIGS. 12A-D

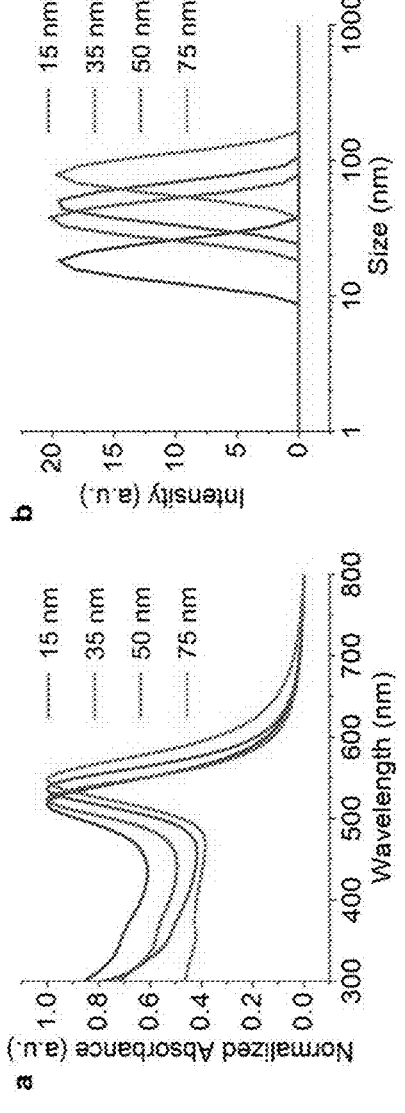
FIGS. 13A-B
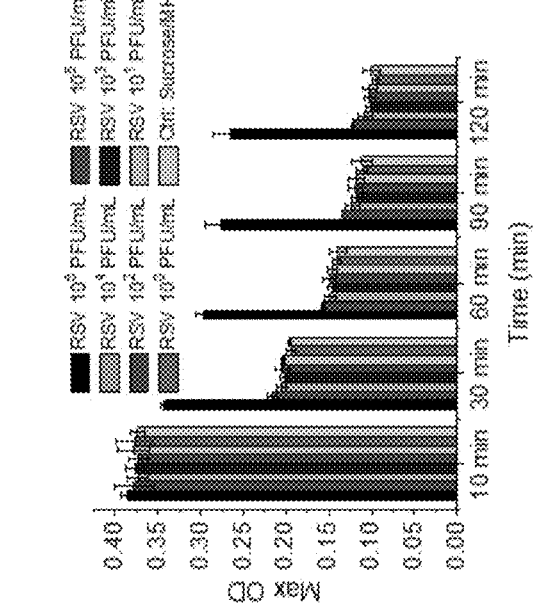
FIG. 14

FIGS. 15A-B

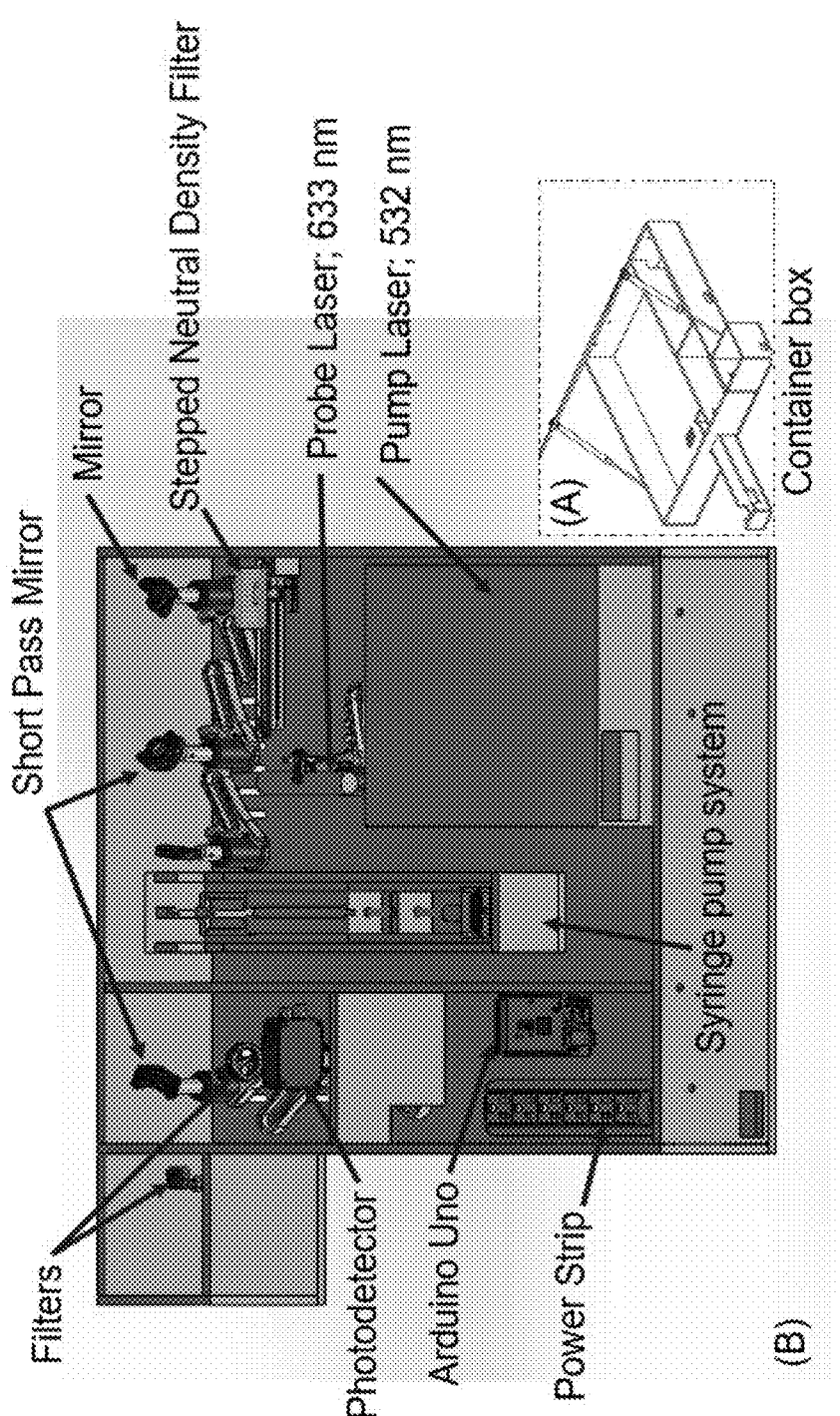
FIGS. 18A-B

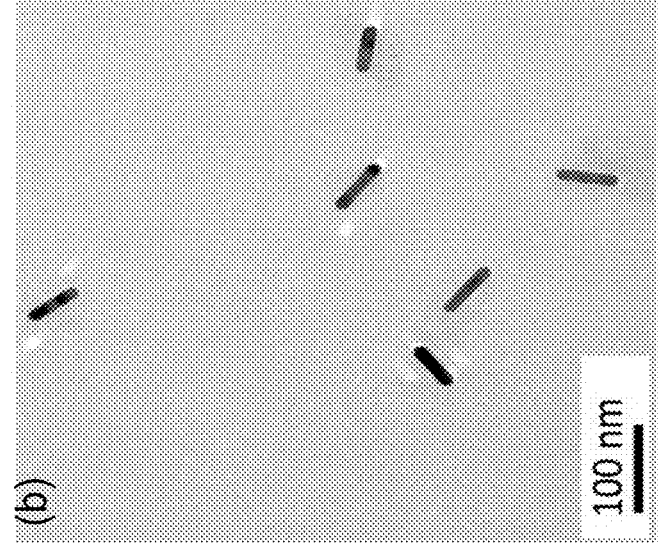
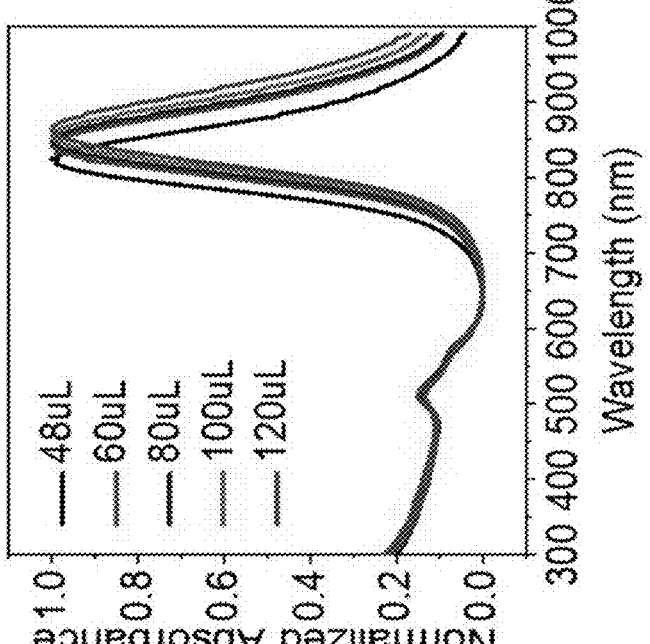
FIGS. 19A-B

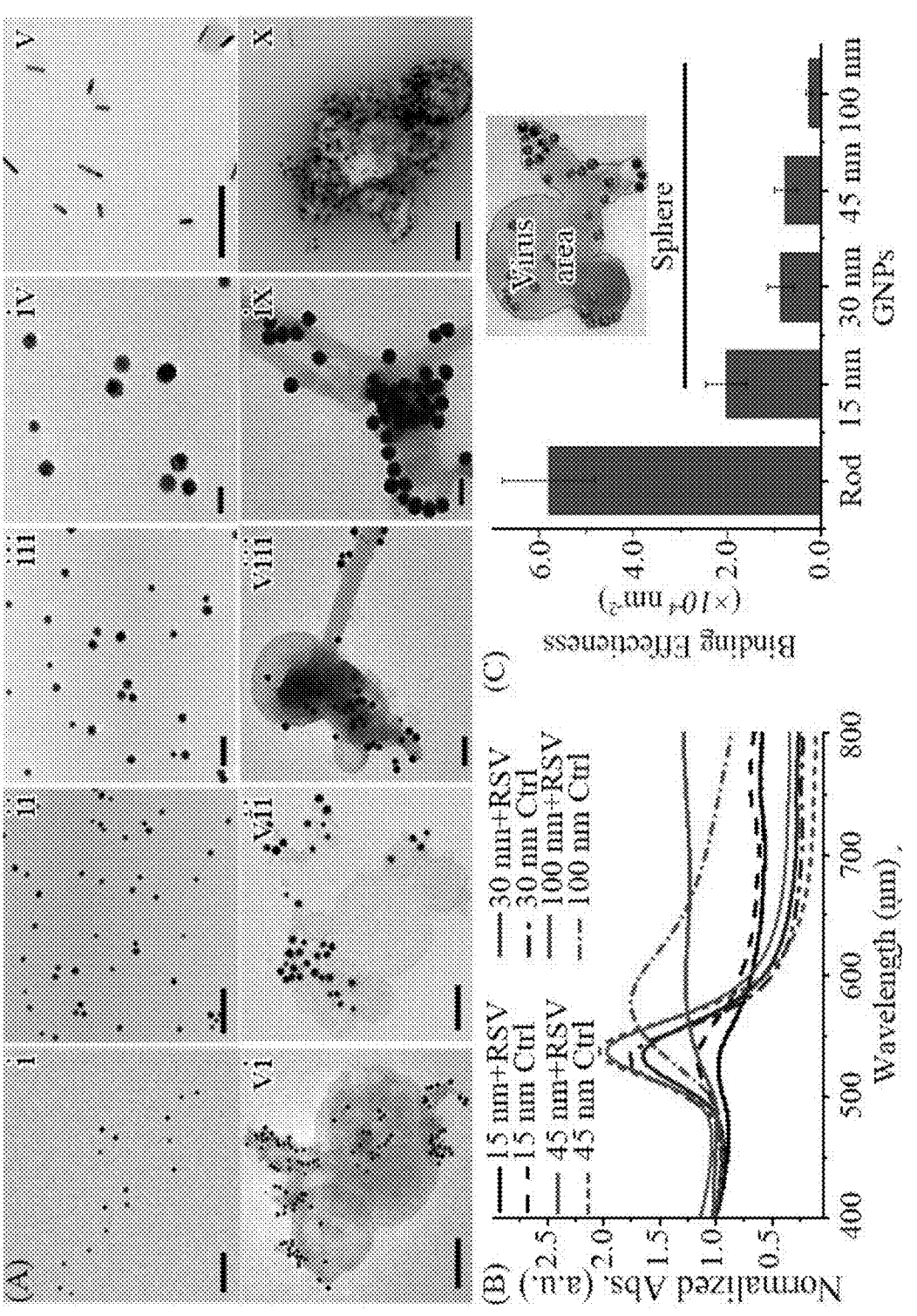
FIGS. 20A-C

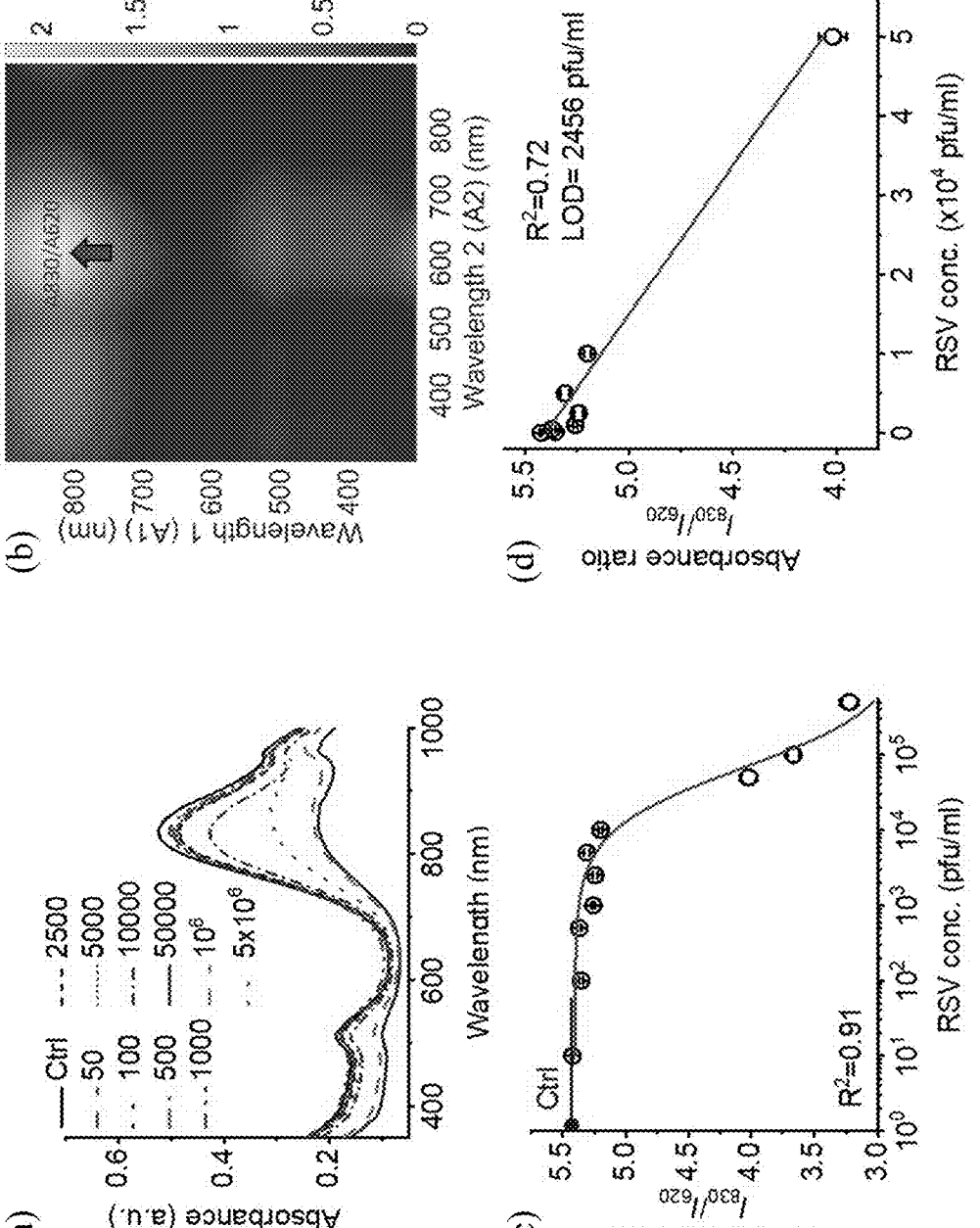
FIGS. 21A-D

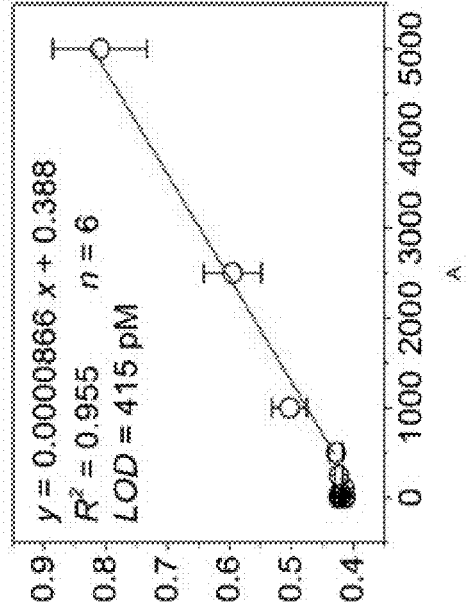
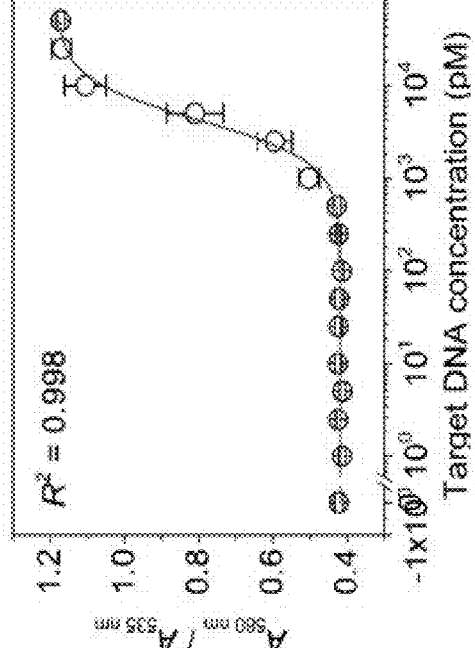
FIG. 34

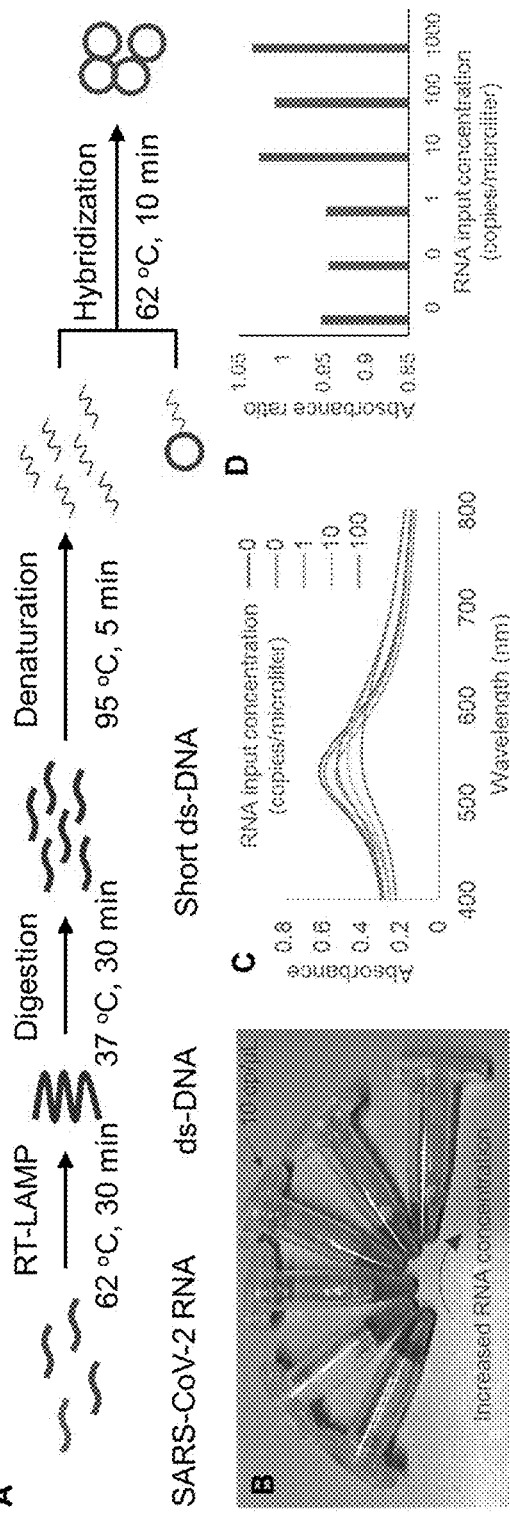
FIGS. 35A-D

PARTICLE-BASED SENSORS AND METHODS USING PARTICLE-BASED SENSORS FOR DETECTION OF ANALYTES

PRIORITY CLAIM

This application claims benefit of priority to U.S. Provisional Application Ser. No. 63/044,267, filed Jun. 25, 2020, the entire contents of each which is hereby incorporated by reference.

STATEMENT REGARDING FEDERALLY-SPONSORED RESEARCH OR DEVELOPMENT

This invention was made with government support under Grant Nos. R21 AI140462 and R01 AI151374 awarded by the National Institutes of Health. The government has certain rights in the invention.

BACKGROUND

The ability to rapidly detect diseases with high sensitivity is of paramount importance as evidenced by the current COVID-19 pandemic. Colorimetric homogeneous assays are simple, rapid, and one-step detection methods that do not require immobilizing, separating, or washing reagents, and are therefore promising for point-of-care (POC) diagnostic applications. For example, colorimetric homogeneous assays utilizing plasmonic gold nanoparticles (AuNPs) have been widely used in chemical and biological detection for proteins, nucleic acids, and virus particles. Due to their localized surface plasmon resonance and coupling, AuNPs provide intense color signals in the visible wavelengths that can be conveniently read out by the naked eye. However, the detection performance of colorimetric and other ensemble measurements has been largely limited by the extinction coefficient of AuNPs, large detection volume (i.e., $\mu L$ and mL), and high background signal. Therefore, they are not currently widely used as standalone diagnostic platforms.

To overcome this limitation, high resolution methods such as single-particle detection techniques have emerged for ultrasensitive homogeneous assays. Several methods including single-particle inductively coupled plasma mass spectroscopy, photothermal lens microscopy, Brownian motion-based counting, and dark-field microscopy have demonstrated their capability of imaging or counting individual particles. As a result, they revealed the potential to turn the homogeneous assay into a highly sensitive platform by reducing the background signals in ensemble measurements. However, the additional labeling and bulky instruments inevitably limits their applications in POC settings. Instead, engineering plasmonic nanoparticles with superior optical response is a simple yet efficient approach for the development of biosensors, in order to achieve highly sensitive assays.

On the other hand, digital assays have been a remarkable conceptual advance over the past two decades due to their capability of single-molecule detection and absolute quantification. They partition the analytes into microwells or emulsion droplets as small compartments for independent signal amplification and digital counting, leading to the sensitivity enhancement by up to $10^3$-fold over the conventional assays (i.e., enzyme-linked immunosorbent assay and polymerase chain reaction). Despite these advantages, digital assays have suffered from complex assay operations. Such paradigms prompt further innovations that develop various digital sensing platforms based on micro/nanoparticles. With its capability of examining individual particles' changes upon recognizing target molecules, single-particle detection holds great potential to simplify digital assays. Examples of single-particle digital assays include bright/dark-field imaging, interferometric or fluorescent imaging, surface-enhanced Raman scattering, surface plasmon resonance microscopy imaging, and particle mobility tracking. However, current techniques rely on cumbersome particle purification and advanced imaging that inevitably limit their widespread use. In this regard, implementing the digital concept in a homogeneous assay featuring is of great interest, which holds a promising potential as a rapid and ultrasensitive diagnostic platform.

SUMMARY

Thus, the disclosure provides plasmonic biosensors made of gold nanorods, silver nanoparticles, gold-silver nanocages, and gold-silver nanoshells for the colorimetric assay with enhanced detection sensitivity and a single-nanoparticle detection technique based on laser-nanoparticle interaction for a digital homogeneous assay.

In one embodiment, there is provided a method of detecting an analyte in a sample comprising (a) providing a binding agent comprising noble metal nanorod, nanobypiramid or nanoshell and an antibody or analyte-binding fragment thereof that selectively binds to an analyte, wherein said antibody or analyte-binding fragment thereof is linked to said noble metal nanorod, nanobypiramid or nanoshell with a 3,3'-dithiobis(sulfosuccinimidyl propionate) cross-linker (DTSSP); (b) contacting said binding agent with a sample containing or suspected of containing said analyte; and (c) detecting binding of said binding agent to said analyte by optical detection of binding. The detecting maybe quantitative or semi-quantitative or non-quantitative. The noble metal nanorod may be about 15 nm×about 50 nm.

The analyte may be a protein, peptide, oligonucleotide, polynucleotide, a lipid, or a carbohydrate, a virus, a bacterium, a fungus, or a cell, such as a cancer cell, a non-biological chemical compound such as a small molecule drug, a pesticide, a herbicide, a polymer, a toxin, an industrial by-product or waste product, or a metal (e.g., heavy metal ion). In particular, the analyte may be respiratory syncytial virus (RSV) or SARS-COV-2, such as where the limit of detection of said RSV is about $2\times10^3$ PFU/mL. The antibody may be a single chain antibody, bispecific antibody, or a polyvalent antibody, and the antigen binding fragment may be a Fab, a $F(ab)_2$, a scFv or aptamer.

The method may further comprise a control reaction where said binding agent is contacted with a second sample containing said analyte, optionally wherein the amount of said analyte in said second sample is known and/or a control reaction where said binding agent is contacted with a second sample lacking said analyte. Steps (b) and (c) may be completed in less than one hour, such as about 30-60 minutes, or about 30 minutes. Step (c) may comprise spectrophotometry, such as UV-Vis spectroscopy. Step (c) may comprise visual detection by the unaided human eye, such as by color change. Step (c) employs a handheld optical detection device.

The sample may be a biological sample (fluid sample, tissue sample), an environmental sample, a food sample, or a drug sample. The noble metal nanorod, nanobypiramid or nanoshell may be a gold nanorod, nanobypiramid or nanoshell. The noble metal nanorod, nanobypiramid or nanoshell may be silver, gold-silver alloy, gold-silver core-shell or silver-gold core-shell.

In another embodiment, there is provided a method of detecting an analyte in a sample comprising (a) providing a binding agent comprising a gold particle an antibody or analyte-binding fragment thereof that selectively binds to an analyte, wherein said antibody or analyte-binding fragment thereof is linked to said gold nanoparticle; (b) contacting said binding agent with a sample containing or suspected of containing said analyte, wherein binding of said binding agent to said analyte induces nanoparticle aggregation; (c) subjecting the product of step (b) to a laser, thereby inducing nanobubbles when nanoparticle aggregates are present; and (d) detecting binding of said binding agent to said analyte by optical detection of nanobubbles.

The method may be quantitative or semi-quantitative or non-quantitative. The analyte may be a protein, peptide, oligonucleotide, polynucleotide, a lipid, or a carbohydrate, a virus, a bacterium, a fungus, or a cell, such as a cancer cell, a non-biological chemical compound such as a small molecule drug, a pesticide, a herbicide, a polymer, a toxin, an industrial by-product or waste product, or a metal ion (e.g., heavy metal ion). In particular, the analyte may be respiratory syncytial virus (RSV) or SARS-COV-2, such as where the limit of detection of said RSV is about $10^2$ PFU/mL. The antibody may be a single chain antibody, bispecific antibody, or a polyvalent antibody and the antigen binding fragment may be a Fab, a $F(ab)_2$, a scFv or aptamer. The sample may be a biological sample (fluid sample, tissue sample), an environmental sample, a food sample, or a drug sample.

The method may further comprise a control reaction where said binding agent is contacted with a second sample containing said analyte, optionally wherein the amount of said analyte in said second sample is known, and/or a control reaction where said binding agent is contacted with a second sample lacking said analyte. Steps (b) and (c) may be completed in less than one hour, such as about 30-60 minutes, or about 30 minutes. Step (c) may comprise optically detecting a light frequency, light magnitude, life time (peak width), change in the magnitude (peak intensity), and/or area under the curve (peak area). The laser may be nanosecond or picosecond laser. Step (d) may employ a handheld optical detection device.

In a further embodiment, there is provided a method of detecting a oligo- or polynucleotide of interest in a sample comprising (a) providing a binding agent comprising (i) a silver nanoparticle, a gold/silver alloy nanoshell, or a gold/silver alloy nanocage and (ii) a first nucleic acid probe that selectively binds to a target oligo- or polynucleotide; (b) contacting said binding agent with a sample containing or suspected of containing said oligo- or polynucleotide; and (c) detecting binding of said binding agent to said oligo- or polynucleotide by optical detection of binding. The may be quantitative, semi-quantitative or non-quantitative. The sample may be suspected of containing an oligonucleotide of interest or a polynucleotide (such as an RNA) of interest. The sample may be a biological sample (fluid sample, tissue sample), an environmental sample, a food sample, or a drug sample. The binding agent may comprise a second nucleic acid probe for the same target oligo- or polynucleotide, such as where said first and second probes constitute a primer pair capable of priming amplification of said target oligo- or polynucleotide. The binding agent may comprise a second nucleic acid probe for a distinct target oligo- or polynucleotide.

The method may further comprise a control reaction where said binding agent is contacted with a second sample containing said target oligo- or polynucleotide, optionally wherein the amount of said target oligo- or polynucleotide in said second sample is known, and/or a control reaction where said binding agent is contacted with a second sample lacking said target oligo- or polynucleotide. Steps (b) and (c) may be completed in less than one hour, such as about 30-60 minutes, or about 30 minutes. Step (c) may comprise spectrophotometry, such as UV-Vis spectroscopy, visual detection by the unaided human eye, such as by color change, and or with a light microscope. Step (c) may comprise amplification of said target oligo- or polynucleotide. The limit of detection may be about 4 μM and single molecule (aM) detection with amplification. Step (c) may comprise colorimetric detection and/or use of a handheld optical detection device.

The method may further comprise isothermal amplification such as loop-mediated isothermal amplification, recombinase polymerase amplification, or rolling circle amplification, or may comprises reverse-mediated isothermal amplification such as reverse-mediated loop-mediated isothermal amplification, reverse-mediated recombinase polymerase amplification, or reverse-mediated rolling circle amplification. The method may further comprise restriction enzyme digestion and/or denaturation of double-strand DNA into single-strand DNA, such as by heating, enzyme digestion, or chemical degradation.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

(FIG. 1A) The plasmonic nanobubbles (PNBs) generation and detection in flow. The gold nanoparticles (AuNPs) as labels are used for the generation of the PNBs by short laser pulses and subsequently detected by a secondary probe laser due to the amplified optical absorption. (FIG. 1B) The detection principle based on optofluidic scanning of a sample flowing through the micro-capillary. The "on" and "off" refer to the positive and negative PNB signals representing for the presence or absence of targets.

Figure 2:
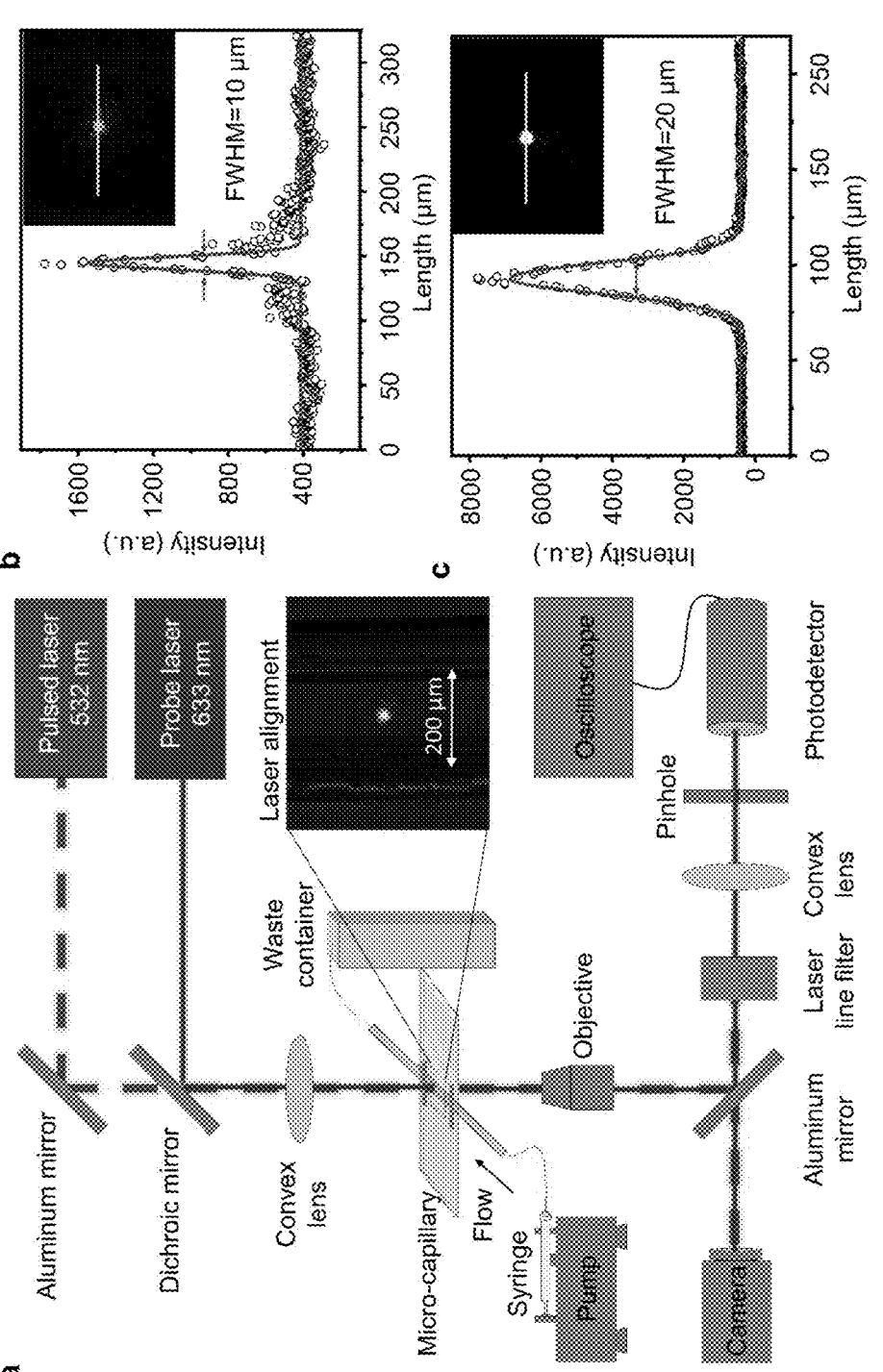

FIGS. 2A-C. The schematics illustration of digital plasmonic nanobubble detection apparatus and laser beam characterization. (FIG. 2A) Schematics illustration of the experimental setup. Energy profiles of (FIG. 2B) pump and (FIG. 2C) probe lasers. The scatters were normal distribution fitted, where the full width at half maximum (FWHM) was used as beam diameters.

Figure 3:
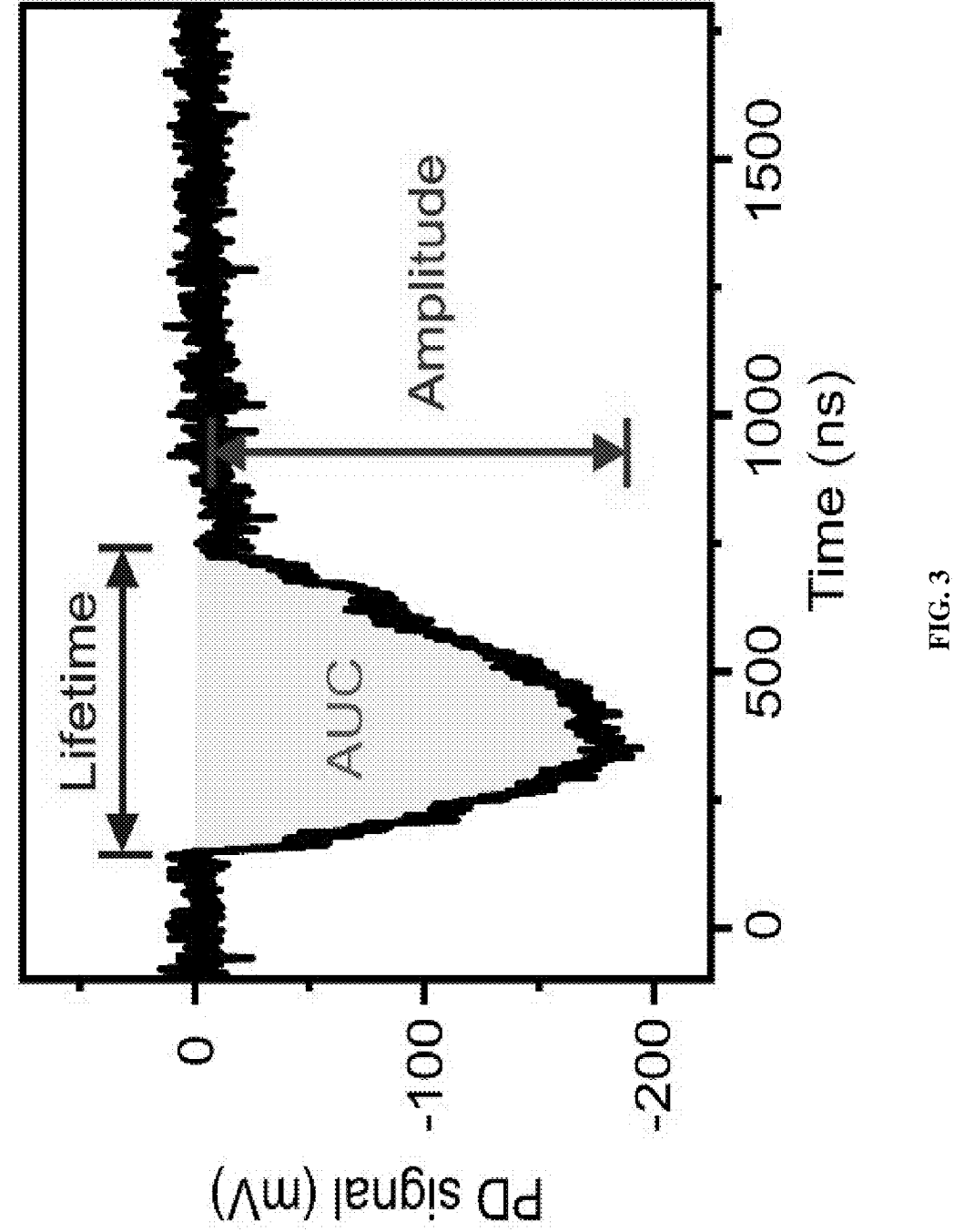
Figure 4:
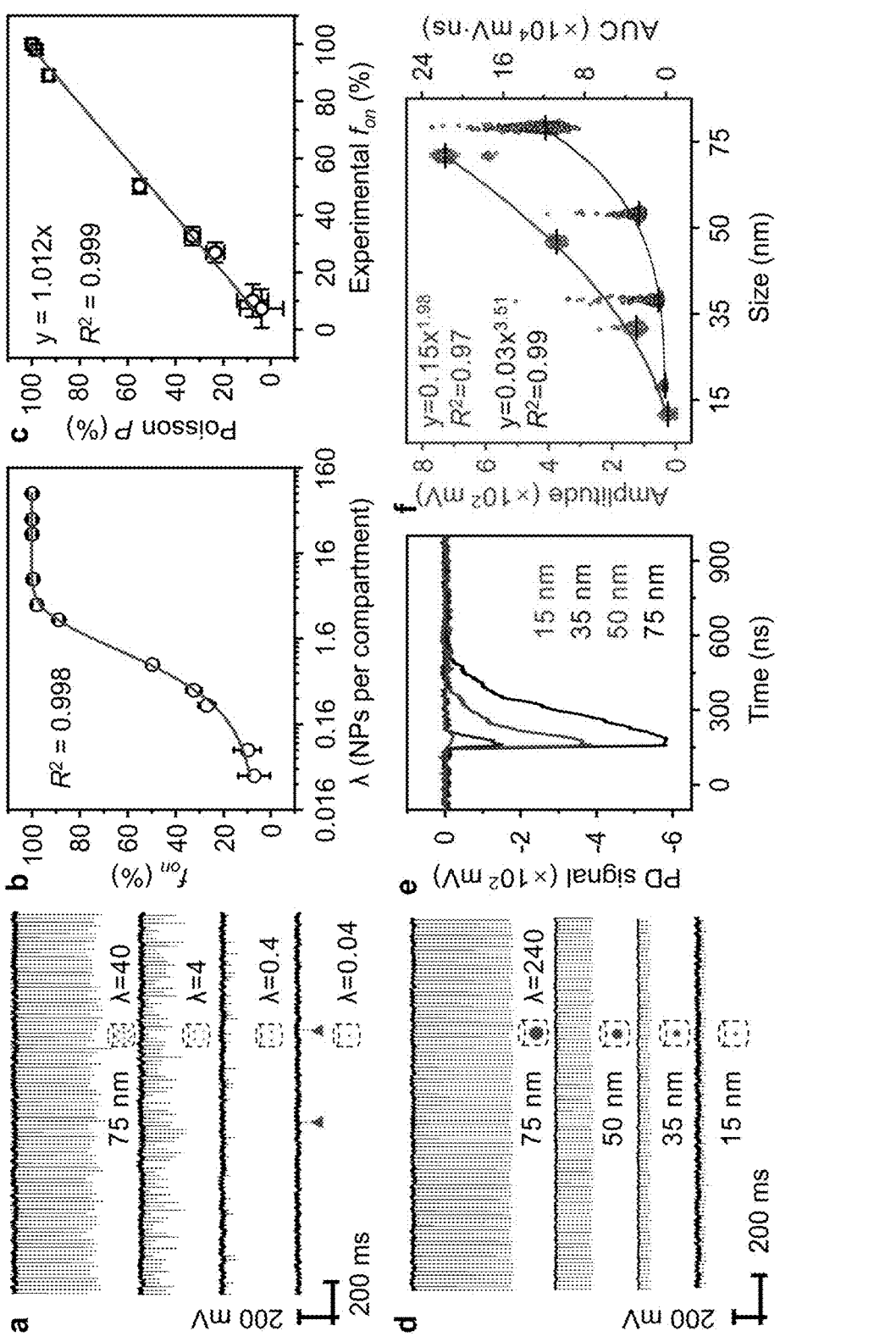

FIG. 3. Schematic illustration of a typical PNB signal recorded by a photodetector (PD). The signal includes the amplitude (peak intensity), lifetime (peak width), and area-under-curve (AUC, peak area). AUC is the integral value of amplitude along the lifetime. In the present work, only values of amplitude and AUC were used as indexes.

FIGS. 4A-F. Detection of single AuNPs and differentiation of NP size by DIAMOND. (FIG. 4A) Representative PNB signal traces (100 pulses) for 75 nm AuNP suspensions with different particle concentrations. Schematics represent the decreased number ($\lambda$) of AuNPs per detection. Red triangles mark the positive PNB signals. (FIG. 4B) Quantification of AuNP concentrations by plotting the frequency count ($f_{on}$) against $\lambda$. (FIG. 4C) Correlation between experimental $f_{on}$ and the theoretical probability (P) based on Poisson statistics. (FIG. 4D) Representative PNB signals traces (100 pulses) for AuNP suspensions with different sizes. Schematics represent the increasing AuNP sizes and same AuNP number per detection. (FIG. 4E) Single PNB signals extracted from (FIG. 4-d). PD is photodetector. (FIG. 4F) Correlations between the amplitude and AUC of PNB signals as a function of AuNP size. Black lines denote the statistical average values.

Figure 5:
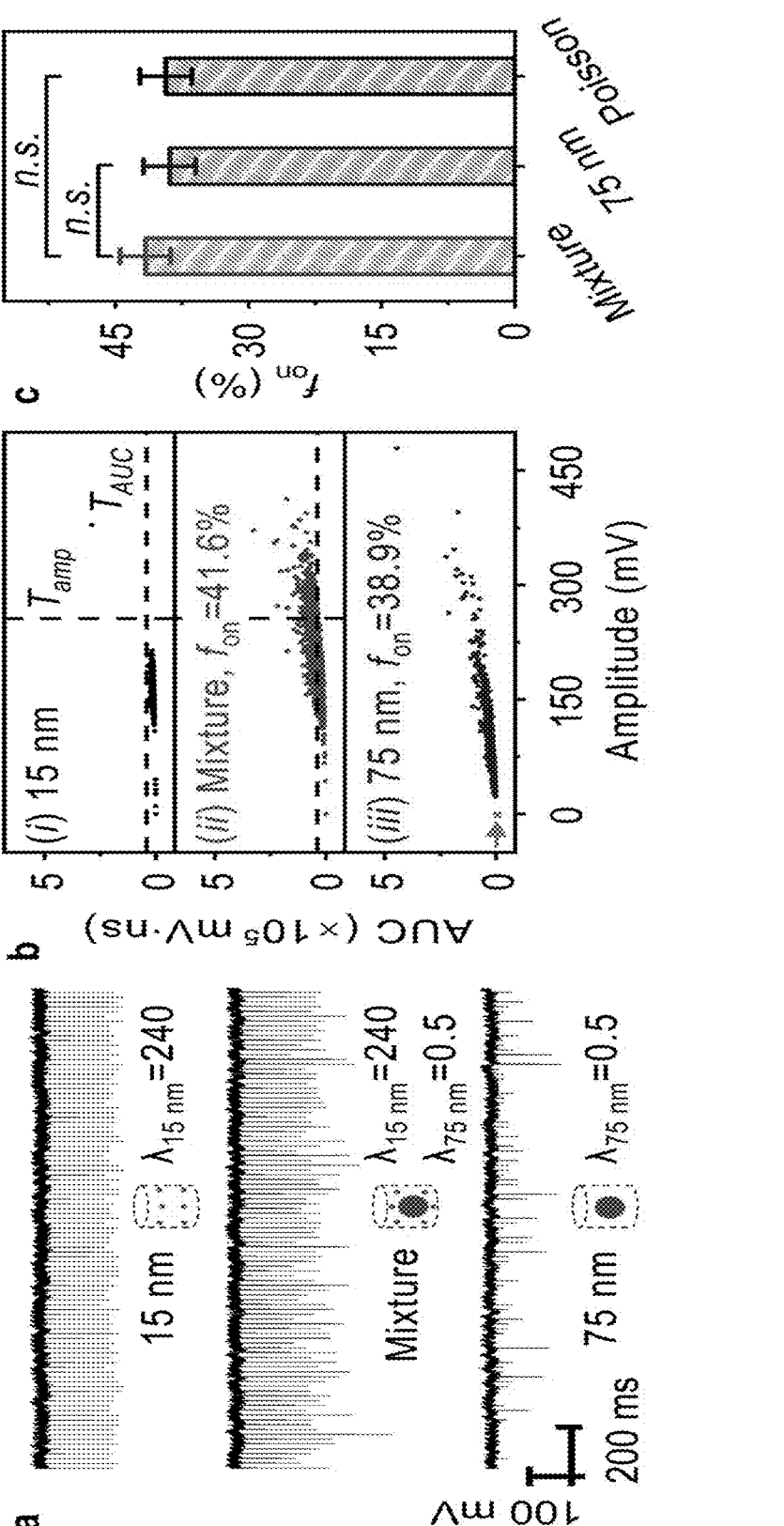
Figure 6:
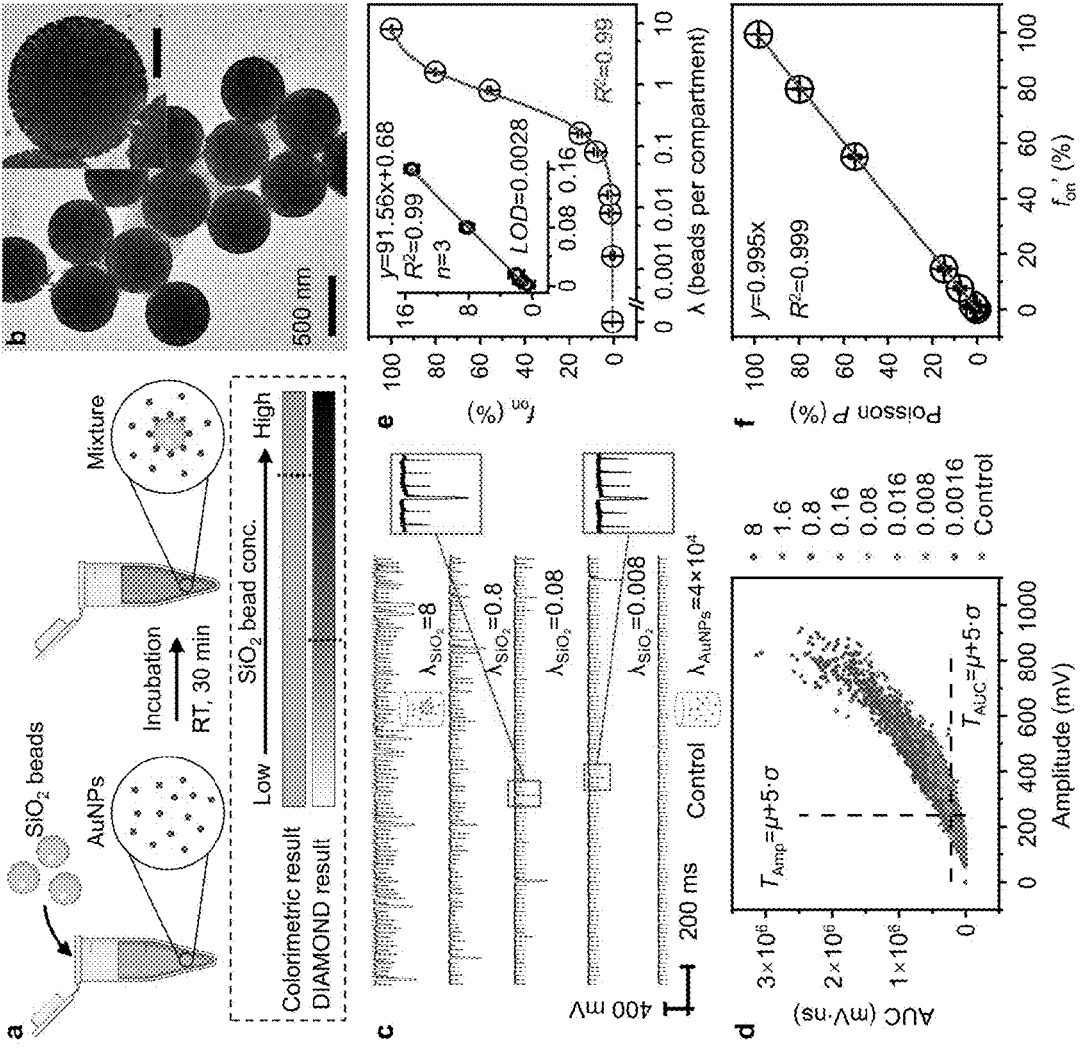

FIGS. 5A-C. Identification of heterogeneity by DIAMOND. (FIG. 5A) Representative PNB signals traces (100 pulses) for 15 nm and 75 nm AuNPs and their mixture. Schematics represent the sample information. (FIG. 5B) Bivariate plots of amplitude and AUC extracted from 3,000 pulses for the three samples in FIG. 5A. The dashed lines in cases (i) and (ii) indicate the same thresholds of amplitude ($T_{amp}$) and AUC ($T_{AUC}$). The red arrow in case (iii) highlights scatters at 0. (FIG. 5C) Bar plot of experimental frequencies ($f_{on}$) as determined in FIG. 5B for cases (ii) and (iii) and theoretical probability predicted by Poisson statistics. n.s. stands for no significant difference (p-value>0.05). The error bars for experimental $f_{on}$ indicate the standard deviations of three independent measurements and for theory, it is the Poisson noise-associated coefficient of variation, where N is the number of counted "on" signals.

FIGS. 6A-F. Detection of SiO$_2$ beads in a homogeneous assay by DIAMOND. (FIG. 6A) Schematic of a homogeneous assay of SiO$_2$ beads by AuNPs as a pair of targets and probes at room temperature (RT). Lower panel shows that when bead concentrations are insufficient to induce the color change, DIAMOND can detect the PNB signals. (FIG. 6B) TEM image of SiO$_2$-AuNPs conjugates. Scale bar in inset is 200 nm. (FIG. 6C) Representative PNB signal traces (100 pulses) for the assay solutions. Schematics represent the assay information that show the different $\lambda$ of SiO$_2$ beads and the same $\lambda$ of AuNPs. (FIG. 6D) Bivariate plot of amplitude and AUC extracted from 3,000 pulses for the assay solutions with different $\lambda$ of SiO$_2$ beads. Dashed lines indicate the positions of thresholds calculated from the control sample. (FIG. 6E) Quantification of SiO$_2$ bead concentration as a function of frequency counting ($f_{on}$). Error bars indicate the standard deviations of three independent measurements, and the LOD was calculated as 3 standard deviations of the control dividing the slope of regression line. (FIG. 6F) Correlation between the background-subtracted frequency ($f_{on}'$) and Poisson probability (P).

FIGS. 7A-D. Preparation and characterization of AuNP-based probes for the RSV detection. (FIG. 7A) Schematic illustrates the preparation of 15 nm AuNP probes, where NHS-ester activated bi-functional crosslinker DTSSP (3,3'-dithiobis(sulfosuccinimidyl propionate)) for the AuNPs-Synagis conjugation. (FIG. 7B) DLS, (FIG. 7C) Zeta potential, and (FIG. 7D) UV-Vis measurement for the AuNP probes characterization before and after conjugating with antibody-linked DTSSP.

Figure 8:
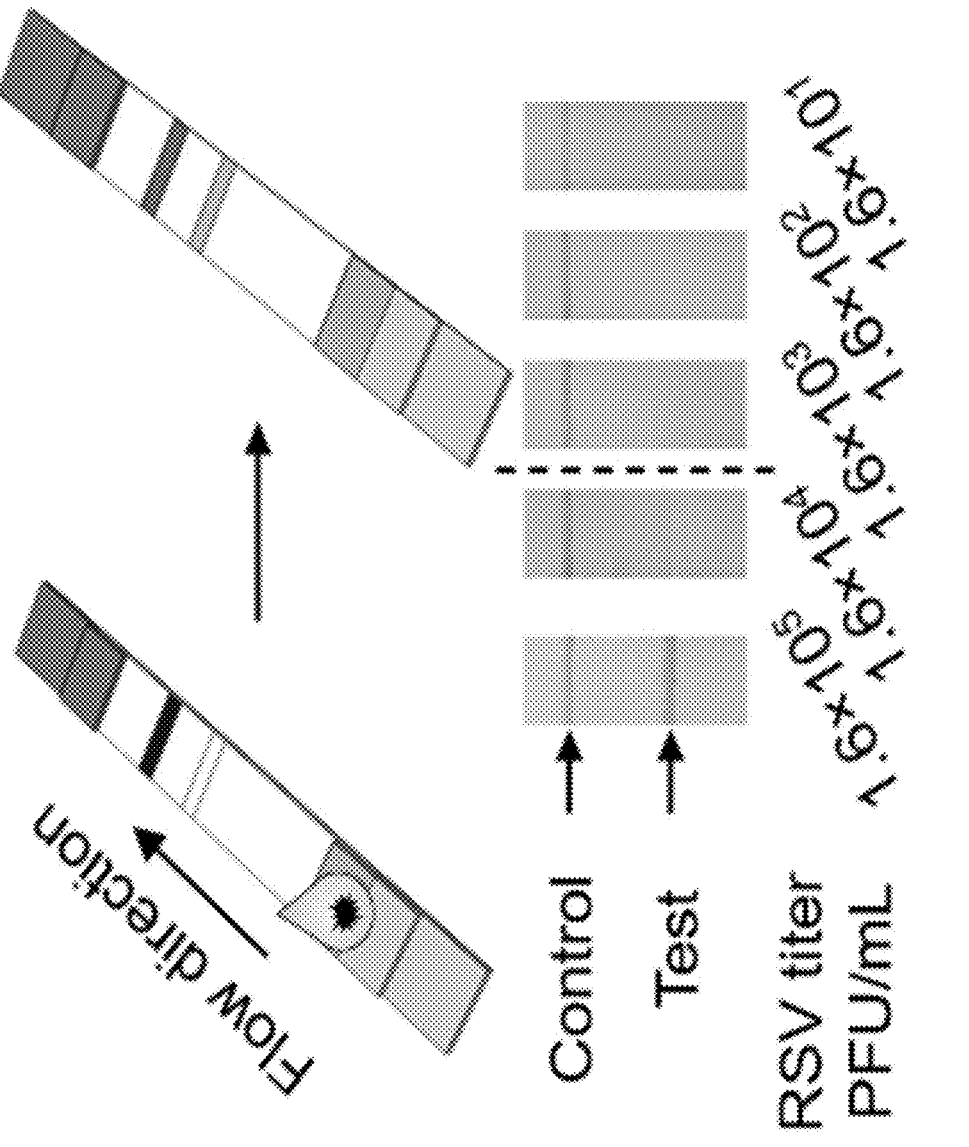

FIG. 8. RSV detection using a commercial lateral flow assay kit (BinaxNOW, Abbott). Schematic illustrates the assay operation and the digital photographs show the corresponding detection result with different RSV titers. The detection limit was estimated to be $1.6 \times 10^4$ PFU/mL.

FIGS. 9A-B. Large scale preparation of RSV A2. (FIG. 9A) Photographs of clinical RSV A2 strain infected HEp-2 cells at day 4. (FIG. 9B) Sucrose density gradient for RSV purification.

FIGS. 10A-B. Endpoint dilution assay for RSV quantification. (FIG. 10A) 96 well plate layout for serial dilutions of RSV stock inoculated onto HEp-2 cells. (FIG. 10B) Example of control well and RSV infected well after staining with crystal violet dye.

FIGS. 11A-E. Detection of respiratory syncytial virus (RSV) in a one-step homogenous immunoassay by DIAMOND. (FIG. 11A) The schematic illustration of a homogeneous immunoassay for RSV utilizing antibody-conjugated AuNPs as probes at room temperature (RT). (FIG. 11B) TEM images of AuNP probes targeting RSV that shows different morphologies. (FIG. 11C) Colorimetric analysis of the AuNP-based homogeneous immunoassay of different respiratory viruses. hMPV is Human metapneumovirus, PIV is Parainfluenza viruses, and IVA is Influenza A. (FIG. 11D) Bivariate plot of amplitude and AUC extracted from 3,000 pulses for the assay solutions with different RSV titers (PFU/mL). Dashed lines indicate the positions of thresholds calculated from the control sample. (FIG. 11E) Quantification of RSV titers as a function of frequency counting ($f_{on}$). Inset shows the linear detection range. Error bars in FIG. 11C and FIG. 11E indicate the standard deviations of three independent measurements, and the LOD was calculated as 3 standard deviations of the control divided by the slope of regression line.

FIGS. 12A-D. Morphology and size distribution histograms of different AuNPs by TEM. The results were counted by randomly measuring 200 particles in TEM images. For simplicity, the inventors referred the AuNPs in (FIG. 12A-D) as 15 nm, 35 nm, 50 nm, and 75 nm, respectively, and used them through the whole description.

FIGS. 13A-B. Optical characterizations for AuNPs of different sizes. (FIG. 13A) UV-Vis measurements. (FIG. 13B) DLS analysis.

FIG. 14. Kinetic study of colorimetric assay for real RSV using 15 nm GNP probes. The GNP probe-virus reaction can happen in 30 minutes. Similar results can be obtained by 30 nm GNP probes.

FIGS. 15A-B. Colorimetric detection of homogeneous assay using AuNPs as probes and SiO$_2$ beads as targets. (FIG. 15A) Absorbance spectra of assay solutions with different SiO$_2$ beads concentrations (particles/mL). (FIG. 15B) Analysis of the colorimetric detection result. Inset shows the linear range of the colorimetric detection. Error bars indicate the standard deviations of three independent measurements, and the LOD was calculated as 3 standard deviations of the control divided by the slope of regression line.

Figure 16:
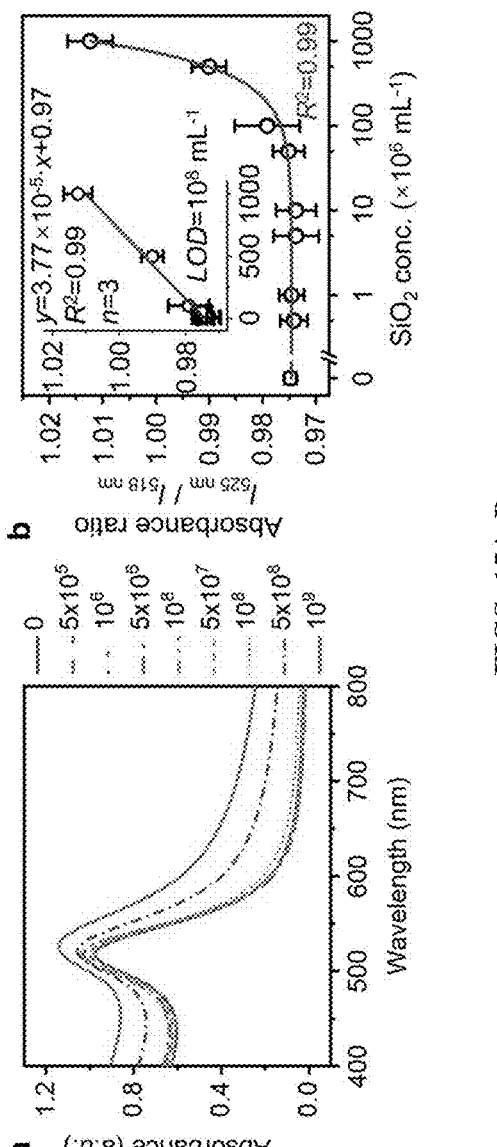

FIG. 16. Example of the PNB generation probability curve of 15 nm AuNPs used to determine the laser fluence threshold. Red arrow marks the laser fluence for probability=0, while the blue arrow marks the laser fluence for probability=100%.

Figure 17:
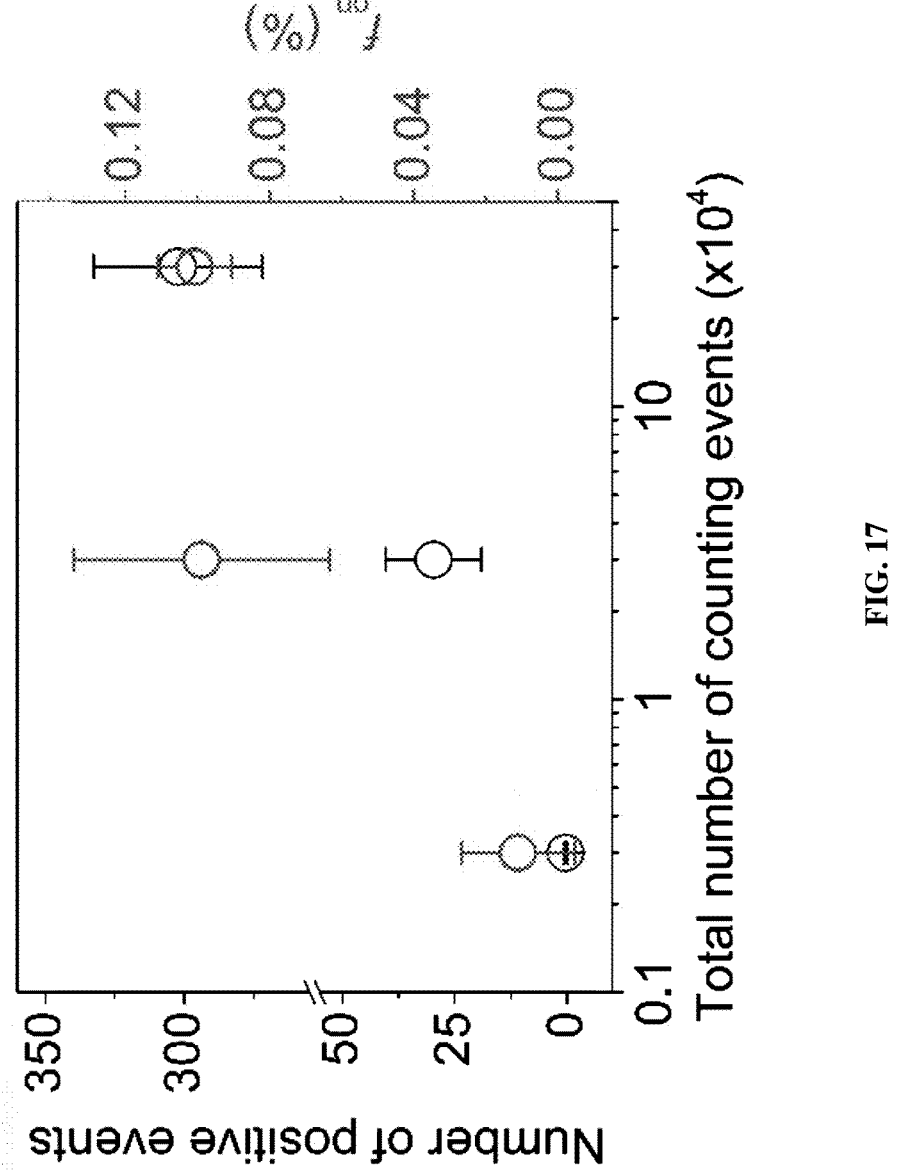

FIG. 17. The detection performance for the detection of 75 nm AuNPs ($\lambda$=0.0004) by DIAMOND with increasing counting number.

FIGS. 18A-B. Benchtop device for POC diagnosis of RSV. (FIG. 18A) A schematic of the container box. (FIG. 18B) Inside view of the nanobubble detection platform, consisting of pump and probe laser, photodetector, sample-loading tray with a syringe pump, and other optical components.

FIGS. 19A-B. Characterization of Au nanorod (AuNR) prepared via a seed-growth method. (FIG. 19A) AuNRs with different seed amount. (FIG. 19B) TEM image of 15 nm×50 nm AuNRs in sodium citrate with peak wavelength at 810 nm.

FIGS. 20A-C. Size and shape effect of GNPs on RSV binding. (FIG. 20A) TEM images of different GNPs-Syn probes before (top row, i-v: 15 nm, 30 nm, 45 nm, 100 nm, 15×50 nm rod) and after (bottom row, vi-x: 15 nm+RSV, 30 nm+RSV, 45 nm+RSV, 100 nm+RSV, 15×50 nm rod+RSV) incubated with RSV stock solutions. Scale bar=200 nm. All virus samples are stained by 2% uranyl acetate. (FIG. 20B) Corresponding absorbance of GNPs-Syn probes with different size before and after incubated with RSV stock solutions. Quantitative analysis of (FIG. 20C) size and shape effect of GNPs on RSV binding. Small size of GNPs provide higher binding effectiveness. Here the binding effectiveness is defined as the area density of nanoparticles on the virus (e.g., particle number/unit area).

FIGS. 21A-D. Colorimetric assay performance of RSV detection using the GNRs probes. (FIG. 21A) Spectral absorbance measurements of GNRs probes incubated with a series of RSV dilutions. (FIG. 21B) Contour plot for optimization of wavelength ratio to achieve sensitive detection of RSV. (FIG. 21C) The result of RSV detection using the GNRs probes. (FIG. 21D) Linear calibration curve for determination of limit of detection (LOD) of RSV.

FIGS. 22A-C. Transmission electron microscopy images of the silver-based nanoparticles. (FIG. 22A) Silver nanoparticles, (FIG. 22B) hollow gold-silver alloy nanoshells, and (FIG. 22C) hollow gold-silver alloy nanocages.

Figure 23:
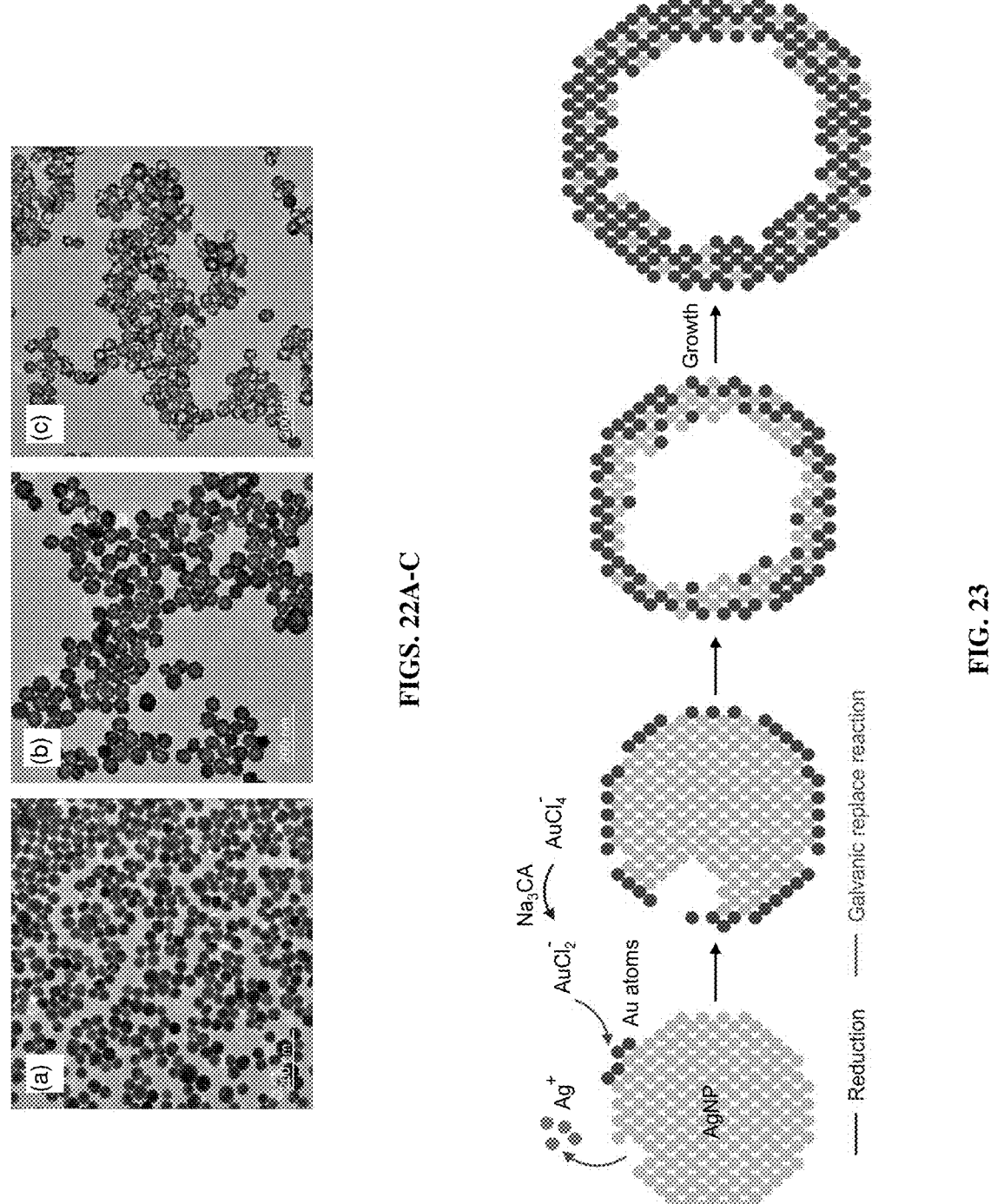

FIG. 23. Schematic illustration of preparation of AuAgNSs via galvanic replacement reaction in the presence of sodium citrate ($Na_3CA$), which reduces the $HAuCl_4$ into $AuCl_2^-$.

FIGS. 24A-F. The growth of AuAg nanoshells at 2 mM $Na_3CA$. (FIGS. 24A-C) Morphological change upon injecting the $HAuCl_4$. (FIGS. 24D-E) The HADDF-STEM image and EDX mapping profile of a AuAg nanoshell. (FIG. 24F) The spectra monitoring during the growth of AuAg nanoshells.

FIGS. 25A-F. The impact of $Na_3CA$ concentration on the morphology of the product. (FIG. 25A) Schematic illustration of the products obtained at increased concentration of $Na_3CA$. (FIGS. 25B-F) The TEM images of product obtained at 0, 0.5, 1, 2, and 5 mM $Na_3CA$.

Figure 26:
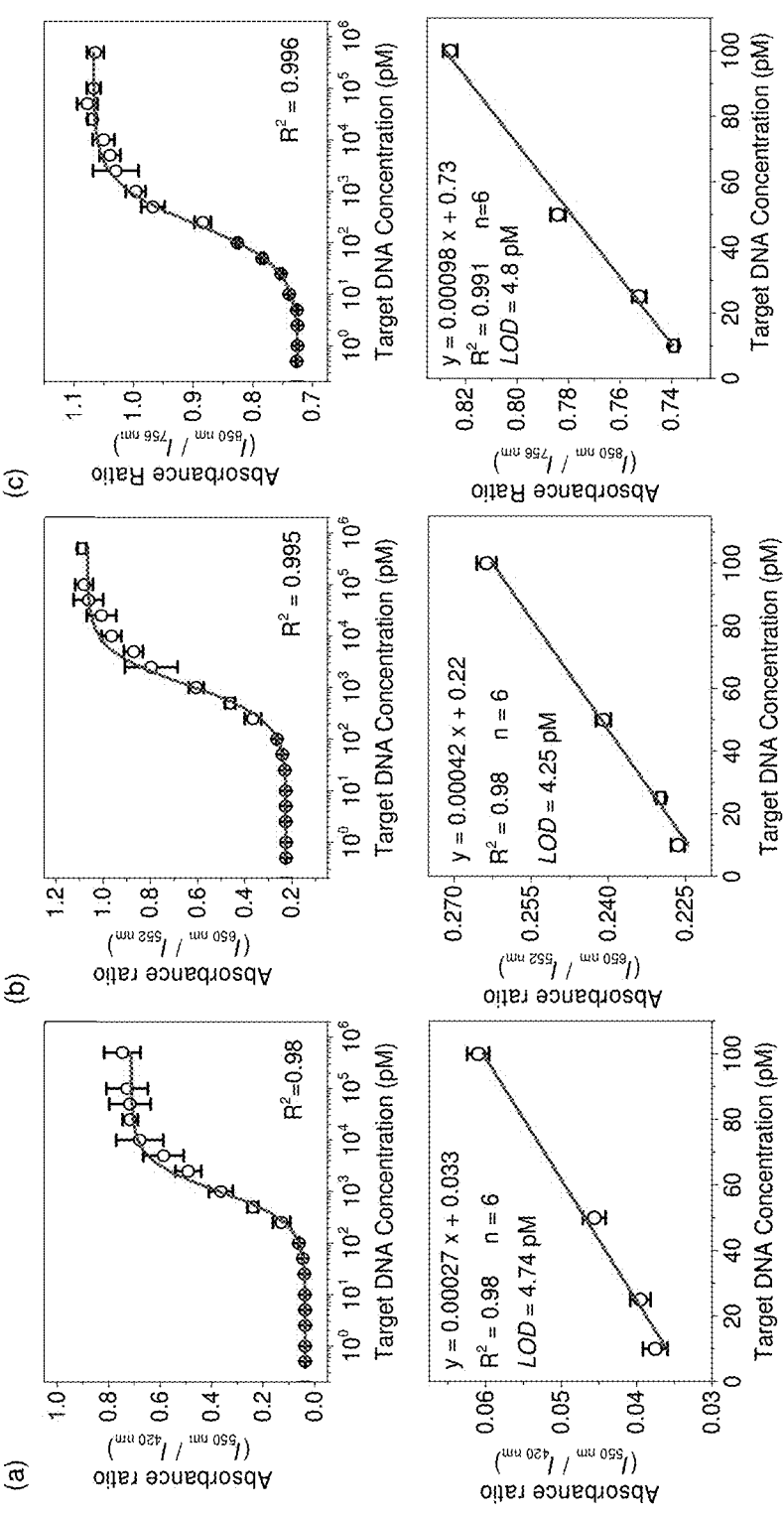

FIGS. 26A-C. Assay performance in oligonucleotide detection using the (FIG. 26A) silver nanoparticles, (FIG. 26B) hollow gold-silver alloy nanoshells, and (FIG. 26C)

hollow gold-silver alloy nanocages as sensors. Conditions are kept the same for all experiments. LOD means limit of detection.

Figure 27:
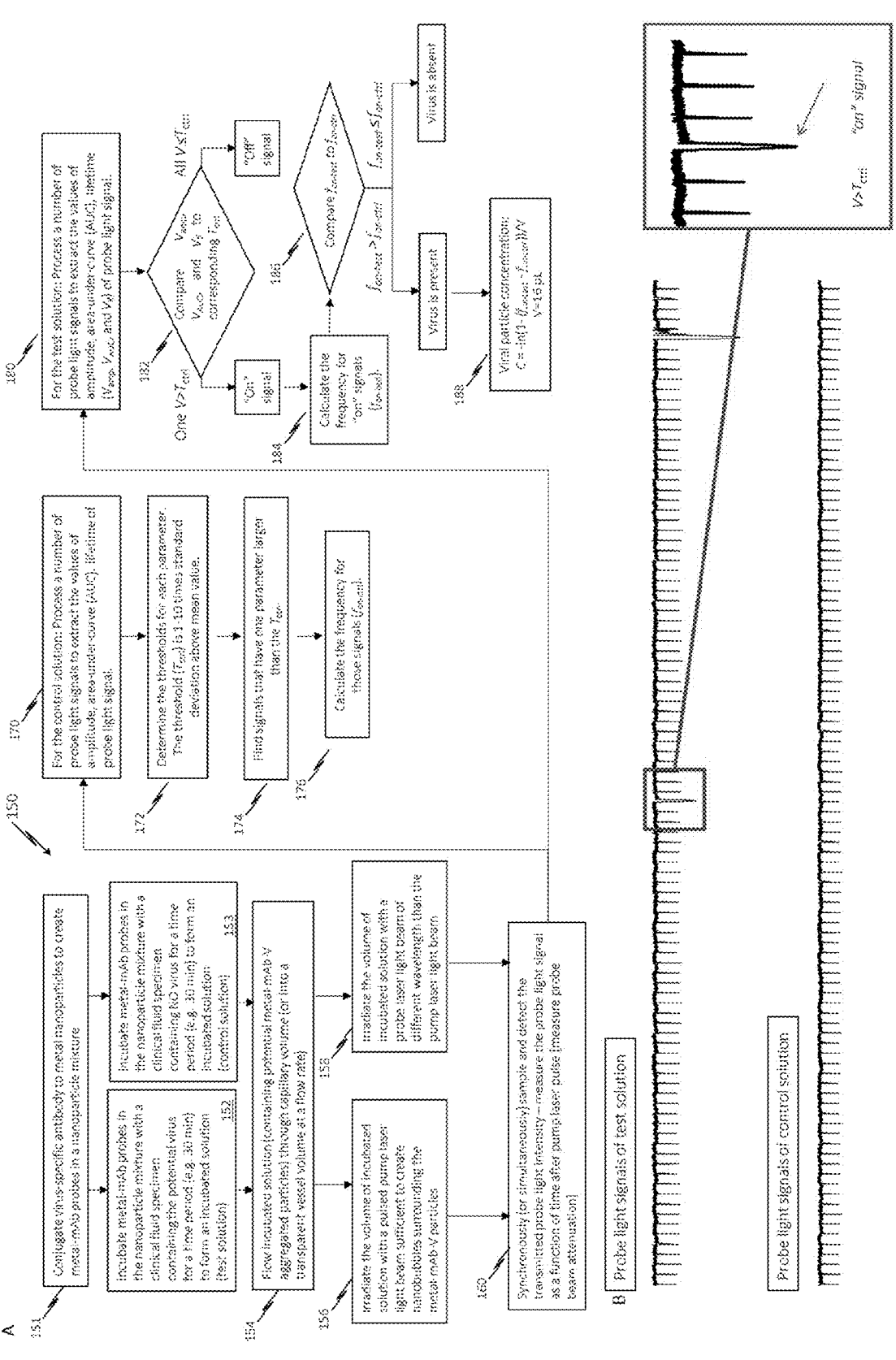

FIGS. 27A-B. Schematic illustration of the working flow for DIAMOND (FIG. 27A). Illustration of data output (FIG. 27B).

Figure 28:
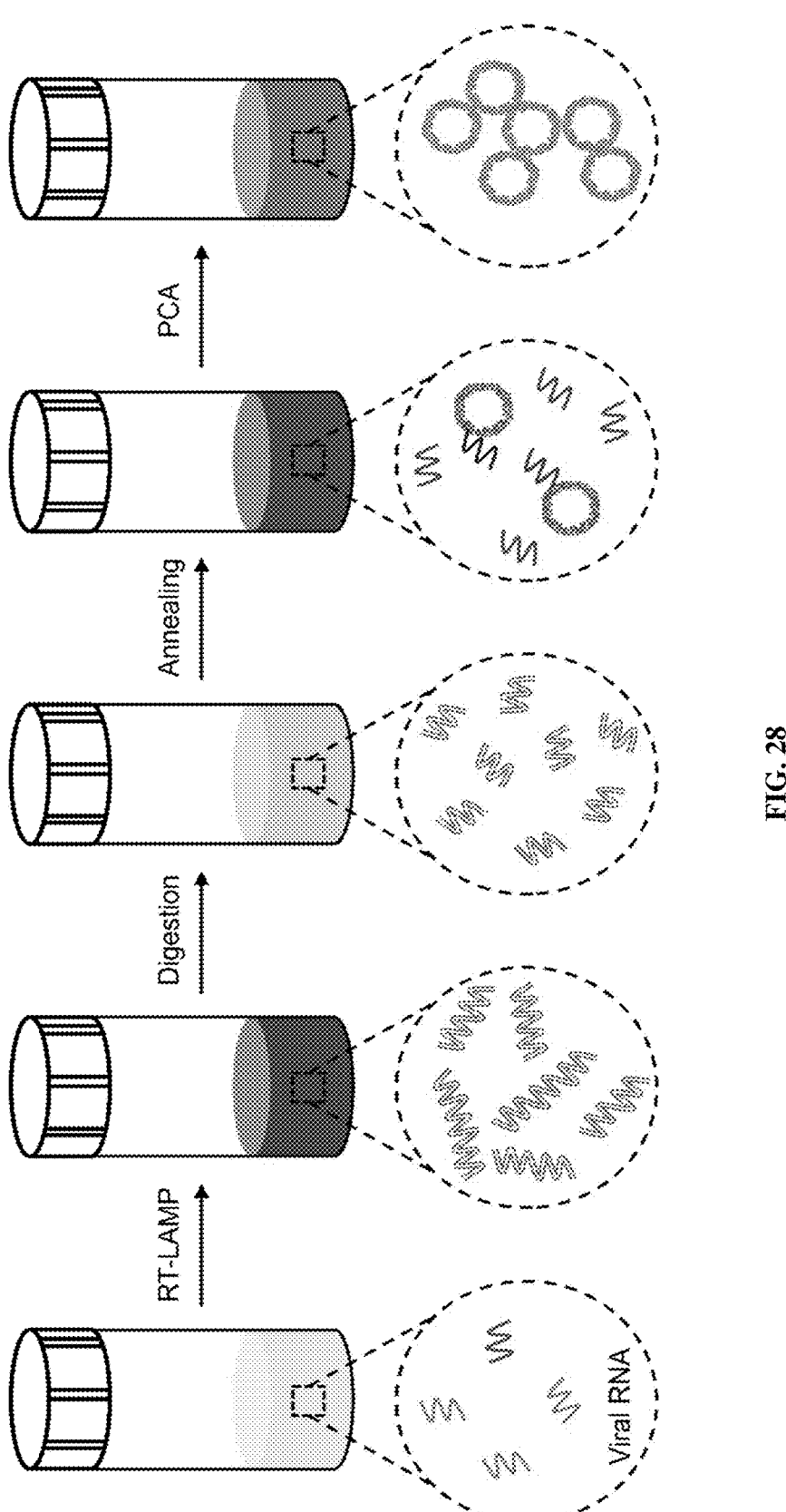

FIG. 28. Schematic illustration of the concept of single-molecule detection of RNA via isothermal amplification and plasmonic coupling assay using AuAgNSs as labels.

Figure 29:
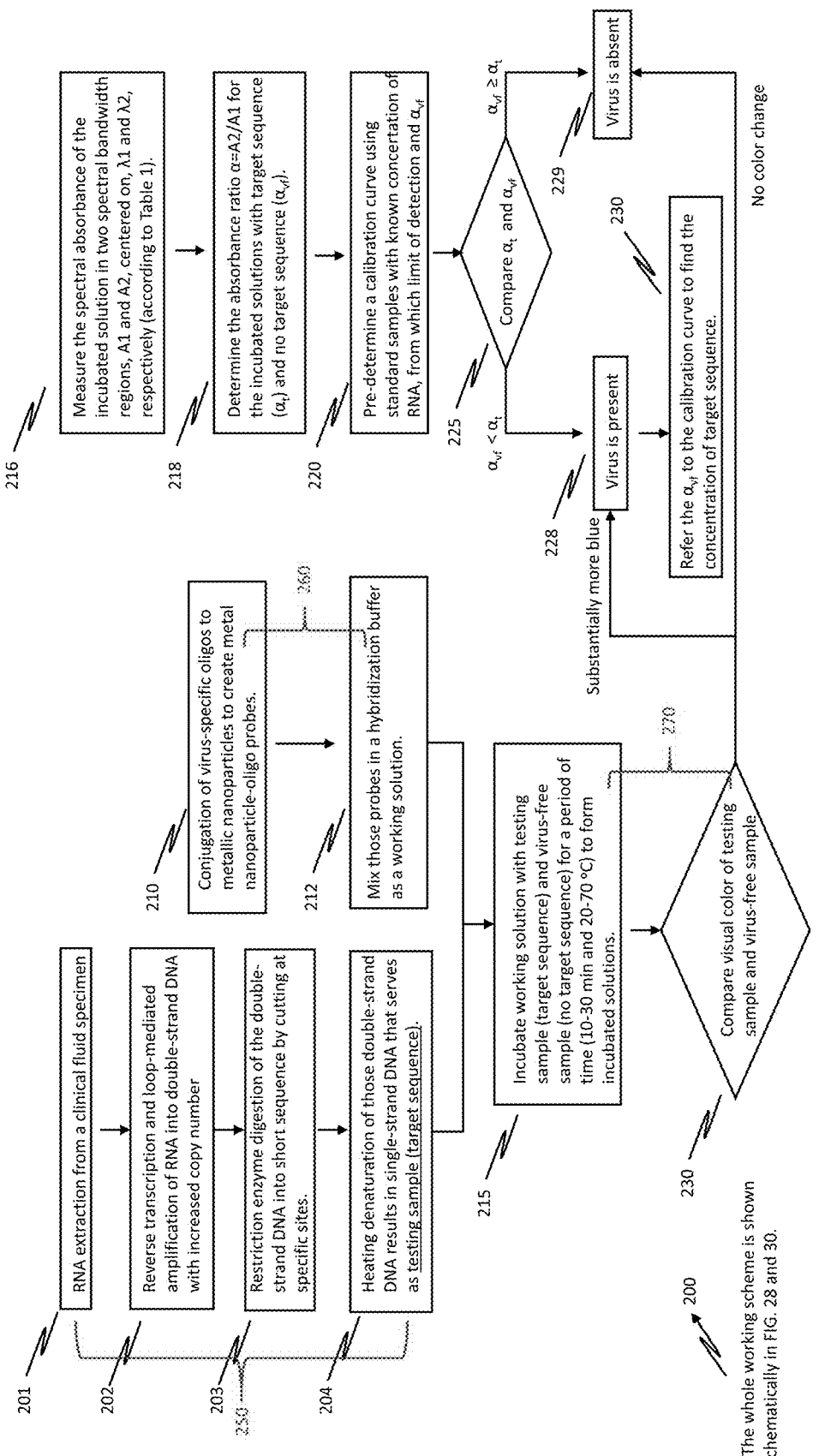

FIG. 29. Schematic illustration of the working flow for single-molecule detection of RNA via isothermal amplification and plasmonic coupling assay using AuAgNSs as labels.

Figure 30:
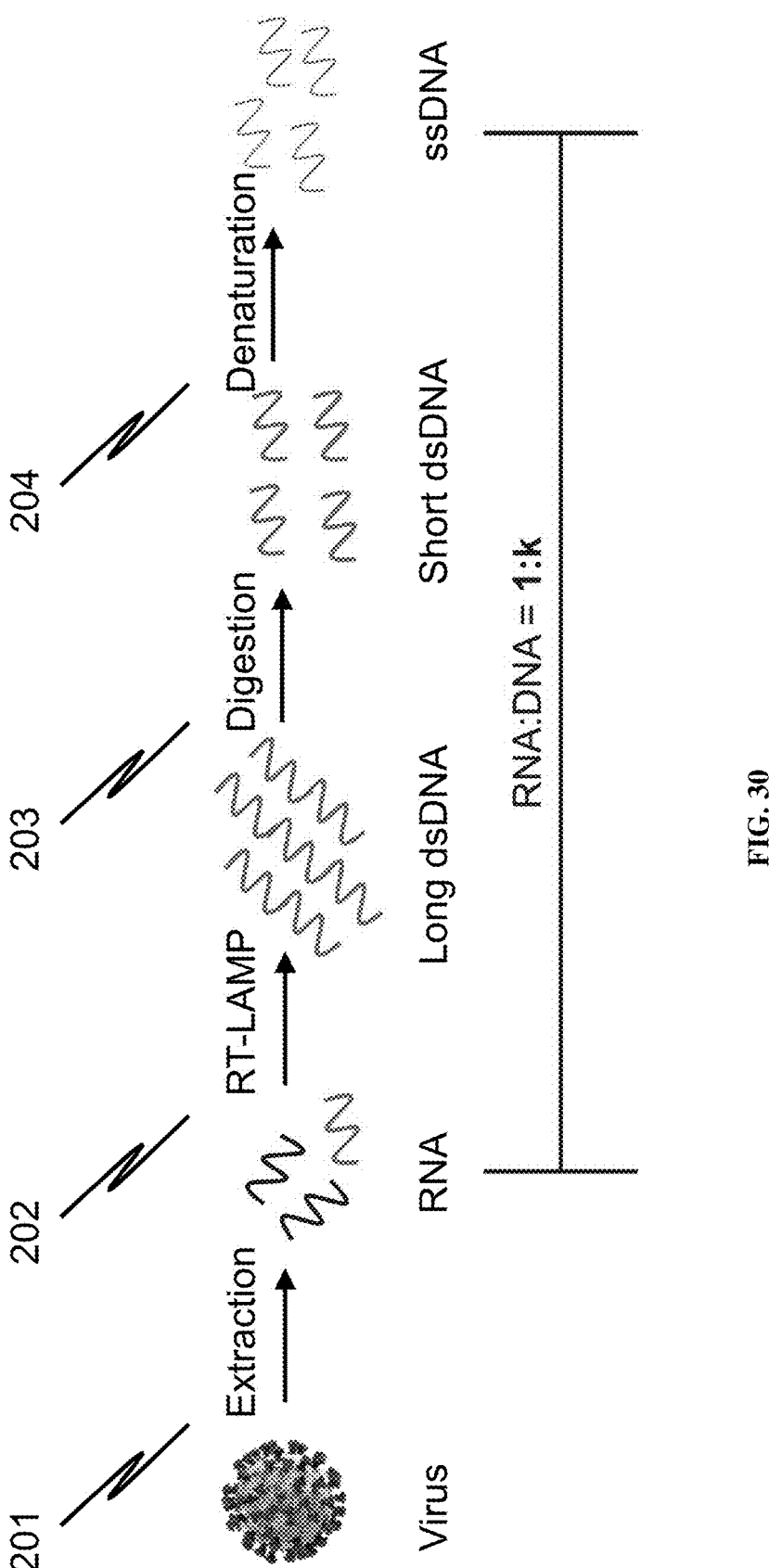

FIG. 30. Viral RNA extraction and reverse transcription-loop-mediated isothermal amplification (RT-LAMP) assay for preparation of ssDNA as analytes for plasmonic coupling assay.

Figure 31:
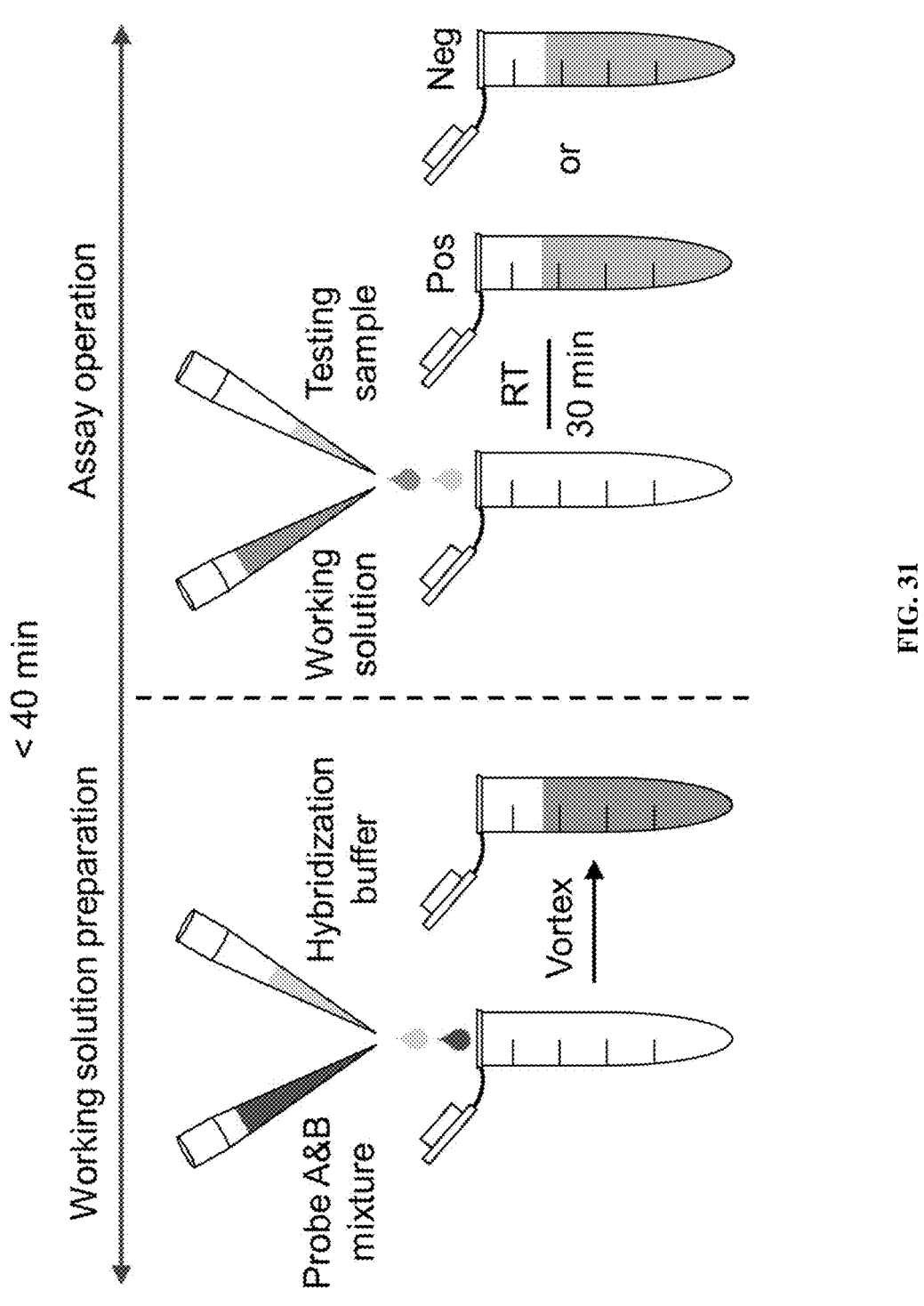

FIG. 31. Preparation of a working solution for plasmonic coupling assay.

Figure 32:
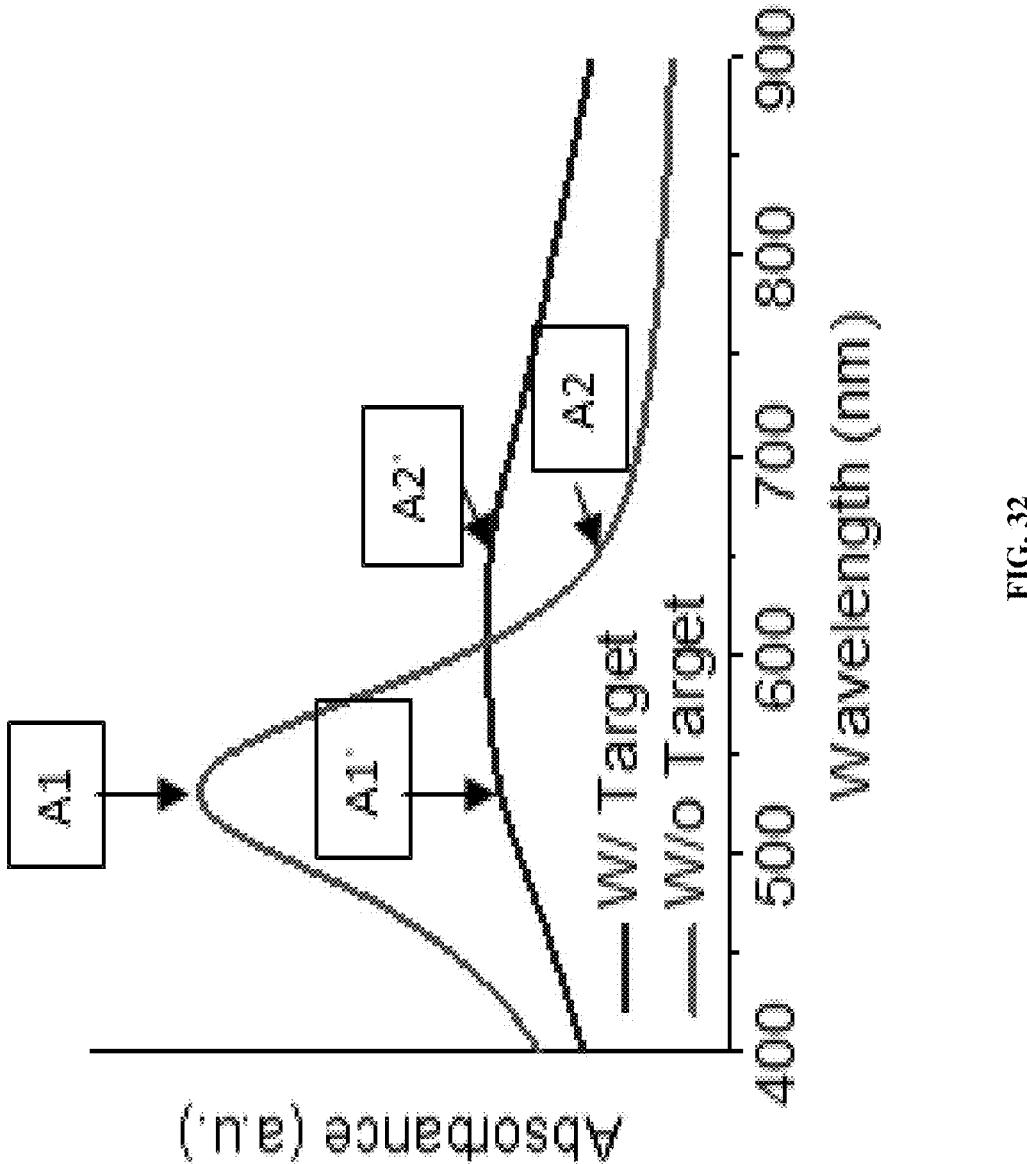

FIG. 32. The determination of absorbance ratio of a detection result via spectral reading.

Figure 33:
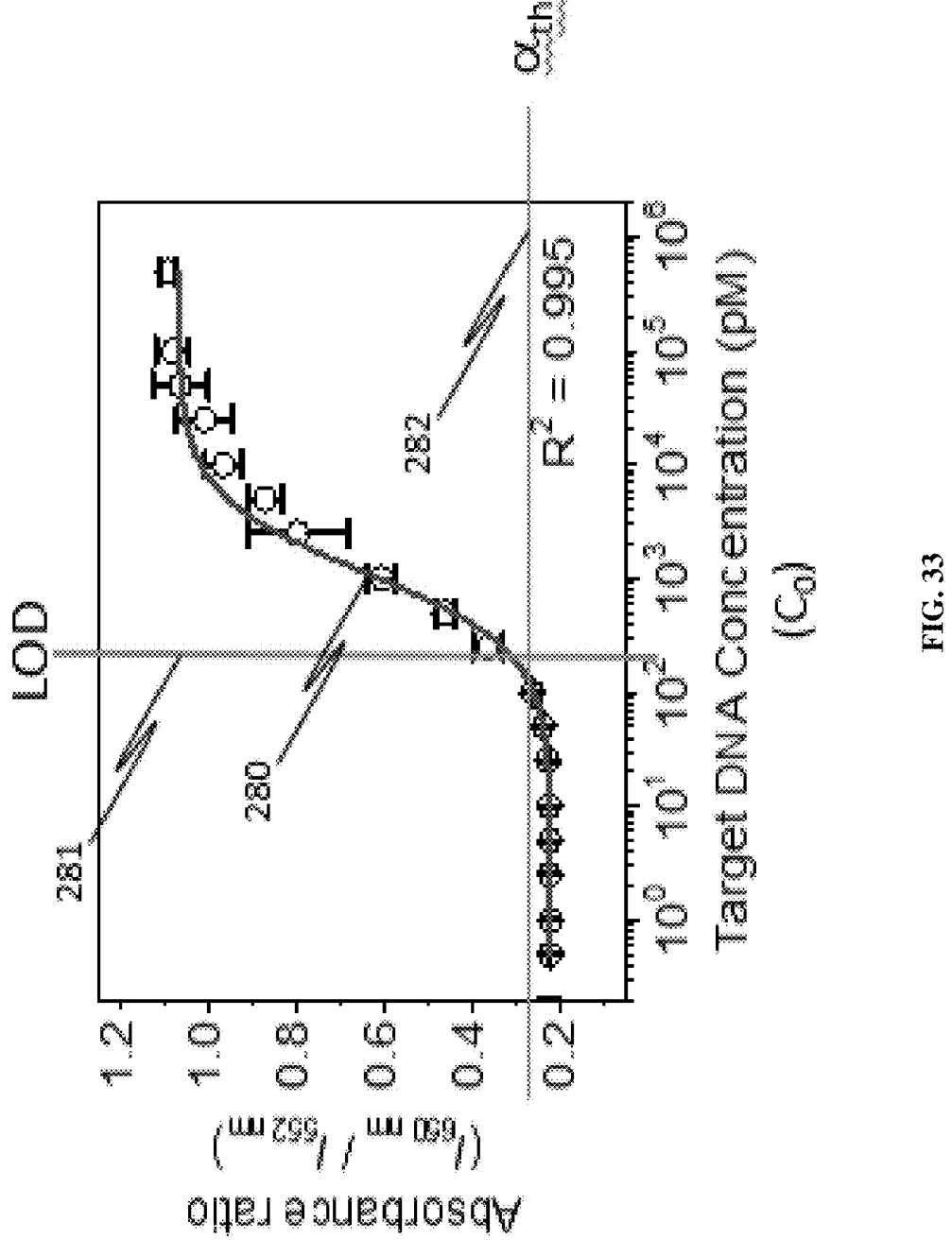

FIG. 33. The determination of limit of detection (LOD) for standard samples with known concentrations.

FIG. 34. Assay performance in oligonucleotide detection using the gold nanoparticles as probes.

FIGS. 35A-D. A diagnostic approach for the detection of SARS-COV-2 RNA. (FIG. 35A) The schematic illustration of the diagnostic approach, where RT-LAMP is reverse-transcription loop-mediate amplification, Digestion is restriction enzyme digestion, and Denaturation can be performed at 95° C. for 5 min. (FIG. 35B) A digital photo of the detection results, where input RNA with 10 copies per microliter or more causes a color change. (FIG. 35C) UV-Vis measurements of the assay solutions at varied RNA concentration. (FIG. 35D) Qualitative determination of RNA concentration through the absorbance ratio method.

DETAILED DESCRIPTION

The inventors have developed plasmonic biosensors made of silver or gold/silver alloy. These biosensors feature high peak extinction and exhibit superior optical response when form clusters or aggregates due to the presence of target molecules. Based on these biosensors, the inventors further developed a diagnostic approach for single-molecule detection of nucleic acids. In this approach, the target analyte (e.g., DNA or RNA) is amplified by an isothermal amplification technique from a commercially available kit, followed by restriction enzyme digestion and heat denaturation. The resulting product serves as the target molecule and can be detected by the plasmonic biosensors, where a color change can be visualized by the naked eye or measured by a simple spectrometer.

Second, the inventors developed plasmonic biosensors made of gold nanorods. These biosensors provide enlarged surface area and thus increased binding sites for the target molecules (e.g., viral particles). With the ability to accumulate more numbers per analyte, these gold nanorod-based biosensors show enhanced detection sensitivity compared to that of spherical nanoparticles.

Third, the inventors developed a novel strategy for a simplified digital homogeneous assay based on DIgitAl plasMONic nanobubble Detection (DIAMOND). Plasmonic nanobubbles (PNBs) refer to the vapor bubbles generated by short laser pulse excitation of plasmonic nanoparticles (NPs) and amplify their intrinsic absorption for the detection by a secondary probe laser. PNBs have the lifetime that lasts nanoseconds and are sensitive to the physical parameters of NPs such as sizes, shape, concentration, and clustering state. Taking advantage of these unique properties, the inventors designed an optofluidic setup to flow the assay solution in a micro-capillary for high throughput detection. The focused laser beam probes a microscale "virtual compartment" of about 16 µL and detects the PNB generation from single probes. Since PNBs are transient events, there is no crosstalk between laser pulses, which allows "on" and "off" signal counting in a compartment-free manner.

In digital assays, increasing the total counting number benefits the sensitivity enhancement and reduces the measurement error. PNB detection system optimization can include a portable pulsed nanosecond laser with a megahertz repetition rate that will be implemented in a benchtop device for millions of data points recording in a short time (FIG. 22). Two laser beams will be aligned by adjusting the small mirrors, filters, convex lens, and other optical components. The LabVIEW interface can be used to control the entire sample loading system, PNB testing system, data acquisition, and analysis system.

These and other aspects of the disclosure are set out in detail below.

I. PARTICLES

The particles of the present disclosure can take a wide variety of forms. For example, in their most basic sense, they are noble metal nanoparticles, in particular those made of gold, silver, or gold/silver. A nanoparticle is usually defined as a particle of matter that is between 1 and 100 nanometres (nm) in diameter. The term is sometimes used for larger particles, up to 500 nm, or fibers and tubes that are less than 100 nm in only two directions. At the lowest range, metal particles smaller than 1 nm are usually called atom clusters instead.

Nanoparticles are usually distinguished from microparticles (1-1000 µm), "fine particles" (sized between 100 and 2500 nm), and "coarse particles" (ranging from 2500 to 10,000 nm), because their smaller size drives very different physical or chemical properties, like colloidal properties and optical or electric properties. Being more subject to the Brownian motion, they usually do not sediment, like colloidal particles that conversely are usually understood to range from 1 to 1000 nm.

Being much smaller than the wavelengths of visible light (400-700 nm), nanoparticles cannot be seen with ordinary optical microscopes, requiring the use of electron microscopes or microscopes with laser. For the same reason, dispersions of nanoparticles in transparent media can be transparent, whereas suspensions of larger particles usually scatter some or all visible light incident on them.

The properties of nanoparticles often differ markedly from those of larger particles of the same substance. Since the typical diameter of an atom is between 0.15 and 0.6 nm, a large fraction of the nanoparticle's material lies within a few atomic diameters from its surface. Therefore, the properties of that surface layer may dominate over those of the bulk material. This effect is particularly strong for nanoparticles dispersed in a medium of different composition since the interactions between the two materials at their interface also become significant.

Nanoparticles occur widely in nature and are objects of study in many sciences such as chemistry, physics, geology, and biology. Being at the transition between bulk materials and atomic or molecular structures, they often exhibit phenomena that are not observed at either scale. They are an important component of atmospheric pollution, and key ingredients in many industrialized products such as paints, plastics, metals, ceramics, and magnetic articles. The production of nanoparticles with specific properties is an important branch of nanotechnology.

In general, the small size of nanoparticles leads to a lower concentration of point defects compared to their bulk counterparts, but they do support a variety of dislocations that can be visualized using high-resolution electron microscopes. However, nanoparticles exhibit different dislocation mechanics, which, together with their unique surface structures, results in mechanical properties that are different from the bulk material.

Anisotropy in a nanoparticle leads to a lot of changes in the properties of the nanoparticles. Non-spherical nanoparticles of gold, silver, and platinum due to their fascinating optical properties are finding diverse applications and are of great interest in the field of research. Non-spherical geometries of nanoprisms give rise to high effective cross-sections and deeper colors of the colloidal solutions. The possibility of shifting the resonance wavelengths by tuning the particle geometry is very interesting for using these nanoparticles in the fields of molecular labeling, biomolecular assays, trace metal detection, and nanotechnical applications. Anisotropic nanoparticles display a specific absorption behavior and stochastic particle orientation under unpolarized light, showing a distinct resonance mode for each excitable axis. This property can be explained based on the fact that on a daily basis there are new developments being made in the field of synthesis of these nanoparticles for preparing them in high yield.

Nanoparticles are often spherical but may take more complex shapes such as rods, cages, or shells. Nanorods range from 1-100 nm. They may be synthesized from metals or semiconducting materials. Standard aspect ratios (length divided by width) are 3-5. Nanorods are produced by direct chemical synthesis. A combination of ligands act as shape control agents and bond to different facets of the nanorod with different strengths. This allows different faces of the nanorod to grow at different rates, producing an elongated object.

One potential application of nanorods is in display technologies, because the reflectivity of the rods can be changed by changing their orientation with an applied electric field. Another application is for microelectromechanical systems (MEMS). Nanorods, along with other noble metal nanoparticles, also function as theragnostic agents. Nanorods absorb in the near IR, and generate heat when excited with IR light. This property has led to the use of nanorods as cancer therapeutics. Nanorods can be conjugated with tumor targeting motifs and ingested. When a patient is exposed to IR light (which passes through body tissue), nanorods selectively taken up by tumor cells are locally heated, destroying only the cancerous tissue while leaving healthy cells intact. Nanorods based on semiconducting materials have also been investigated for application as energy harvesting and light emitting devices.

A nanoshell is a type of spherical nanoparticle consisting of a dielectric core which is covered by a thin metallic shell (usually gold). These nanoshells involve a quasiparticle called a plasmon which is a collective excitation or quantum plasma oscillation where the electrons simultaneously oscillate with respect to all the ions.

The simultaneous oscillation can be called plasmon hybridization where the tunability of the oscillation is associated with mixture of the inner and outer shell where they hybridize to give a lower energy or higher energy. This lower energy couples strongly to incident light, whereas the higher energy is an anti-bonding and weakly combines to incident light. The hybridization interaction is stronger for thinner shell layers, hence, the thickness of the shell and overall particle radius determines which wavelength of light with which it couples. Nanoshells can be varied across a broad range of the light spectrum that spans the visible and near infrared regions. The interaction of light and nanoparticles affects the placement of charges which affects the coupling strength. Incident light polarized parallel to the substrate gives an s-polarization, hence the charges are further from the substrate surface which gives a stronger interaction between the shell and core. Otherwise, a p-polarization is formed which gives a more strongly shifted plasmon energy causing a weaker interaction and coupling.

Nanocages are hollow, porous nanoparticles ranging in size from 10 to over 150 nm. In one form they are gold, and can be created by reacting silver nanoparticles with chloroauric acid ($HAuCl_4$) in boiling water. Whereas gold nanoparticles absorb light in the visible spectrum of light (at about 550 nm), gold nanocages absorb light in the near-infrared, where biological tissues absorb the least light. Because they are also biocompatible, gold nanocages are promising as a contrast agent for optical coherence tomography. Gold nanocages also absorb light and heat up (photothermal effect), killing surrounding cancer cells. Nanocages have been functionalized with cancer-specific antibodies.

II. ANALYTES AND SAMPLES

The analytes and samples that may be employed with the methods of the present disclosure are nearly limitless. The samples may be biological in nature, such as those taken from living organisms-ranging from microbes to mammals. They may be derived from ecosystems, i.e., environmental systems as well as industrial or commercial zones. They may also be products, such as food stuffs, including animal and human foods, cosmetics, pharmaceutical drugs, herbicides, pesticides, fungicides, or other agricultural, pharmaceutical or industrial materials. The samples may be pre-processed, such as to purify the samples, increase the concentration of analyte and/or reduce the concentration contaminants, to improve detection or to stabilize the materials therein.

The analytes may also be of nearly any nature. They may be biological in nature, such as peptides, proteins, carbohydrates, lipids, nucleic acids (DNA/RNA), as well as infectious agents including bacteria, parasites, viruses, and fungi. Particular agents of interest include respiratory syncytial virus (RSV), malaria (genus *Plasmodium*) and SARS-COV-2 and their oligonucleotides sequences. Other analytes includes chemical species, metal ions, polymers, toxins, industrial by-products or waste products.

Additional particular examples include pathogenic or conditionally pathogenic bacteria. For example, *Staphylococcus, Streptococcus. Chlamydophila, Rickettsia, Ehrlichia, Listeria, Mycobacterium, Brucella, Staphylococcus aureus*, including methicillin-resistant *S. aureus* (MRSA) *Corynebacterium, Enterococcus, Bacillus, Clostridium, Rathybacter, Leifsonia*, and *Clavibacter*. Examples of Gramnegative bacteria include *Bordetella, Borrelia, Burcelia, Campylobacteria, Escherichia, Francisella, Haemophilus, Helicobacter, Legionella, Leptospira, Neisseria, Pseudomonas, Salmonella, Shigella, Treponema, Vibrio*, and *Yersinia*. Gram-indeterminate bacteria include *Mycobacterium tuberculosis* or *Mycobacterium leprae*.

Some additional non-limiting examples of pathogenic virus include influenza virus, smallpox, BK virus, JC virus, human papillomavirus, adenovirus, herpes simplex type 1, herpes simplex type 2, MERS virus, HTLV-1 or -2, varicella-zoster virus, Epstein barr virus, human cytomegalovirus, human herpesvirus type 8, Norwalk virus, human bocavirus, rubella virus, hepatitis E virus, hepatitis B, C or D virus, human immunodeficiency virus (HIV), Ebola virus, Rift Valley Fever virus, zika virus, hantavirus, chikungunya virus, rabies virus, rotavirus, and West Nile virus.

III. ASSAYS

The assays of the present disclosure are simple and one-step sensing methods that require minimal sample handling/processing and are therefore promising for rapid detection in low resource environments. In certain embodiments, the methods can be completed in less than one hour, such as about 30-60 minutes, or about 30 minutes, using simple, hand held devices or even with unaided visual detection.

The as-prepared nanoparticle sensors are employed to target the analytes in a mixture sample. After incubation, the mixture samples are ready for detection by any of the described methods, including optical methods such as spectrophotometry, including UV-Vis spectroscopy, visual detection by the unaided human eye, such as by color change, detecting color intensity at selected wavelegnths (such as 2 or 3 wavelengths), and laser induction of nanobubbles (from nanoparticle aggregates).

The methods may further comprise positive and/or negative control reactions. For example, the binding agent is contacted with a known sample containing a known target (optionally including a known amount) and/or with a sample known to lack the target. In addition, the assay may be formatted for quantitative or semi-quantitative results.

IV. EXAMPLES

The following examples are included to demonstrate preferred embodiments. It should be appreciated by those of skill in the art that the techniques disclosed in the examples which follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Nanoparticle Biosensor Systems and Methods for Infectious Disease Diagnosis Methods. Antibody and GNP conjugation. Synagis (Palivizumab) was chosen as the RSV-specific monoclonal antibody. Synagis provides passive immunity against RSV by binding the RSV envelope fusion protein (RSV—F) on the virus surface and blocking a critical step in the membrane fusion process. GNPs (15 nm, 30 nm, 45 nm) were synthesized on the basis of the standard citrate reduction technique with slight modifications, and GNP concentration was calculated according to their optical properties. To conjugate Synagis onto GNPs surface, the inventors tested passive absorption, PEGylated method, and DTSSP method reported earlier (Liu et al., *Analyst*, 140, 3989-3995, 2015; Daiet al., *Angew Chem Int Ed Engl* 53, 5093-5096, 2014; Driskell et al., *Analyst* 136, 3083, 2011) to create GNP-Syn probes. The probes were characterized by dynamic light scattering (DLS) using Malvern Zetasizer Nano (Malvern Instruments Ltd., UK).

Large scale Propagation of RSV A2. Clinical frozen stock of RSV A2 strain (from UTSW medical center) was propagated in HEp-2 cells. IT-150 cm$^2$ flask of Hep-2 cells were infected at a multiplicity of infection (moi) of 0.5 pfu/cell in 5 mls DMEM/0% FBS and adsorbed for 2 hours at 37° C. After 2 hrs, the inoculum was removed and was replaced by DMEM/10% FBS to a final volume of 13 mls. Once the cell culture shows >90% cytopathic effects (CPE) (typically at day 4) (FIG. 9A), all but 2 ml of the media is removed and subsequently the cell monolayer is scraped and the cells are collected into a 50 ml tube. Cell lysates were made by vortexing the cell suspension in the tubes 3 times, 30 seconds each time. Cell debris was removed by centrifugation at 3000 rpm for 7 minutes at 4° C. The supernatant was stored on ice or aliquoted after the additions of sucrose, HEPES and magnesium to stabilize the virus. Aliquoted samples were stored at −80° C. or expanded to a working stock.

Sucrose density gradient for RSV purification. RSV suspension was layered onto (30-60%) dual density sucrose cushion and then centrifuged at 23,500 rpm for 118 minutes at 4° C. The virus settled at the interface of the two sucrose layers (typically appears as a fluffy layer) (FIG. 9B). This fluffy layer is removed from the gradient with sterile needles and transfer to 15 ml sterilized polypropylene tubes. Aliquots were made and stored at −80° C. Virus titration, using standard virological plaque techniques, was determined by endpoint titration (FIGS. 10A-B).

Analog GNP aggregation assay. RSV and other closely related respiratory viruses such as Human metapneumovirus (hMPV), Parainfluenza virus (PIV), and Influenza Virus A (IVA) were then incubated with GNP-Syn probes for at least 30 min at room temperature in the presence of 5% sucrose and cell debris in 1×PBS buffer (1M MgSO4, 0.5M HEPES pH 7.7, 1M NaCl). The optical spectrum was measured using a Beckman Coulter UV-Vis spectrophotometer (model DU800), and the GNP targeted virus samples were observed by transmission electron microscopy (TEM JEOL JEM 2100). Each of the GNP samples was spotted onto a thin carbon film coated Cu grids (300 mesh, Pacific Grid Tech) and air-dried for TEM characterization.

Figure 1:
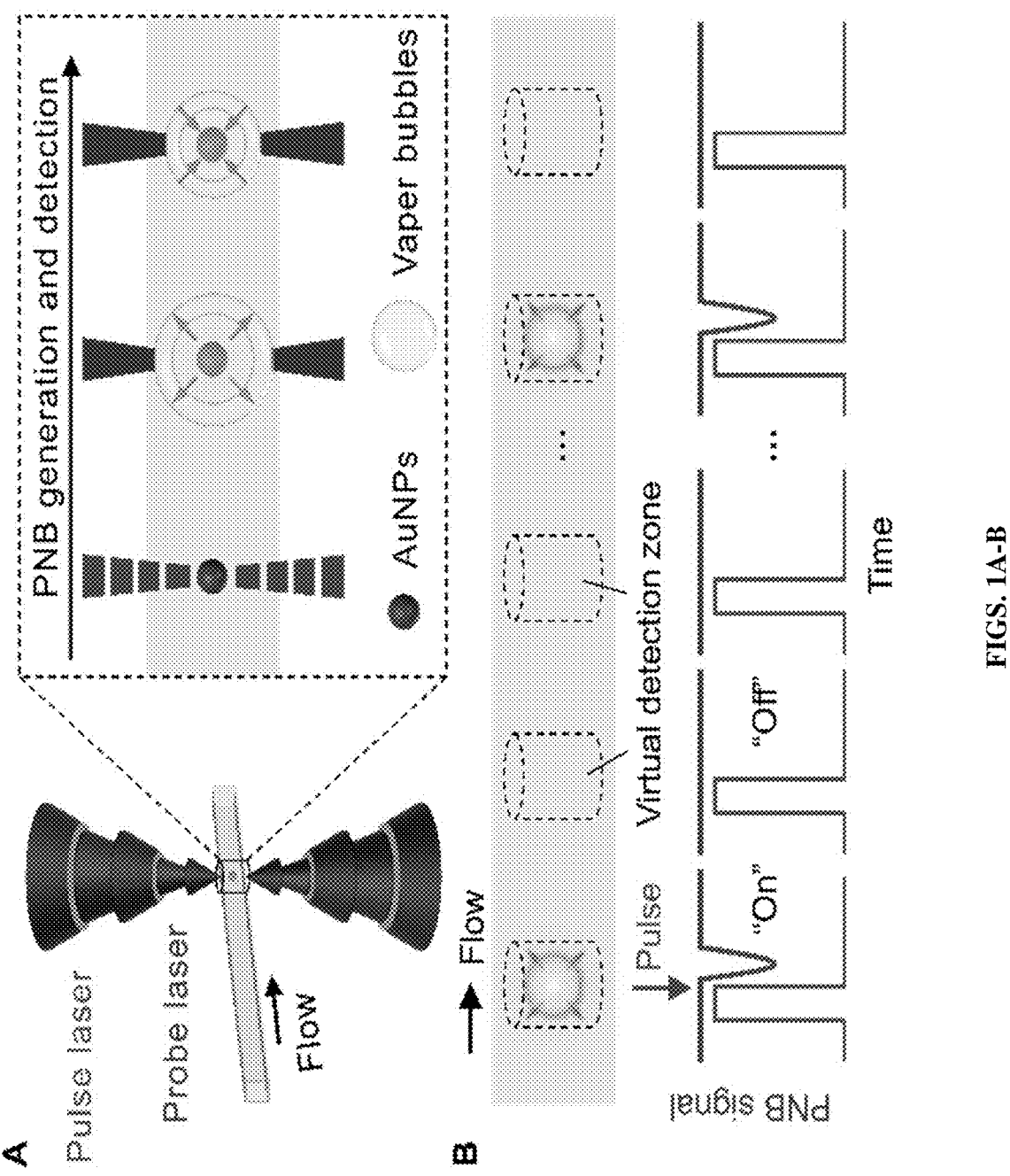
FIGS. 1A-B. The schematics illustration for the concept of digital plasmonic nanobubble detection (DIAMOND).

Digital plasmonic nanobubble detection. To selectively detect coupled GNPs, which indicate the presence of the RSV, ultrashort laser pulses were applied to activate the coupled GNPs and create transient cavitation bubbles, i.e. plasmonic nanobubbles (PNBs), at a laser intensity threshold well above the threshold required for single nanoparticle cavitation (Filbrunet et al., *Analyst,* 142, 4456, 2017). The PNBs can be readily detected due to the high refractive index mismatch and scattering (FIG. 1A). Basically, a syringe pump is used to flow the sample (GNP-syn+RSV) through a simple micro-capillary channel (ID=200 μm). Then a short laser pulse (532 nm, pump laser, green) was applied while simultaneously monitoring with a continuous low-power probe laser beam (633 nm, probe laser, red). Laser beam size was measured by the full width at half maximum (FWHM) of the Gaussian fitting (FIGS. 2B-C).

For PNB detection, a pump laser can be used at a fluence that activates all GNPs or only activates GNPs accumulated on viral particles for PNB generation, which can be in a range from 10 to 1000 mJ/cm$^2$ and having a wavelength within a range of 500 nm to 1150 nm. A pulse length duration (pulse width) can be used within a range of 1 ps to 100 ns and having a rate within a range of about 10-100,000 Hz.

Results. The digital plasmonic nanobubble detection (DIAMOND) can be used for nanoparticle quantification (FIG. 4a-c). A serial 75 nm AuNPs diluents were tested. The detection results suggests a single-particle sensitivity and absolute quantification due to the correlation between experimental results and theoretical prediction (Poission statistics).

DIAMOND can be used to determine the nanoparticle size. A serial AuNPs of different size but same concentration were tested (FIGS. 4D-F). The detection results suggests the as-generated PNB signals from each sample have high dependence on the nanoparticle size, allowing for the size determination. Notably, Small size mAb-NP (e.g., 15 nm) have low amplitude value. Large clusters of NPs (caused by mAb-NP-virus recognition and thus NP aggregation) will cause nonlinear amplification in amplitude of the nanobubble signals, leading to a decrease in LOD by digital plasmonic nanobubble detection.

DIAMOND can be used to differentiate the heterogeneity of a mixture suspension (FIGS. 5A-C). 15 nm and 75 nm AuNP suspensions and their mixture were tested. The agreement between experimental result and theoretical prediction indicates that DIAMOND provides accurate and absolute quantification of large NPs from a strong background of small ones (i.e., 1 in 240).

DIAMOND can be used to detect non-plasmonic particles in a homogeneous assay (FIGS. 6A-F). 15 nm AuNPs as probes were used to detect SiO$_2$ beads. The detection result suggests attomolar detection limit and absolute quantification.

Figure 7:
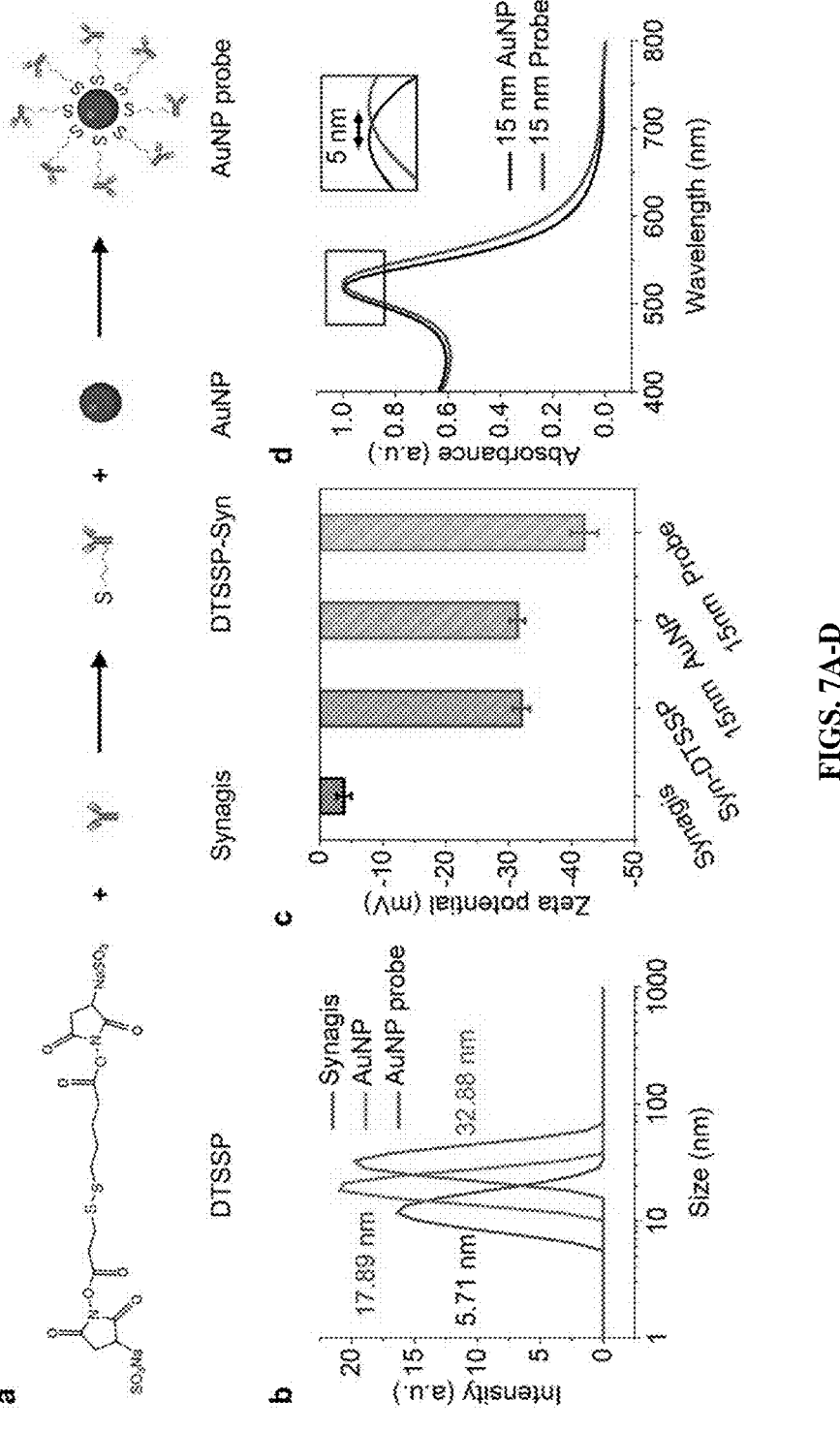

For antibody and GNP conjugation, 15 nm GNPs were tested. Polyethylene glycol (PEG) has been used to concentrate viruses. Thus, PEGylated method does not show the specific detection of viruses. Passive absorption has some limitations for long term storage of GNP-syn probes. In addition, free antibody desorbed from the GNPs would compete with GNP-conjugated antibody for RSV binding sites and result in decreased assay performance. The inventors explore another decent method using DTSSP bifunctional crosslinker to modify GNPs surface and create more stable GNP-DTSSP-syn probes, which would improve the integrity of the reagent. Filbrunet et al., *Analyst,* 142, 4456 (2017) reported that the hydrolysis of DTSSP occurs much faster than the reaction with the protein, which would result in similar surface charge as the original citrate-coated GNPs, and thus the DTSSP modified GNPs should be similar as the passive absorption case. The inventors decided to use "grafting-to" method to firstly conjugate DTSSP with Synagis and then incubate DTSSP-Syn with GNPs (FIG. 7A). In order to optimize the reaction condition, the buffer pH and the molar ratio of DTSSP to Synagis are varied to obtain the best outcome. Finally, The inventors successfully created GNP-DTSSP-Syn probes using 2 mM borate buffer (pH 8.5) with a molar ratio (DTSSP: Syn) of 125. The GNP conjugates lead to hydrodynamic diameter increase by around 20 nm (FIG. 7B), and absolute surface zeta potential increase by around 10 mV (FIG. 7C).

To implement the real RSV detection, clinical frozen stock of RSV A2 strain (from UTSW medical center) was seeded and propagated in HEp-2 cells (FIG. 9A) and purified by sucrose density gradient ultracentrifugation (FIG. 9B). The RSV titer (3.3×10$^6$ pfu/ml) was determined by plaque titration using endpoint titration (FIGS. 10A-B). After incubating GNP-DTSSP-Syn probes with a series dilution of real RSV, spectral absorbance measurements do not show obvious peak shift but have the magnitude change in optical density. RSV targeted by GNPs probes was confirmed by TEM imaging (FIGS. 11A-B). By analyzing the absorbance ratio of each sample, GNP-DTSSP-Syn can distinguish crude stocks of RSV from other respiratory viruses (FIG. 11C). The results suggest that the LOD of the analog assay is about $10^4$~$10^5$ PFU/mL. Kinetic study of colorimetric assay for real RSV indicates the diagnosis can be achieved within 30 minutes (FIG. 14).

A 5 OD 15 nm mAb-NP sample was evaluated to further test a series of dilution of RSV. Here, 2000 nanobubble signals are collected for each of the sample, and were analyzed by amplitude and area under curve (see FIG. 11D). After MATLAB analysis, the Ampl-AUC give a direct differentiation among different concentration of RSV samples (FIG. 11E). For simplicity, the inventors used Ampl-AUC two-parameter scatter analysis to quantitatively calculate the limit of detection. After setting the control region, they counted the target-specific signals outside of the control box. The calibration curve indicates the LOD is ~108 pfu/mL, comparing with colorimetric detection using the same size of AuNPs, nanobubble technique provide around ~333 times improvement in LOD.

The inventors are integrating their digital plasmonic nanobubble detection technique as a benchtop device (FIGS. 18A-B). The encasing for the device was constructed in a way to minimize the size of the device while allowing ample room for all of the components and for later adjustability of the laser pathway. The design team used a modifiable system for placing the mirrors and filters. The main compartment of the box houses the two lasers (Pump laser, 532 nm; Probe laser, 633 nm) and the first two steps of the filtering process. A high reflectance Aluminum mirror which reflects the pump laser at a 45° angle and dichroic mirror at a 45° angle which reflects the probe laser and allows the pump laser to pass, resulting in the two lasers being aligned. This compartment of the box also includes the stepped neutral density filter, which lies right at the pump laser. The next compartment of the box is the slide-out-drawer which houses the syringe, syringe pump system, capillary and waste collector. As the syringe pump flows the sample, the now-aligned lasers hit the capillary. It was important to design this compartment to be separated from sensitive components which may be damaged from exposure to the liquid sample. It was also important that this component was easily accessible so the sample could be inserted into the device quickly. Next, is the data acquisition compartment. The lasers then hit another dichroic mirror which allows the pump laser to pass and reflects the probe laser into a short pass filter to further filter out any remnants of the pump laser in the lower wavelengths. Then, the probe laser beam enters the photodetector where the changes in light change the voltage which is detectable and read via a portable oscilloscope. The last compartment houses the electrical components: the Arduino Uno, power strip, and all the cables. In a preferred embodiment, the pump laser beam source is a 532 nm picosecond pulsed laser generating pulses, with pulse width in the range of approximately 1 ps to 10 ns, at a rate in the range of about 10-100 Hz and delivering approximately 10-30 μJ per pulse. There are number of solid-state lasers available. The probe laser beam is a low-power (approximately 1 mW) 633 nm laser beam, for example, from a He—Ne laser.

The methods are applicable generally to the detection of infectious organisms such as viruses and bacteria, including for example respiratory infectious disease diagnosis, urinary tract infection (UTI) diagnosis, meningitis diagnosis in cerebrospinal fluid (CSF), or the like. The methods are also applicable to molecules detection, including those of DNA, proteins, oligonucleotides, etc. It will be appreciated that the term virus or infectious organism as used herein can be substituted for bacteria, oligonucleotide, or a combination thereof. Put in the context of clinical utility, the digital nanobubble method can significantly improve the clinical sensitivity for rapid RSV detection (Table 1).

TABLE 1

| Methods | Description | Advantages | Disadvantages |
|---|---|---|---|
| Virus Isolation | Cell culture for virus replication | Broad spectrum & high sensitivity | Living cells required Complexity Time to diagnosis typically >4 days |
| Electron Microscopy | Based on virus's morphology | Visualize the viruses | High degree of operator skill required Minimal number of viruses required Not practical for a large number of specimens |
| Complement Fixation Test | Titration of hemolytic serum and complement Titration of antigen and antibody | Low cost Screen against a large number of viral infectious at the same time | Not sensitive Time-consuming Often non-specific (cross reaction) |
| Serological techniques | Hemagglutination Inhibition (HI) Single Radial Hemolysis (SRH) Viruses neutralization (VN) | Relatively easy and inexpensive | Specificity varies with different viruses Sensitivity dependent on reagents, which can be variable |
| ELISA | Competitive methods Sandwich methods (indirect) Direct methods | High sensitivity High specificity | Many steps that include incubation, washing. Required specialized equipment for reading plates Minimal signal amplification |
| Immunoassays | Immunofluorescence (IF) Lateral flow assays (LFAs) | Simple Qualitative/semi-quantitative result | Highly dependent on the quality of the specimen Low sensitivity |
| Molecular Techniques | Nucleic acid probes (DNA/RNA) Polymerase chain Reaction (PCR) | High sensitivity Can be multiplexed | Expensive & time consuming Liable to contamination |
| Other Amplification | Ligase chain reaction (LCR) isothermal | Fast and high sensitivity Signal | Extra virus lysis step required |

TABLE 1-continued

| Methods | Description | Advantages | Disadvantages |
|---|---|---|---|
| Techniques | amplification QB replicase method, etc. | enhancement | |
| Digital PNB detection | GNP based aggregation assay Laser induced digital detection | Simple, fast and high sensitivity Applicable for broad range of viral infections | Need external power source |

Example 2: Enhancement of Plasmonic Sensor by Effective Binding of Gold Nanorods to Respiratory Syncytial Viruses Objective. Current commercial rapid diagnostic tests such as PCR or lateral flow assay for virus detection are either costly, time-consuming, or lack of sufficient sensitivity. Gold nanorods (GNRs) as a plasmonic sensor provide a simple yet reliable result for sensitive detection of the respiratory syncytial virus, enhancing the assay performance for rapid virus diagnostics.

Methods. Synthesis of GNRs. GNRs are prepared by a seeded-growth method as previously published with slightly modification. Briefly, the seeds will be prepared by reducing CTAB/HAuCl$_4$ mixture with NaBH$_4$ solution. GNRs will be prepared by first adding 5-bromosalicylic acid to a CTAB solution including AgNO$_3$, ascorbic acid, and HAuCl$_4$ and followed by adding a specific volume of the seed solution. The mixture will be left undisturbed at room temperature overnight. The localized surface plasmon resonance (LSPR) of GNRs can be varied with the volume of seeds solution.

Ligand exchange. The obtained GNRs suspension is first centrifuged multiple times and re-dispersed in a solution containing polyvinylpyrrolidone, ascorbic acid, and sodium citrate. After adding AgNO$_3$, the solution is centrifuged and re-dispersed in sodium citrate solution. A mixture of diluted ammonium hydroxide and hydrogen peroxide is added to the above solution. The GNRs suspension finally is collected by centrifugation.

Antibody and GNRs conjugation. Synagis (Palivizumab) was chosen as the RSV-specific monoclonal antibody, which can passively bind to RSV envelope fusion protein on the virus surface and block a critical step in the membrane fusion process. To conjugate Synagis onto GNRs surface, the inventors first modify Synagis with crosslinker DTSSP (3,3'-dithiobis (sulfosuccinimidyl propionate)) with a molar ratio of 1:125 to alter the surface charge of the antibody while keeping the affinity of the antibody and reducing the hydrolysis effect of the DTSSP. Then the modified Synagis was added to GNRs suspension to generate stable GNR-Syn probes. Same conjugation method is used for spherical gold nanoparticles (GNPs). The probes were further characterized by dynamic light scattering (DLS) and UV-Vis.

For colorimetric detection techniques, different sizes of Au sphere (15, 45, 100 nm) and Au rod (15 nm×50 nm) have been tested. The inventors used A280 method to estimate the amount of antibody coated on gold particles surface. The average concentration of Ab on each particle is estimated as 0.06-0.07/nm$^2$, which is about 50%-65% surface coverage for all of the tested sizes nanoparticles. Note that the protein coating density is related to the size of the AuNP. Particularly, the curvature of the surface (which is nanoparticle size related parameter) matters due to the protein-protein steric effects. The greater the surface curvature, the more antibodies can be packed on the nanoparticle surface. As the particle size becomes larger comparing with the size of the protein, this effect is expected to saturate, thus for the size range from 15 nm-100 nm, there's minimal difference in terms of surface coverage of antibody on particle. While having similar coating density of Ab on nanoparticles, larger size of particles will have a greater number of Ab loaded, which increases the binding efficiency of AuNP-Ab to viruses. AuNPs-based colorimetric assay results suggested 100 nm particles provide the lowest limit of detection (LOD=2.0× 10$^4$ pfu/ml) among spherical AuNPs. As for Au rod (15 nm×50 nm) with higher curvature at the end and larger side surface area bring the LOD to a much lower level (2.5×10$^3$ pfu/ml).

GNR-based Plasmonic coupling assay. RSV and other closely related respiratory viruses such as Human metapneumovirus (hMPV), Parainfluenza viruses (PIV), and Influenza Virus A (IVA) were then incubated with GNR-Syn probes for at least 30 min at room temperature in the presence of 5% sucrose and cell debris in 1×MHS buffer (1M MgSO$_4$, 0.5M HEPES pH7.7, 1M NaCl). The optical spectrum was measured using a Beckman Coulter UV-Vis spectrophotometer (model DU800), and the GNRs targeted virus samples were observed by transmission electron microscopy (TEM JEOL JEM 2100). Each of the GNRs samples was spotted onto a thin carbon film coated Cu grids (300 mesh, Pacific Grid Tech) and air-dried for TEM characterization.

Results. FIG. 19A and FIG. 19B provide the spectral absorbance and transmission electron microscopy image for the GNRs, respectively. FIG. 20A (top panel) shows TEM images of different GNPs-Syn probes before (i-v: 15 nm, 30 nm, 45 nm, 100 nm, 15 nm×50 nm rod) and after (vi-x: 15 nm+RSV, 30 nm+RSV, 45 nm+RSV, 100 nm+RSV, 15 nm×50 nm rod+RSV) incubated with RSV stock solutions. Scale bar=200 nm. FIG. 20B gives corresponding spectral absorbance of GNPs-Syn probes with different size before and after incubated with RSV stock solutions. FIG. 20C is the quantitative analysis of size and shape effects of GNPs on RSV binding. Table 2 provides a comparison of different nanoparticles probes in RSV detection performance.

FIG. 21A shows the spectral absorbance of GNRs probes incubated with a series of RSV dilutions. FIG. 21B shows the contour plot for optimization of wavelength ratio to achieve the sensitive detection of RSV. The yellow hot spot gives the optimized wavelength ratio of A830/A620. FIG. 21C presents the results of RSV detection using the GNRs probes. FIG. 21D shows a linear calibration curve for determination of limit of detection (LOD). The calculated LOD of RSV detection is 2456 pfu/ml.

Conclusion. The LOD of the assay by using GNRs as the sensors could reach around 2×10$^3$ pfu/ml, which is almost 10 to 100-fold lower than that of the gold nanoparticle-based assay. The binding effectiveness of gold nanoparticles to RSV can be highly improved when using GNRs probes, compared with that of spherical gold nanoparticles-based assay under the same condition, because more binding sites were provided by rods surface. This shape innovation has advanced the limit of detection into the level that well below mean nasal viral load on day 1 of infection (4.63±0.13 log PFU/mL).

TABLE 2

Comparison of different nanoparticles probes in RSV detection performance.

| Probe type | LOD |
| --- | --- |
| GNP 15 nm | $2.68 * 10^5$ pfu/ml |
| GNP 30 nm | $1.16 * 10^5$ pfu/ml |
| GNP 45 nm | $3.65 * 10^4$ pfu/ml |
| GNP 100 nm | $2.03 * 10^4$ pfu/ml |
| 15 nm × 50 nm GNR | 2456 pfu/ml |

Example 3: Silver-Based Nanoparticles as Plasmonic Sensors for Oligonucleotide Detection Background Simple and affordable diagnostics are accessible and indispensable tools supporting overburdened laboratories for sensitive pathogens detection, infectious diseases control, and timely healthcare delivery, especially for global pandemic like COVID-19. With the ability to detect analyte by presenting a color change, colorimetric assays have been recognized as such methods and are widely available in a variety of platforms for the detection of enzymes, specific compounds, antibodies, hormones, nucleic acids, and large biological particles (e.g., virus and bacteria). Unlike the gold standard enzyme-linked immunosorbent assay (ELISA), aggregation assays are rapid and one-pot homogeneous detection methods that can be performed by less-trained personnel without multiple washing steps. Using an inexpensive spectrophotometer, ordinary light microscope, or even naked eyes, those aggregation assays offer qualitative or quantitative measurements at low cost. However, conventional aggregation assays oftentimes use latex microparticles as labels (i.e., latex agglutination assay) for the sensing and have a low detection sensitivity compared to fluorescence-based assays.

The incorporation of metallic nanostructures (e.g., gold and silver nanoparticles, Au and AgNPs) in biosensing leads to the detection sensitivity enhancement. Whereas the unique localized surface plasmon resonance (LSPR) property and coupling effect of those NPs essentially provides the superior optical response that rival the latex beads and fluorescence dyes. For example, AuNPs of ~40 nm that are broadly used in colorimetric assays display an absorption cross-section 5 orders larger than ordinary organic dyes, while its polarizability in the dipole approximation is ~10 times larger than that of polystyrene beads with same diameter. Also, the stable scattering signals of those plasmonic NPs don't blink or bleach and are hardly affected by the environment, which is a considerable advantage over the organic fluorophores or semiconductor quantum dots. More importantly, the LSPR property of plasmonic NPs shows high correlation with a set of physical parameters, including composition, size, shape, and internal structure (e.g., solid vs. hollow), which has motivated us to tailor the properties via NP engineering. Compared to other strategies based on surface enhanced Raman spectroscopy, electrochemistry, and photothermal interrogation that require complicated instrumentation and additional labeling for the signal enhancement, it is more cost-effective and practical, especially for resource-limited settings.

Driven by the increasing demand of ultrasensitive assays, developing plasmonic biosensors with better plasmonic performance (i.e., plasmonic resonance and coupling) has been a highly interest subject in the past decade. Metallic nanostructures with hollow interior exhibit superior plasmonic activities compared to their solid counterparts, due to the plasmon hybridization that induces field enhancement from the inner and outer space. For example, Gao et al. demonstrated the Au—Ag nanocages (AuAgNCs) with 5 layers of walls show 10-fold larger peak extinction than that of AuNPs, ensuring detection sensitivity enhancement for lateral flow assay; while the Ag@(Ag—Au)NCs with varied inner Ag shell thickness display different colors, allowing naked eye discrimination for enzyme-linked immunosorbent assay. Despite those, the LSPR peaks of the AuAgNCs oftentimes locate in the near infrared region and thus is prominence for applications like photoacoustic imaging and targeted cancer therapy. On the other hand, plasmonic biosensors with LSPR peaks in the visible region and substantially enhanced extinction efficiency are more desired.

In this study, we have developed the Au—Ag nanoshells (AuAgNSs) based on a galvanic replacement reaction (GRR) with enhanced optical response and demonstrated its utilization as ultrasensitive colorimetric biosensors for the plasmonic coupling-based aggregation assay (PCA). Specifically, the AuAgNSs were prepared by initiating the GRR between Au+ ions (instead of $Au^{3+}$) and AgNPs as template for the growth (FIG. 23). By injecting the Au precursor (i.e., $HAuCl_4$) in the presence of sodium citrate ($Na_3CA$) as a reducing agent, the AuCl4- was quickly reduced into $AuCl_2^-$ and led to the formation of AuAgNSs with thick and solid wall, rather than porous AuAgNCs. Based on our experimental observation and simulation, we demonstrate that the AuAgNSs have restricted red shifting of LSPR peak within visible region and reduced quenching of peak intensity that is stronger than that of AuAgNCs and AuNPs. When applied to the PCA of oligonucleotides, AuAgNS-based probes achieve picomolar detection limit, which is over 100-times more sensitive than that of AuNPs of similar size, morphology, and peak position. These results indicate the great potential of Ag-based NP as plasmonic biosensors for a simple diagnostics of low-abundance molecules in point-of-care settings.

Materials and Methods. Preparation of 4 nm Ag nanoparticles as seeds. In a typical synthesis, ~4 nm AgNPs could be prepared by reducing aqueous $AgNO_3$ solution with $NaBH_4$ according to a previous report. Briefly, 2 mL of 1% (w/v) $Na_3CA$ solution and 6 mL of DI water were added to a 20 mL vial and preheated at 70° C. in an oil bath under magnetic stirring for 15 min, followed by sequentially adding 0.17 mL of 1% (w/v) $AgNO_3$ solution and 0.2 mL of 0.1% (w/v) $NaBH_4$ solution. The reaction was kept at 70° C. under vigorous stirring for 1 h. After cooling down to room temperature, the ~4 nm AgNPs were diluted to 10 mL using DI water and stored in dark for further use.

Preparation of 32 nm Ag nanoparticles as templates. 32 nm AgNPs were prepared based on a seeded-growth method according to a previous report. In brief, 5 mL of the prepared ~4 nm AgNPs as seeds, 1 mL of 1% (w/v) sodium citrate aqueous solution, 1 mL of 1% (w/v) AA aqueous solution, and 35 mL of DI water were mixted in a 100 mL flask and preheated at 80° C. in an oil bath under magnetic stirring for 15 min. Then, 0.85 mL of 1% (w/v) $AgNO_3$ solution was added into the mixture using a pipette. The reaction was kept at 80° C. under vigorous stirring for 1 h. The product was centrifuged and washed with DI water three times, redispersed in 50 mL of DI water, and stored in the dark for further use (0.224 nM in particle concentration).

Preparation of 42 nm AuAg nanoshells. 42 nm AuAg nanoshells were prepared via galvanic replacement reaction. In brief, 3 mL of the prepared ~32 nm AgNPs as templates, 1 mL of sodium citrate aqueous solution with varied concentration (0-50 mM), and 6 mL of DI water were mixted in a 50 mL flask and preheated at 95° C. in an oil bath under magnetic stirring for 15 min. Then, 0.004% (w/v) $HAuCl_4$ solution was injected into the mixture using a syringe pump at a speed of 6 mL/h for 10 mL. After injection, the reaction was kept at 95° C. under vigorous stirring for 10 min. The product was centrifuged and washed with DI water three times, redispersed in 3 mL of DI water, and stored in the dark for further use.

Preparation of 42 nm Au nanoparticles. 42 nm AuNPs were prepared by a two-step seeded-growth method according to a previous report. In the first step, ~15 nm AuNPs were first synthesized using the classical Frens' method. Briefly, 50 mL of $HAuCl_4$ aqueous solution (0.01%, w/v) was added to a 100-mL flask and heated to boiling under vigorous magnetic stirring. Then, 2 mL of $Na_3CA$ solution (1%, w/v) was added into the boiling solution. The reaction was kept boiling for 30 min until its color turned to red. After cooling down, the ~15 nm AuNPs as seeds were used for the growth of 40 nm AuNPs. Specifically, 2 mL of the ~15 nm AuNPs was mixed with 18 mL DI water in a 50-mL flask at room temperature under vigorous magnetic stirring. Subsequently, 10 mL of precursor aqueous solution containing 420 μL of $HAuCl_4$ solution (1%, w/v) and 10 mL of reducing agent containing 0.6 mL of AA solution (1%, w/v) and $Na_3CA$ solution (1%, w/v) were injected separately to the flask at a rate of 12 mL/h using a syringe pump. Finally, the ~42 nm AuNPs as product were cooled down to room temperature, and stored in dark at room temperature for future use. The AuNP concentration was determined based on the size-dependent empirical formula with a combination of UV-vis measurement and transmission electronic microscopy (TEM) image.

Preparation of nanoparticle-oligonucleotide as probes. NP-oligo conjugation was performed according to our previous work. The poly A-tail probe oligonucleotides were first resuspended in DI water per vendor suggestions before use. The SH-capped oligonucleotides A and B were conjugated separately to NPs by a pH-assisted and surfactant-free method. Briefly, NP suspension was mixed with oligonucleotide solution before adding a 50 mM citrate-HCl buffer with pH of 3.0±0.1 in a 1:1 volumetric ratio. After 30 min of incubation at room temperature, the NP-oligo conjugates were centrifuged and washed with DI water for three times. The purified products were redispersed in DI water and stored in the 4° C. refrigerator for further use.

Colorimetric assay of oligonucleotide. In a standard approach, a hybridization buffer (20% formamide, 16% dextran sulfate, and 0.6 M NaCl solution) was mixed with NP probe A and B solution in a volume ratio of 4:3:3. The freshly prepared working solution was then added to the target samples at different concentrations (volume ratio=2: 1). The solution was then incubated at room temperature for 30 min prior to the UV-vis measurement.

Figure 25:
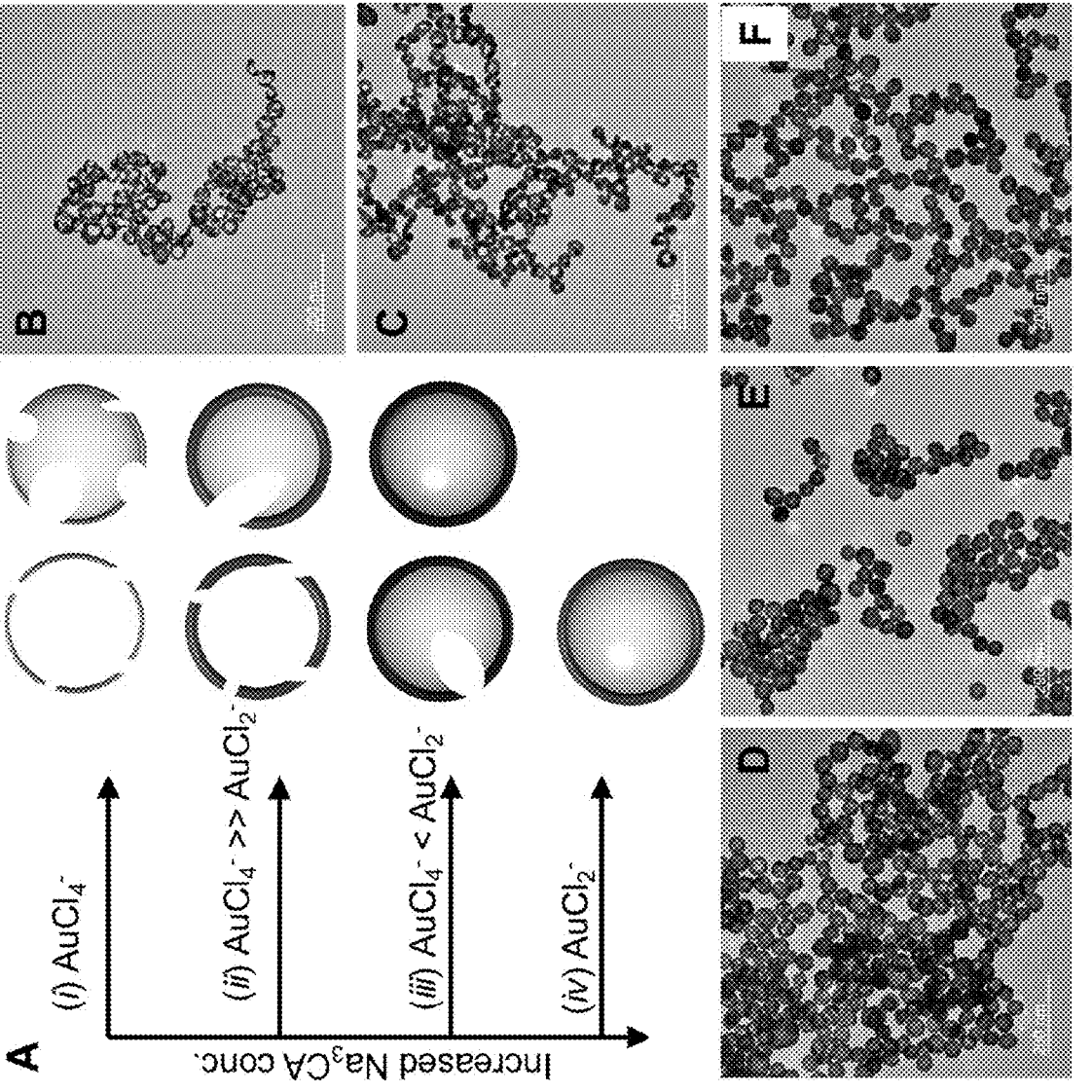

Results and Discussion. FIGS. 22A-C provide the transmission electron microscopy images for the silver nanoparticles and hollow gold-silver alloy nanoshells and nanocages, respectively. FIG. 23 is the schematic illustration of the growth of gold-silver alloy nanoshells/nanocages. FIG. 25 shows the impact of $Na_3CA$ concentration in nanoparticle synthesizing process. The concentration of $Na_3CA$ affects morphology and spectrum of the product. The more $Na_3CA$ added in the reaction, the more nanoshell will be in the product, and the higher peak extinction of the absorbance. Also, the peak position will be restricted in the visible region when more $Na_3CA$ is added. FIGS. 26A-C provide the results of oligonucleotide detection using the silver-based nanoparticles as sensors. Conditions are kept the same for all experiments.

Figure 24:
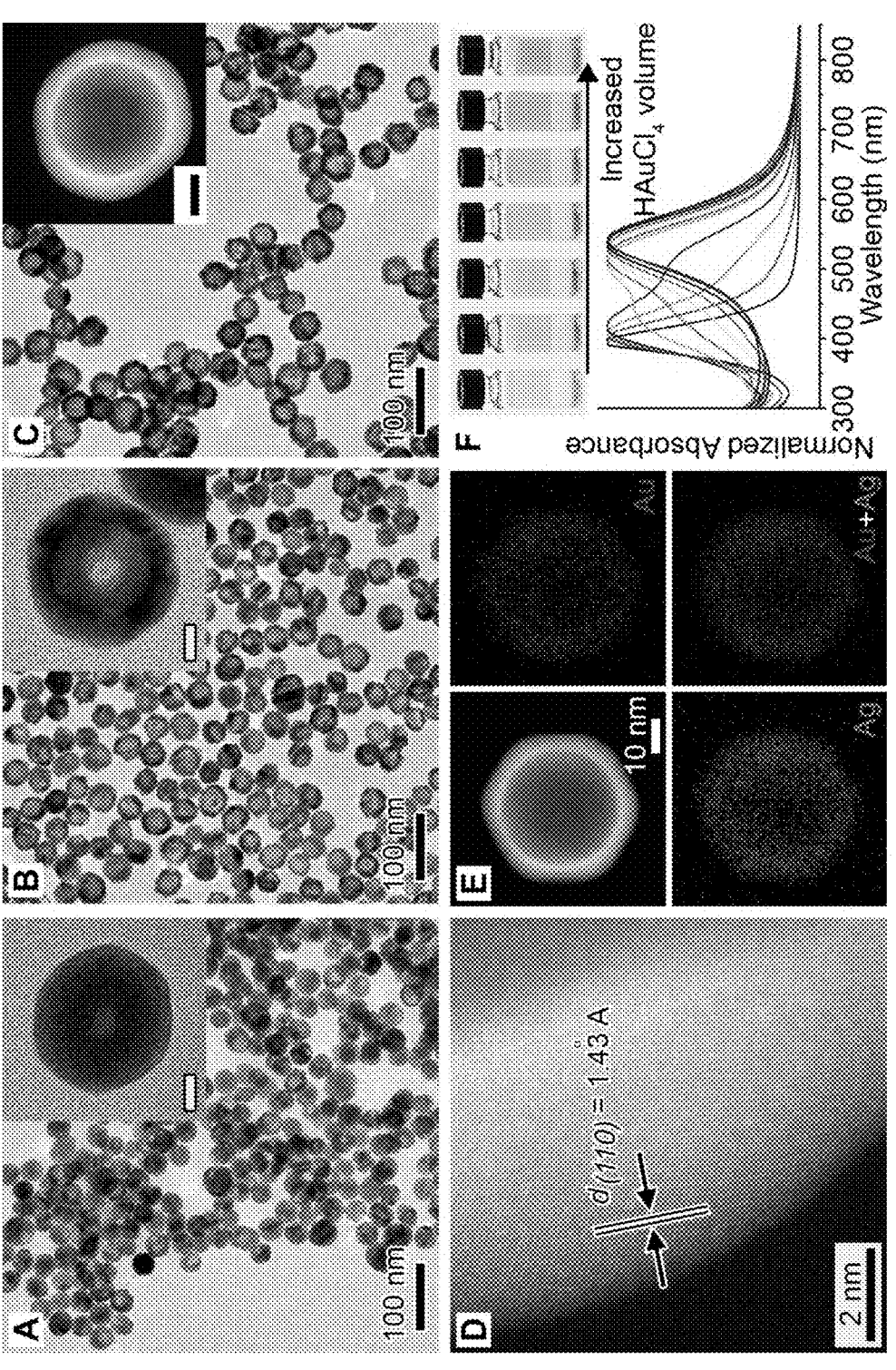

Impact of $HAuCl_4$ volume, concentration, and injection speed. Injecting different volumes of $HAuCl_4$ results in varied morphologies and red-shifting spectra of products (FIG. 24). Doubling the $HAuCl_4$ concentration and/or injection speed results in fast reaction and thus nanocage-dominated products.

The completed assay was subjected to quantification using UV-vis spectroscopy. The peak ratio of absorbance at 650 nm and 535 nm of AuAgNSs was used for the correction with target DNA concentrations. A quantitative linear relationship ($R^2$=0.994) in the range of 10-100 pM was observed for the AuAgNS-based PCA (FIG. 26B). The LOD, defined as the concentration corresponding to a signal that is 3 times the standard deviation above the zero calibrator, was calculated to be 3.9 μM. This value, as compared with that of AuNP-based PCA (LOD=415 μM, FIG. 32), indicating a 106-fold enhancement for the detection sensitivity.

Conclusions. The limit of detection of the assay by using the new types of silver-based nanoparticles as the sensors could reach around 4 μM, which is almost 100-fold lower than that of the gold nanoparticle-based assay. The inventors have demonstrated a PCA using AuAgNSs as signal reporters. Such NPs were prepared by coupling the galvanic replacement reaction and co-reduction reaction. The enhanced detection sensitivity (2 orders of magnitude) is ascribed to the superior optical response of the AuAgNSs that allows them to have stronger plasmonic coupling effect than that of the pure AuNPs.

Example 4: A Digital Nanobubble Method for Virus or Target DNA Detection

Various embodiments are conceived based on the experimentation and experimental results described in other sections contained in this provisional patent application. The descriptions of the various embodiments of the present disclosure are presented for purposes of illustration but are not intended to be exhaustive or limited to the embodiments disclosed. Many modifications and variations will be apparent to those of ordinary skill in the art without departing from the scope and spirit of the described embodiment. The terminology used herein was chosen to best explain the principles of each embodiment, the practical application or technical improvement over technologies found in the marketplace, or to enable others of ordinary skill in the art to understand the embodiments disclosed here.

According to some embodiments for the present disclosure, an apparatus is provided as shown in FIG. 2A. The apparatus includes a pump laser source generating a set of pump laser light pulses, a probe laser source generating a probe laser beam wherein the pump laser light and probe laser light beam are collinear and transmitted through a volume of incubated solution which is made to flow through a transparent capillary tube. A monoclonal antibody (mAb) specific to a particular virus (V) is conjugated to metal nanoparticles to create metal-mAb probes in a nanoparticle mixture. One incubated solution contains the nanoparticle mixture incubated with a clinical fluid specimen that is known not to contain the virus V (control solution). Another incubated solution contains the nanoparticle mixture incubated with a clinical fluid specimen that potentially contains the virus V at an unknown concentration C (test solution). With the presence of the virus V, the metal-mAb forms aggregates on the viral surface (the metal-mAb-V aggregates). The object of the instrument and method is to determine the presence of the virus V in the clinical fluid specimen and the concentration C as shown in two example embodiments.

The probe laser beam transmission is detected by a photodetector after appropriate filtering and analyzed, for example by an oscilloscope, to measure a time series of transmitted probe laser signals and to create a set of plots. Probe light from the probe laser beam is scattered or transmitted by particles and nanobubbles in the capillary volume. If there are metal-mAb-V aggregates within the incubated solution, there will be more probe light scattered by the particles (or the nanobubbles generated therefrom) than if there are no metal-mAb-V aggregates present in the incubated solution. Also, if there are metal-mAb-V aggregates within the incubated solution, there will be less probe light transmitted through the solution than if there are no metal-mAb-V aggregates present in the incubated solution. According to FIG. 27B, the transmitted probe signals are generally v-shaped and differ in shape when the virus is present in the incubated solution due to the presence of metal-mAb-V aggregates and the creation of relatively larger nanobubbles by the pump laser light pulses in the volume than relatively smaller nanobubbles generated by non-aggregated metal-mAb (i.e., virus V is not present). The shape of the transmitted probe signals can be characterized by amplitude (A), lifetime (L) and area-under-curve (AUC). The AUC can be defined as the area of the probe signal curve below a baseline during a sample period. The lifetime of the probe signal is measured as the time from the incidence of a pump laser pulse until the signal goes below a certain pre-defined level.

The presence of virus in the incubated solution can be determined by analyzing the transmitted probe signal shape. For example, a first embodiment is shown as method 150 in the flowchart of FIG. 27A with the help of the schematic plots of FIG. 1A. According to method 150, the AUC may be measured over many time periods for the control solution and for the test solution and used to determine the presence and concentration of the virus.

Method 150 may be accomplished using the apparatus 10 of FIG. 2A. At step 151, a virus specific antibody is conjugated to metal nanoparticles to create metal-mAb probes in a nanoparticle mixture. At step 152, the metal-mAb probes in the nanoparticle mixture are incubated with a clinical fluid specimen to be tested for the presence of the virus (V) for 30 minutes. If the virus is present, it will form a solution having a concentration of metal-mAb-V aggregates. If the virus is not present, only metal-mAb probes are present after 30 minutes. At step 154, the incubated solution (potentially containing metal-mAb-V aggregates) are flowed through the capillary volume at a prescribed flow rate. In alternate embodiments, the incubated solution is flowed or placed into a transparent vessel volume. According to the embodiments described herein, the metal nanoparticles may be Au spherical nanoparticles, Au nanorods, Ag spherical nanoparticles or Au—Ag-shell nanoparticles.

The methods are applicable generally to the detection of infectious organisms such as viruses and bacteria, including for example respiratory infectious disease diagnosis, urinary tract infection (UTI) diagnosis, meningitis diagnosis in cerebrospinal fluid (CSF), or the like. The methods are also applicable to molecules detection, including those of DNA, proteins, oligonucleotides, etc. It will be appreciated that the term virus or infectious organism as used herein can be substituted for bacteria, oligonucleotide, or a combination thereof. In some embodiments, the methods may be used to determine presence of a target DNA instead of a virus. For example, an oligonucleotide can be conjugated to a metal nanoparticle, according to methods described herein with respect to viruses. Based on the same principle of the GNPs aggregation assay disclosed herein, the oligonucleotide conjugated metal nanoparticles can undergo hybridization in the presence of a target DNA. The target sequence leads to head-to-tail clustering of GNPs. The DNA-conjugated sample can then be flowed through a micro-capillary channel (e.g., ID=200 μm) to perform the digital nanobubble detection.

At step 156, the capillary (or vessel) volume containing the incubated solution is irradiated with pulsed light from a pump laser beam source. Concurrently, at step 158, the capillary (or vessel) volume containing the metal-mAb-V aggregates are irradiated with continuous wave (CW) light from a probe laser beam source of a different wavelength than the pump laser beam source.

In a preferred embodiment, the pump laser beam source is a 532 nm picosecond pulsed laser generating pulses, with pulse width in the range of approximately 1 ps to 10 ns, at a rate in the range of about 10-10,000 Hz and delivering approximately 10-30 μJ per pulse. There are number of solid-state lasers available. The probe laser beam is a low-power (approximately 1 mW) 633 nm laser beam, for example, from a He—Ne laser.

In a preferred embodiment, at step 160, the transmitted probe light intensity is detected by a photodetector as a probe light signal during a time proceeding a pump pulse and prior to the next pump pulse in a series of pump pulses. If the incubated solution is the control solution, steps 170, 172, 174, and 176 are performed. If the incubated solution is the test solution, steps 180, 182, 184, 186, and 188 are performed.

At step 170, for the control solution, a number of probe light signals are processed to determine amplitude (A), area-under-curve (AUC) and lifetime (L) for a series of pump pulses which is stored in a data repository. At step 172, the preceding steps are counting the storing each control data point (A, AUC, L) for each pump pulse to determine thresholds for each parameter ($T_{ctrl-A}$, $T_{ctrl-AUC}$, and $T_{ctrl-L}$). The threshold values can be determined by 1-10 times standard deviation above the average value of a set of data points. In step 174, abnormal signals among all the probe light signals will be sorted out, if one parameter of the signals has a large value than that of the thresholds. Those abnormal signal frequency ($f_{on-ctrl}$) can be calculated by dividing its number to the total counting number.

At step 180, for the test solution, a number of probe light signals are processed to determine amplitude (A), area-under-curve (AUC) and lifetime (L) for a series of pump pulses which are stored in a data repository. At step 182, individual signals will be compared to the thresholds from step 172 with respect to the three parameters above. If one signal has a parameter that is larger than the $T_{ctrl}$, this signal will be counted as "on" signals and its frequency ($f_{on-test}$) will be calculated in step 184. If a signal has all parameters that are smaller than those of the thresholds, it will be counted as "off" signal. Such "on" and "off" counting is termed as digital counting and each "on" signal refers to as one virus being detected. In step 186, the $f_{on-test}$ will be compared to the $f_{on-ctrl}$, if the $f_{on-test}$ is larger than $f_{on-ctrl}$, it means the presence of virus in the test solution. In step 188, the viral particle concentration (C) can be calculated based on the following equation: $C=-\ln (1-(f_{on\text{-}test}-f_{on\text{-}ctrl})/V$, where the V is the volume, equaling 16 picoliter.

Example 5: A Colorometric Based Method for Virus or Target DNA Detection Using Metal Nanoparticles Various embodiments are conceived based on the experimentation and experimental results described in other sections contained in this provisional patent application. The descriptions of the various embodiments of the present disclosure are presented for purposes of illustration but are not intended to be exhaustive or limited to the embodiments disclosed. Many modifications and variations will be apparent to those of ordinary skill in the art without departing from the scope and spirit of the described embodiment. The terminology used herein was chosen to best explain the principles of each embodiment, the practical application or technical improvement over technologies found in the marketplace, or to enable others of ordinary skill in the art to understand the embodiments disclosed here.

According to some embodiments for the present disclosure, a method 200 is provided as shown in FIGS. 28 and 29 for the coupling of amplification of nucleic acids from infectious pathogen, such as an isothermal amplification process of virus RNA, and metal-based NP colorimetric assay 270 for the detection of viral nucleic acids.

The isothermal amplification process 250 is shown in steps 201-204 in FIG. 30 and in the schematic diagram of FIG. 31. At step 201, RNA fragments are extracted from a clinical fluid specimen. The RNA sequence may be extracted, for example, from a virus: the clinical fluid specimen having a concentration C of the virus. At step 202, a reverse transcription coupled with isothermal amplification of the viral RNA into multiple copies of double-strain DNA (dsDNA) is performed using a commercially available kit (e.g., WarmStart® LAMP Kit (DNA & RNA) cat #E1700S, NEB). At step 203, restriction enzyme digestion is performed resulting in short sequence of dsDNA. Both isothermal amplification and restriction enzyme digestion are described in greater detail in world-wide-web at neb-.com/applications/dna-amplification-pcr-and-qpcr/isothermal-amplification and neb.com/tools-and-resources/video-library/restriction-enzyme-digest-protocol-cutting-close-to-dna-end, the contents of which are incorporated by reference herein in its entirety. At step 204, the dsDNA is separated into single-strand target DNA, by means of heat, for detection. The dsDNA contains the virus-specific sequence (and associated virus). A standard kit may be used to calculate the amplification factor, k, of RNA sequence to single strand target DNA sequences. The resulting testing sample comprises the target DNA sequence from step 204.

A working solution containing metal-NP probes is prepared according to process 260 of FIGS. 29 and 31. According to FIG. 29, process 260 is shown in detail in steps 210 and 212. At step 210, a virus (V) specific pair of oligonucleotides is conjugated to metal nanoparticles to create metal-oligo probes in a nanoparticle probe mixture. Each oligonucleotide contains the sequence complimentary to the same single-stranded DNA of dsDNA from step 203 with a gap of 5-20 nucleotides; both do not anneal to each other under any testing condition. At step 212, the metal-oligo probes are mixed in a hybridization buffer to form a working solution. According to the embodiments described herein, the metal nanoparticles may be Au spherical nanoparticles, Au nanorods, Ag spherical nanoparticles, Au—Ag-nanoshells or Au—Ag nanocages as described in the other sections of this provisional application.

The colorimetric assay 270 is then performed by incubating the working solution with the testing sample containing the target DNA sequence as shown in step 215. Typical incubation time period is 10 minutes to 30 minutes or less. In alternate embodiments, any target DNA sequence may be tested according to the colorimetric assay 270 using an appropriate metal-oligo working solution with appropriate oligonucleotides conjugated to metal NPs.

Mixing the working solution with the testing sample and negative control sample (virus-free specimen in step 201) results in different visual colors. After the incubation time period of step 215, the testing sample solution will have a resultant visual color which may differ from the visual color of negative control sample and the incubated solution may be qualitatively assessed and quantitatively assessed as shown in process 200. At step 230, a qualitative assessment is performed which is simply to compare the resultant visual color of the testing sample solution to the visual color of the negative control sample solution. Step 230 may be performed by the naked eye or it may be performed using a spectrometer. If the resultant visual color is substantially more blue than the initial visual color then the virus is determined to be present (positive result). If there is no change in color during the incubation time period, then the virus is determined to be absent (negative result), at least in concentrations less than a known limit of detection for step 230. However, the quantitative assessment may be performed in the case of a negative result for step 230 to further evaluate the presence and concentration of the virus (or target DNA).

A quantitative assessment of the colorimetric assay 270 is performed according to process 200 beginning at step 216, where the spectral absorbance of the testing sample solution and negative control sample solution are performed. Specifically, spectral absorbance is measured in two spectral bandwidth regions, A1 and A2, centered on wavelengths A and 22, respectively. An example of resulting spectral absorbance curves are shown in FIG. 32 with and without target DNA present in the incubated solution. Table 3 shows a preferred choice of bandwidth regions for AgNPs, AuAg nanoshells, AuAg nanocages, Au NP and Au NRs. At step 218, the measured absorbance ratio is formed from the two measured spectral absorbances $A_1$ and $A_2$: $\alpha=A_2/A_1$.

According to step 220, a calibration curve is pre-determined using standard samples of virus RNA (or target DNA) with known concentrations. A limit of detection (LOD) and an absorbance ratio threshold $\alpha_{th}$ is determined from this calibration curve, for example, by 3 times the standard deviation of background signal divided by slope of the regression equation. In FIG. 33, an example calibration curve 280 is shown for various target DNA concentrations (DNA sequence for malaria) with an associated LOD 281 and associated $\alpha_{th}$ 282.

At step 225, the measured absorbance ratio $\alpha_t$ is compared to the absorbance ratio threshold $\alpha_{yt}$. If the measured absorbance ratio is less than or equal to the absorbance ratio threshold, then the virus (or target DNA) is determined to be absent (negative result, step 229). If the measured absorbance ratio is greater than the absorbance ratio threshold, then the virus (or target DNA) is determined to be present (positive result, step 228). Then in step 230, this at is referred to the calibration curve to find the corresponding concentration of target sequence after amplification.

An optional step (not shown) of further quantifying the concentration of virus (or target DNA) may be performed using the calibration curve. Using the measured absorbance ratio, at, the target DNA concentration $C_0$ may be measured for the testing solution by simple lookup in a curve fit to the calibration curve. Then the initial concentration C of virus in the clinical fluid specimen can be determined by $C=C_0/k$ where k is the amplification factor as determined in step 204.

Typical limit of detection using the colorimetric detection for DNA is 4 μM using AuAg nanoshell and AgNP, and 400 μM for AuNP (FIG. 34). With a factor of $10^6 \sim 10^7$ amplification, typical limit of detection is 0.4-4 aM, which is single molecule level per microliter volume.

In an embodiment for the present disclosure, synthetic SARS-COV-2 RNA (Twist Bioscience SARS-COV-2 RNA Control 2, #102024) is tested (FIG. 35). In a standard test, 8 microliter of RNA sample is mixed with 10 microliter of reverse transcription-loop-mediate amplification (RT-LAMP) solution (commercially available, WarmStart® LAMP Kit (DNA & RNA) cat #E1700S, NEB) and 2 microliter of a set of primers. The mixture solution is incubated at 60-65° C. for 15-60 min. 2 microliter of the product is then mixed with 48 microliter of enzyme solution containing 1.5 microliter of both restriction enzymes (HincII, #R0103S, and EaeI, #R0508S, NEB), 5 microliter of rCutSmart™ Buffer (#R0508S, NEB) solution, and 40 microliter of water. The mixture solution is incubated at 37° C. for 15-60 min. The product is then heated at 95° C. in a heating block for 5 min and cooling down to room temperature on ice. Afterwards, the solution is mixed with working solution and incubated at 62° C. for 10-30 min. A color change can be observed if there is ~10 copies per microliter target RNA is present.

TABLE 3

| Probes | $A_1$ region (nm) | $A_2$ region (nm) |
|---|---|---|
| AgNPs | 380-450 | 480-550 |
| AuNPs | 520-550 | 580-630 |
| AuNRs | 650-950 | 750-1050 |
| AuAgNSs | 500-650 | 600-750 |
| AuAgNCs | 600-900 | 700-1000 |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

What is claimed:

1. A method of detecting an analyte in a sample comprising:
   (a) providing a binding agent comprising a gold nanoparticle, an antibody or analyte-binding fragment thereof that selectively binds to an analyte, wherein said antibody or analyte-binding fragment thereof is linked to said gold nanoparticle;
   (b) contacting said binding agent with a sample containing or suspected of containing said analyte, wherein binding of said binding agent to said analyte induces nanoparticle aggregation;
   (c) subjecting the product of step (b) to a laser, thereby inducing nanobubbles when nanoparticle aggregates are present; and
   (d) detecting binding of said binding agent to said analyte by optical detection of nanobubbles,
   wherein step (c) comprises optically detecting light amplitude and area under the curve.

2. The method of claim 1, wherein said detecting is quantitative or semi-quantitative.

3. The method of claim 1, wherein said detecting is non-quantitative.

4. The method of claim 1, wherein said analyte is a protein, peptide, oligonucleotide, polynucleotide, a lipid, or a carbohydrate.

5. The method of claim 1, wherein said analyte is a virus, a bacterium, a fungus, or a cell.

6. The method of claim 1, wherein said analyte is a non-biological chemical compound, or a metal ion.

7. The method of claim 1, wherein said antibody is a single chain antibody, bispecific antibody, or a polyvalent antibody.

8. The method of claim 1, wherein said antigen binding fragment is a Fab, a $F(ab)_2$, a scFv or aptamer.

9. The method of claim 1, further comprising a control reaction where said binding agent is contacted with a second sample containing said analyte.

10. The method of claim 1, further comprising a control reaction where said binding agent is contacted with a second sample lacking said analyte.

11. The method of claim 1, wherein steps (b) and (c) are completed in less than one hour.

12. The method of claim 1, wherein the laser is nanosecond or picosecond laser.

13. The method of claim 5, wherein said virus is respiratory syncytial virus (RSV) or SARS-COV-2.

14. The method of claim 1, wherein step (d) employs a handheld optical detection device.

15. The method of claim 1, wherein said sample is a biological sample, an environmental sample, a food sample, or a drug sample.

16. The method of claim 6, wherein said non-biological chemical compound is a small molecule drug, a pesticide, a herbicide, a polymer, a toxin, an industrial by-product or waste product.

17. The method of claim 6, wherein said metal is a heavy metal ion.

18. The method of claim 9, wherein the amount of said analyte in said second sample is known.

19. The method of claim 11, wherein steps (b) and (c) are completed in about 30 minutes.

\* \* \* \* \*